United States Patent
Fairman et al.

(10) Patent No.: US 12,252,454 B2
(45) Date of Patent: Mar. 18, 2025

(54) CARRIER-PROTEIN POLYSACCHARIDE CONJUGATION METHODS

(71) Applicant: Vaxcyte, Inc., San Carlos, CA (US)

(72) Inventors: Jeffery C. Fairman, Mountain View, CA (US); Neeraj Kapoor, Foster City, CA (US); Lucy Estella Pill, Burlingame, CA (US); Scott Snyder, Union City, CA (US)

(73) Assignee: Vaxcyte, Inc., San Carlos, CA (US)

( * ) Notice: Subject to any disclaimer, the term of this patent is extended or adjusted under 35 U.S.C. 154(b) by 133 days.

(21) Appl. No.: 18/171,055

(22) Filed: Feb. 17, 2023

(65) Prior Publication Data

US 2023/0183147 A1    Jun. 15, 2023

Related U.S. Application Data

(63) Continuation of application No. PCT/US2021/046432, filed on Aug. 18, 2021.

(60) Provisional application No. 63/067,752, filed on Aug. 19, 2020.

(51) Int. Cl.
  *C07B 37/10* (2006.01)
  *A61K 47/54* (2017.01)
  *A61K 47/62* (2017.01)
  *C07K 1/107* (2006.01)
  *C07K 19/00* (2006.01)

(52) U.S. Cl.
  CPC ............ *C07B 37/10* (2013.01); *A61K 47/545* (2017.08); *A61K 47/62* (2017.08); *C07K 1/1077* (2013.01); *C07K 19/00* (2013.01)

(58) Field of Classification Search
  None
  See application file for complete search history.

(56) References Cited

U.S. PATENT DOCUMENTS

| | | |
|---|---|---|
| 5,679,782 A | 10/1997 | Rosenberg et al. |
| 7,375,234 B2 | 5/2008 | Sharpless et al. |
| 8,133,515 B2 | 3/2012 | Boons et al. |
| 8,426,649 B2 | 4/2013 | Popik et al. |
| 8,541,625 B2 | 9/2013 | Popik et al. |
| 8,859,629 B2 | 10/2014 | van Delft et al. |
| 8,912,322 B2 | 12/2014 | Popik et al. |
| 9,315,468 B2 | 4/2016 | Boons et al. |
| 9,682,934 B2 | 6/2017 | Stafford et al. |
| 9,994,527 B2 | 6/2018 | Stafford et al. |

(Continued)

FOREIGN PATENT DOCUMENTS

| | | |
|---|---|---|
| EP | 2 945 641 B1 | 1/2020 |
| WO | WO-2006/082530 A2 | 8/2006 |

(Continued)

OTHER PUBLICATIONS

Abrahams, C. L. et al. (2018). "Targeting CD74 in multiple myeloma with the novel, site-specific antibody-drug conjugate STRO-001," Oncotarget 9:37700-37714.

(Continued)

*Primary Examiner* — Tam M Nguyen
(74) *Attorney, Agent, or Firm* — Ron Galant; Polsinelli PC

(57) ABSTRACT

The present disclosure provides methods of preparing heteroaryl-containing compounds, wherein an azide-alkyne cycloaddition is accelerated in the presence of lauryldimethylamine oxide (LDAO). The present disclosure further provides conjugates of polypeptides and antigens prepared using such methods.

29 Claims, 13 Drawing Sheets

Specification includes a Sequence Listing.

(56) References Cited

U.S. PATENT DOCUMENTS

| | | | |
|---|---|---|---|
| 10,112,900 | B2 | 10/2018 | Stafford et al. |
| RE47,539 | E | 7/2019 | Popik et al. |
| 10,730,837 | B2 | 8/2020 | Stafford et al. |
| 11,135,300 | B2 | 10/2021 | Adamo et al. |
| 11,548,852 | B2 | 1/2023 | Stafford et al. |
| 2012/0208722 | A1 | 8/2012 | Dluhy et al. |
| 2014/0256626 | A1 | 9/2014 | Santi et al. |
| 2017/0002012 | A1 | 1/2017 | van Delft et al. |
| 2017/0008858 | A1 | 1/2017 | van Delft et al. |
| 2017/0096443 | A1 | 4/2017 | Dhar et al. |
| 2018/0333484 | A1 | 11/2018 | Fairman et al. |
| 2019/0055300 | A1 | 2/2019 | Hirasawa et al. |
| 2020/0054739 | A1 | 2/2020 | Fairman et al. |
| 2022/0125907 | A1 | 4/2022 | Kapoor et al. |

FOREIGN PATENT DOCUMENTS

| | | |
|---|---|---|
| WO | WO-2006/082530 A3 | 8/2006 |
| WO | WO-2009/067663 A1 | 5/2009 |
| WO | WO-2011/136645 A1 | 11/2011 |
| WO | WO-2012/035519 A1 | 3/2012 |
| WO | WO-2012/177701 A2 | 12/2012 |
| WO | WO-2012/177701 A3 | 12/2012 |
| WO | WO-2013/020090 A2 | 2/2013 |
| WO | WO-2013/020090 A3 | 2/2013 |
| WO | WO-2014/036492 A1 | 3/2014 |
| WO | WO-2018/187515 A1 | 10/2018 |
| WO | WO-2020/009993 A1 | 1/2020 |
| WO | WO-2020/010000 A1 | 1/2020 |
| WO | WO-2020/010016 A1 | 1/2020 |
| WO | WO-2020/072681 A1 | 4/2020 |
| WO | WO-2020/205584 A1 | 10/2020 |
| WO | WO-2021/167996 A1 | 8/2021 |
| WO | WO-2022/178015 A1 | 8/2022 |

OTHER PUBLICATIONS

Anderton, G.I. et al. (2015). "Accelerating Strain-Promoted Azide-Alkyne Cycloaddition Using Micellar Catalysis," Bioconjug Chem 26:1687-1691.

Baskin, J. M. et al. (2007). "Bioorthogonal Click Chemistry: Covalent Labeling in Living Systems," QSAR & Combinatorial Science 26:1211-121.

Beal, D.M. et al. (2012). "Click-enabled heterotrifunctional template for sequential biconjugations," Organic & Biomolecular Chemistry 10:548-554.

Bernard, A. R. et al. (2016). "Detergent Isolation Stabilizes and Activates the Shigella Type III Secretion System Translocator Protein IpaC," J. Pharm. Sci. 105:2240-2248.

Bharathi, M.V. et al. (2015). "Development of surface immobilized 3-azidocoumarin-based fluorogenic probe via strain promoted click chemistry," Bioorganic & Medicinal Chemistry Letters 25:5737-5742.

Blast Alignment Tool (2023). Located at https://blast.ncbi.nlm.nih.gov/Blast.cgi, 2 total pages.

Chen, X. et al. (2015). "Impact of detergent on biophysical properties and immune response of the IpaDB fusion protein, a candidate subunit vaccine against Shigella species," Infect. Immun. 83:292-299.

Chio, T. I. et al. (2020). "Click Chemistry Conjugations," Methods Mol. Biol. 2078:83-97.

Constantino, P. et al. (2011). "The design of semi-synthetic and synthetic glycoconjugate vaccines," Expert Opin. Drug Discovery 6:1045-1066.

Davis, D. L. et al. (2016). "Effect of Buffer Conditions and Organic Cosolvents on the Rate of Strain-Promoted Azide-Alkyne Cycloaddition," The Journal of Organic Chemistry 81:6816-6819.

Debets, M.F. et al. (2010). "Aza-dibenzocyclooctynes for fast and efficient enzyme PEGylation via copper-free (3+2) cycloaddition," Chem. Commun. 46:97-99.

Dommerholt, J. et al. (2016). "Strain-Promoted 1,3-Dipolar Cycloaddition of Cycloalkynes and Organic Azides," Topics in Current Chemistry 374:16.

Green, C. et al. (2018). "A Simple Approach to Pneumococcal Vaccination in Adults," J. Glob. Infect. Dis. 10:159-162.

Henikoff, S. et al. (1992). "Amino acids substitution matrices from protein blocks," PNAS 89:10915.

Hu, X. et al. (2018). "Efficient and Selective Bioconjugation Using Surfactants," Bioconjug Chem 29:3667-3676.

Huisgen, R. (1984). 1,3-Dipolar cycloaddition chemistry: Ed: Padwa, A., Wiley: New York, vol. 1, pp. 1-176.

Ikeda, S. et al. (1979). "The effects of ionization on micelle size of dimethyldodecylamine oxide," Journal of Colloid and Interface Science 70:448-455.

International Search Report mailed on Oct. 22, 2021, for PCT Application No. PCT/US2021/046432, filed on Aug. 18, 2021, 4 pages.

Jewett, J. C. et al. (2010). "Rapid Cu-Free Click Chemistry with Readily Synthesized Biarylazacyclooctynones," Journal of the American Chemical Society 132:3688-3690.

Kim, E. et al. (2019). "Biomedical applications of copper-free click chemistry: in vitro, in vivo, and ex vivo," Chem. Sci. 10:7835-7851.

Massaad-Massade, L. et al. (2018). "New Formulation for the Delivery of Oligonucleotides Using "Clickable" siRNA-Polyisoprenoid-Conjugated Nanoparticles: Application to Cancers Harboring Fusion Oncogenes," Bioconjugate Chemistry 29:1961-1972.

McLaughlin, J. M. et al. (2019). "Pneumococcal conjugate vaccine against serotype 3 pneumococcal pneumonia in adults: A systematic review and pooled analysis," Vaccine 37:6310-6316.

Ning, X. et al. (2010). "Protein modification by strain-promoted alkyne-nitrone cycloaddition," Angew. Chem. Int. Ed. 49:3065-3068.

Ning, X. et al. (2008). "Visualizing metabolically labeled glycoconjugates of living cells by copper-free and fast Huisgen cycloadditions," Angew. Chem. Int. Ed. 47:2253-2255.

Reinert, R.R. et al. (2010). "Pneumococcal disease caused by serotype 19A: review of the literature and implications for future vaccine development," Vaccine 28:4249-4259.

Schneider, D. et al. (2016). "Anionic surfactants enhance click reaction-mediated protein conjugation with ubiquitin," Bioorg. Med. Chem. 24:995-1001.

Shen, B.-Q. et al. (2012). "Conjugation site modulates the in vivo stability and therapeutic activity of antibody-drug conjugates," Nature Biotechnology 30:184-189.

Singh, G. et al. (2020). "Versatile Bispidine-Based Bifunctional Chelators for $^{64}Cu^{11}$-Labelling of Biomolecules," Chemistry A European Journal 26:1989-2001.

Slagle, C. J. et al. (2018). "Click Conjugation of Cloaked Peptide Ligands to Microbubbles," Bioconjugate Chemistry 29:1534-1543.

Tian, H. et al. (2015). "Micelle-enhanced biorthogonal labeling of genetically-encoded azido groups on the lipid-embedded surface of a GPCR," Chembiochem. 16:1314-1322.

Thirumurugan, P. et al. (2013). "Click chemistry for drug development and diverse chemical-biology applications," Chem. Rev. 113:4905-4979.

UniProt ID No. Q03945 (2023). "Invasin IpaB—Shigella Dysenteriae," 5 total pages.

UniProt ID No. P18011 (2023). "Invasin IpaB—Shigella Flexneri," 7 total pages.

UniProt ID No. Q8KXT4 (2023). "IpaB—Shigella Boydii," 4 total pages.

UniProt ID No. Q3YTQ2 (2023). "IpaB—Shigella Sonnei (strain Ss046)," 5 total pages.

Van Delft, P. et al. (2010). "Synthesis of oligoribonucleic acid conjugates using a cyclooctyne phosphoramidite," Organic Letters 12:5486-5489.

Written Opinion of the International Searching Authority mailed on Oct. 22, 2021, for PCT Application No. PCT/US2021/046432, filed on Aug. 18, 2021, 10 pages.

Zimmerman, E.S. et al. (2014). "Production of Site-Specific Antibody—Drug Conjugates Using Optimized Non-Natural Amino Acids in a Cell-Free Expression System," Bioconjugate Chemistry 25:351-361.

(56) References Cited

OTHER PUBLICATIONS

Extended European Search Report for EP Application No. 21859024.8, dated Sep. 17, 2024, 9 pages.
Stefanetti, G., et al., "Click chemistry compared to thiol chemistry for the synthesis of site-selective glycoconjugate vaccines using CRMas carrier protein," Glycoconjugate Journal, Chapman & Hall, Boston, vol. 37, No. 5, Jun. 13, 2020, 12 pages.

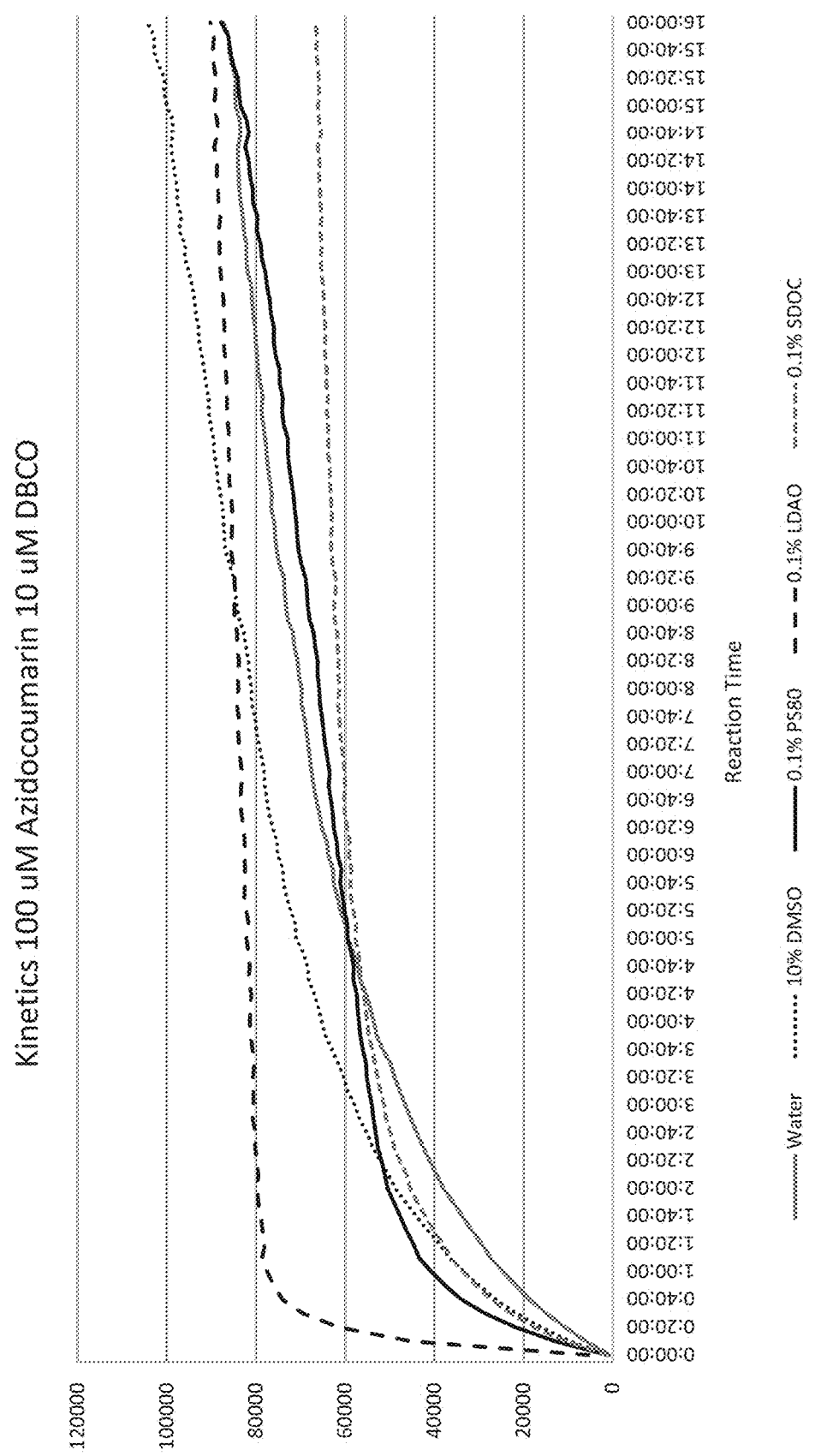

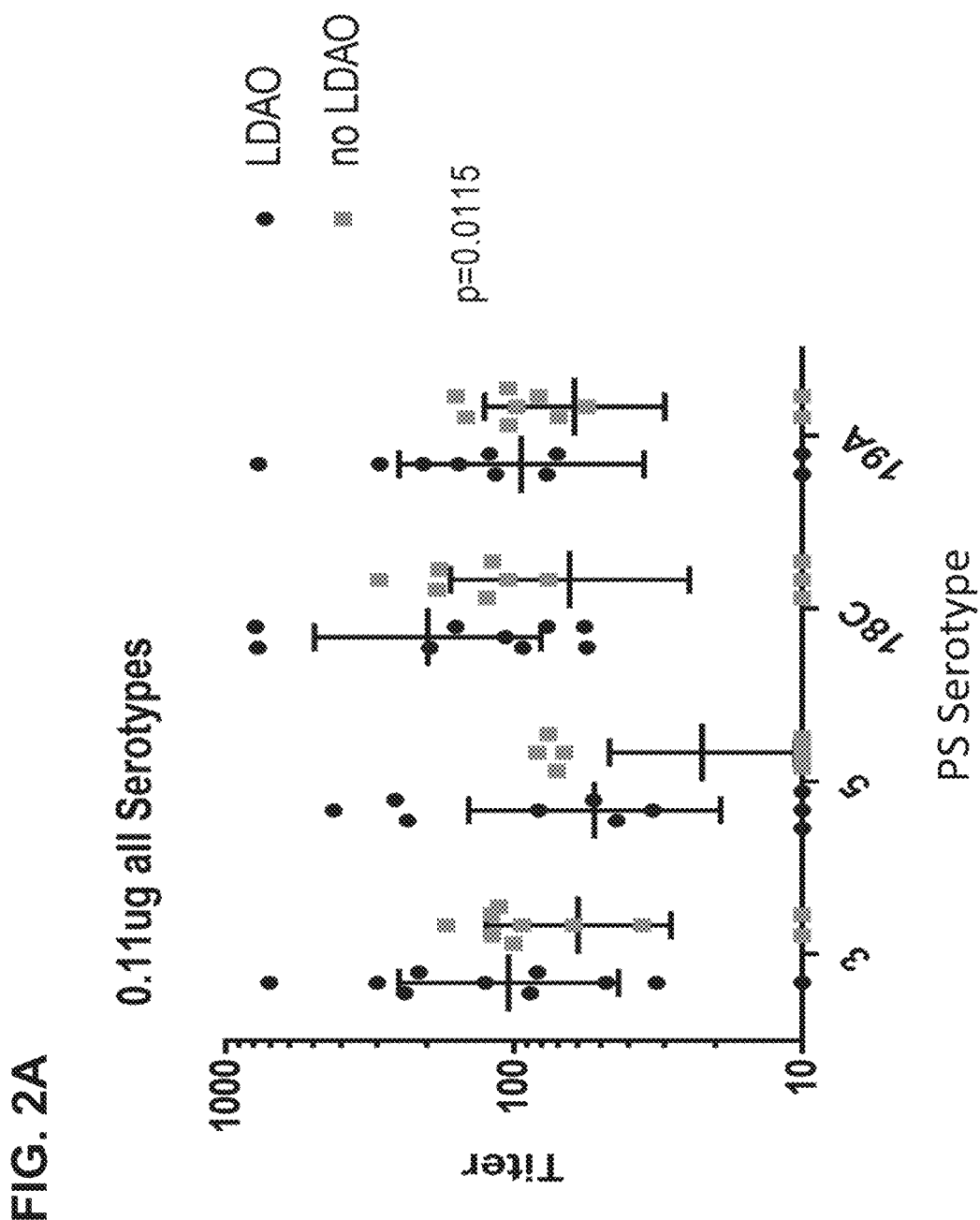

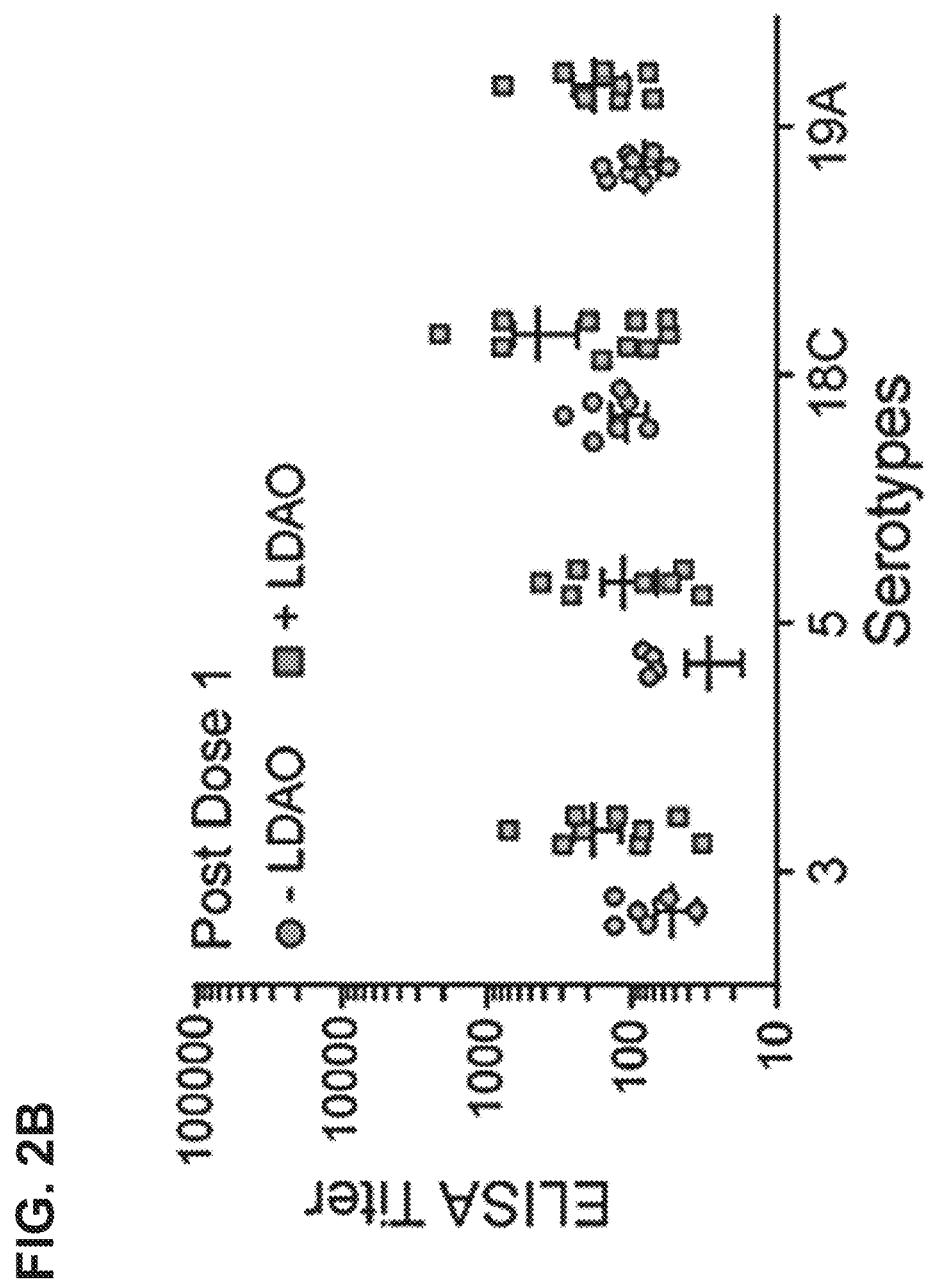

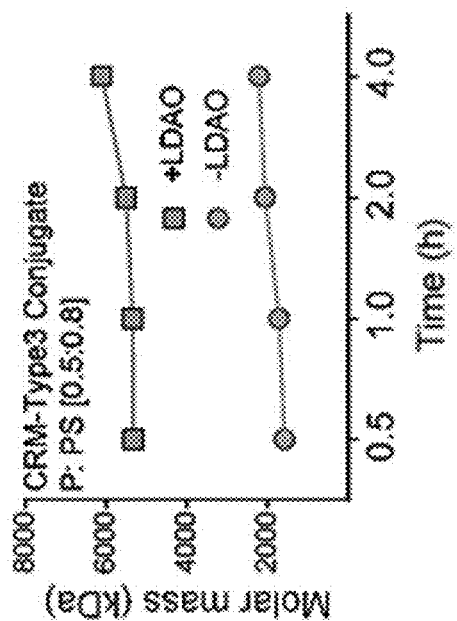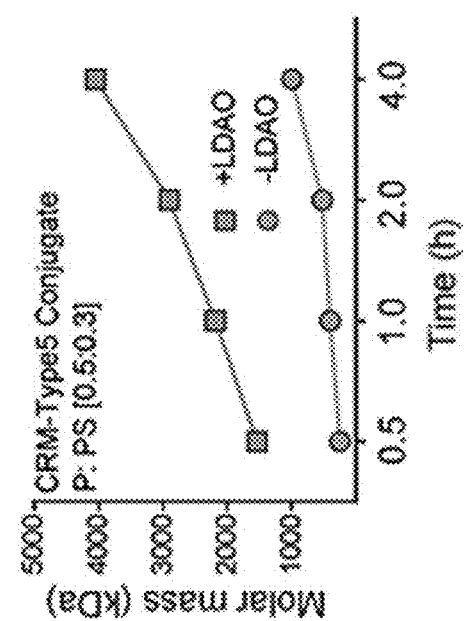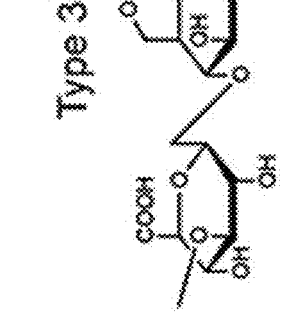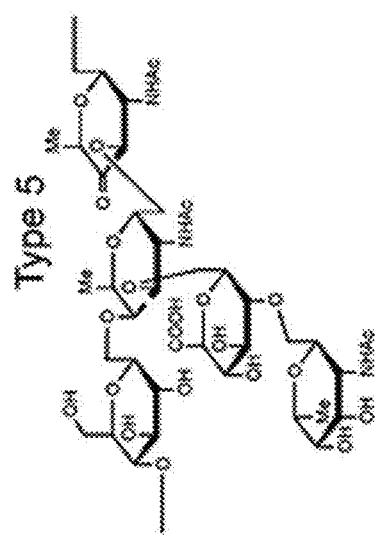
FIG. 4A
FIG. 4B

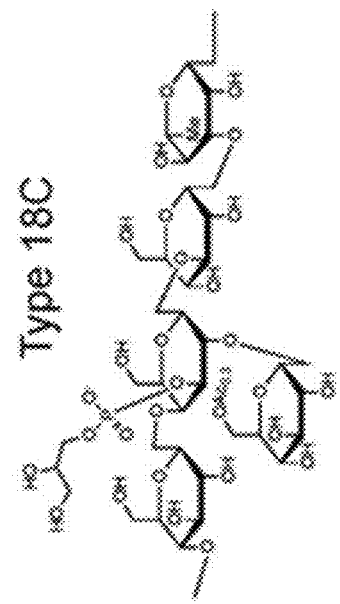
FIG. 4C
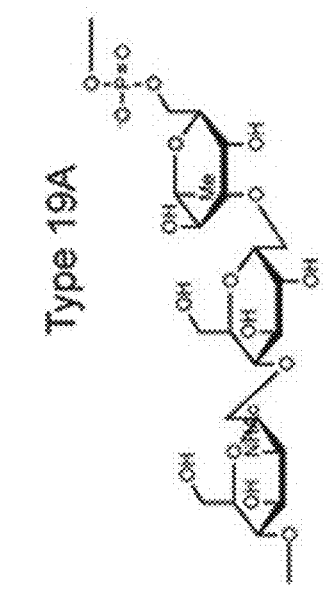
FIG. 4D
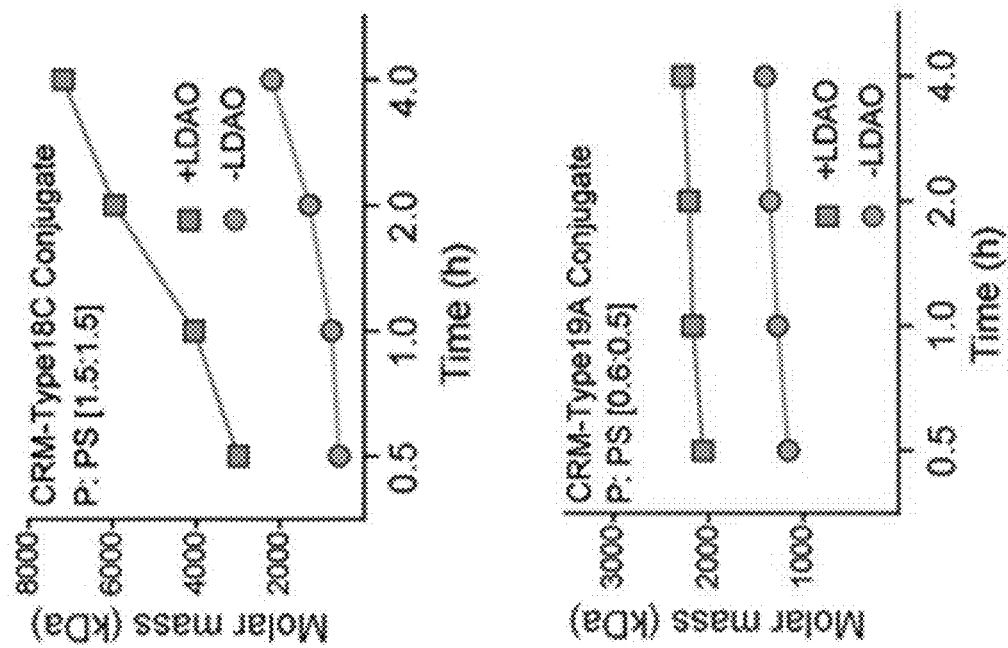

```
                           SEQUENCE LISTING

Sequence total quantity: 13
SEQ ID NO: 1             moltype = AA  length = 535
FEATURE                  Location/Qualifiers
REGION                   1..535
                         note = CRM197
source                   1..535
                         mol_type = protein
                         organism = unidentified
SEQUENCE: 1
GADDVVDSSK SFVMENFSSY HGTKPGYVDS IQKGIQKPKS GTQGNYDDDW KEFYSTDNKY   60
DAAGYSVDNE NPLSGKAGGV VKVTYPGLTK VLALKVDNAE TIKKELGLSL TEPLMEQVGT  120
EEFIKRFGDG ASRVVLSLPF AEGSSSVEYI NNWEQAKALS VELEINFETR GKRGQDAMYE  180
YMAQACAGNR VRRSVGSSLS CINLDWDVIR DKTKTKIESL KEHGPIKNKM SESPNKTVSE  240
EKAKQYLEEF HQTALEHPEL SELKTVTGTN PVFAGANYAA WAVNVAQVID SETADNLEKT  300
TAALSILPGI GSVMGIADGA VHHNTEEIVA QSIALSSLMV AQAIPLVGEL VDIGFAAYNF  360
VESIINLFQV VHNSYNRPAY SPGHKTQPFL HDGYAVSWNT VEDSIIRTGF QGESGHDIKI  420
TAENTPLPIA GVLLPTIPGK LDVNKSKTHI SVNGRKIRMR CRAIDGDVTF CRPKSPVYVG  480
NGVHANLHVA FHRSSSEKIH SNEISSDSIG VLGYQKTVDH TKVNSKLSLF FEIKS       535

SEQ ID NO: 2             moltype = AA  length = 536
FEATURE                  Location/Qualifiers
REGION                   1..536
                         note = CRM-pAMF6 mutant
VARIANT                  34
                         note = 2-amino-3-(4-(azidomethyl)phenyl)propanoic acid
VARIANT                  213
                         note = 2-amino-3-(4-(azidomethyl)phenyl)propanoic acid
VARIANT                  245
                         note = 2-amino-3-(4-(azidomethyl)phenyl)propanoic acid
VARIANT                  265
                         note = 2-amino-3-(4-(azidomethyl)phenyl)propanoic acid
VARIANT                  386
                         note = 2-amino-3-(4-(azidomethyl)phenyl)propanoic acid
VARIANT                  527
                         note = 2-amino-3-(4-(azidomethyl)phenyl)propanoic acid
source                   1..536
                         mol_type = protein
                         organism = synthetic construct
SEQUENCE: 2
MGADDVVDSS KSFVMENFSS YHGTKPGYVD SIQXGIQKPK SGTQGNYDDD WKEFYSTDNK   60
YDAAGYSVDN ENPLSGKAGG VVKVTYPGLT KVLALKVDNA ETIKKELGLS LTEPLMEQVG  120
TEEFIKRFGD GASRVVLSLP FAEGSSSVEY INNWEQAKAL SVELEINFET RGKRGQDAMY  180
EYMAQACAGN RVRRNSVGSSL SCINLDWDVI RDXTKTKIES LKEHGPIKNK MSESPNKTVS  240
EEKAXQYLEE FHQTALEHPE LSELXTVTGT NPVFAGANYA AWAVNVAQVI DSETADNLEK  300
TTAALSILPG IGSVMGIADG AVHHNTEEIV AQSIALSSLM VAQAIPLVGE LVDIGFAAYN  360
FVESIINLFQ VVHNSYNRPA YSPGHXTQPF LHDGYAVSWN TVEDSIIRTG FQGESGHDIK  420
ITAENTPLPI AGVLLPTIPG KLDVNKSKTH ISVNGRKIRM RCRAIDGDVT FCRPKSPVYV  480
GNGVHANLHV AFHRSSSEKI HSNEISSDSI GVLGYQKTVD HTKVNSXLSL FFEIKS      536

SEQ ID NO: 3             moltype = AA  length = 580
FEATURE                  Location/Qualifiers
REGION                   1..580
                         note = WT IpaB
source                   1..580
                         mol_type = protein
                         organism = unidentified
SEQUENCE: 3
MHNVNTTTTG LSLAKILAST ELGDNTIQAG NDAANKLFSL TIADLTANKN INTTNAHSTS   60
NILIPELKAP KSLNASSQLT LLIGNLIQIL GEKSLTALTN KITAWKSQQQ ARQQKNLEFS  120
DKINTLLSET EGLTRDYEKQ INKLKNADSK IKDLENKINQ IQTRLSELDP DSPEKKKLSR  180
EEIQLTIKKD AAVKDRTLIE QKTLSIHSKL TDKSMQLEKE IDSFSAFSNT ASAEQLSTQQ  240
KSLTGLASVT QLMATFIQLV GKNNEESLKN DLALFQSLQE SRKTEMERKS DEYAAEVRKA  300
EELNRVMGCV GKILGALLTI VSVVAAAFSG GASLALADVG LALMVTDAIV QAATGNSFME  360
QALNPIMKAV IEPLIKLLSD AFTKMLEGLG VDSKKAKMIG SILGAIAGAL VLVAAVVLVA  420
TVGKQAAAKL AENIGKIIGK TLTDLIPKFL KNFSSQLDDL ITNAVARLNK FLGAAGDEVI  480
SKQIISTHLN QAVLLGESVN SATQAGGSVA SAVFQNSAST NLADLTLSKY QVEQLSKYIS  540
EAIEKFGQLQ EVIADLLASM SNSQANRTDV AKAILQQTTA                        580
```

```
SEQ ID NO: 4              moltype = AA   length = 580
FEATURE                   Location/Qualifiers
REGION                    1..580
                          note = IpaB Mutant 1 K289/K368/K395
VARIANT                   289
                          note = X is a non-natural amino acid
VARIANT                   368
                          note = X is a non-natural amino acid
VARIANT                   395
                          note = X is a non-natural amino acid
source                    1..580
                          mol_type = protein
                          organism = synthetic construct
SEQUENCE: 4
MHNVNTTTTG LSLAKILAST ELGDNTIQAG NDAANKLFSL TIADLTANKN INTTNAHSTS    60
NILIPELKAP KSLNASSQLT LLIGNLIQIL GEKSLTALTN KITAWKSQQQ ARQQKNLEFS   120
DKINTLLSET EGLTRDYEKQ INKLKNADSK IKDLENKINQ IQTRLSELDP DSPEKKKLSR   180
EEIQLTIKKD AAVKDRTLIE QKTLSIHSKL TDKSMQLEKE IDSFSAFSNT ASAEQLSTQQ   240
KSLTGLASVT QLMATFIQLV GKNNEESLKN DLALFQSLQE SRKTEMERXS DEYAAEVRKA   300
EELNRVMGCV GKILGALLTI VSVVAAAFSG GASLALADVG LALMVTDAIV QAATGNSFME   360
QALNPIMXAV IEPLIKLLSD AFTKMLEGLG VDSKXAKMIG SILGAIAGAL VLVAAVVLVA   420
TVGKQAAAKL AENIGKIIGK TLTDLIPKFL KNFSSQLDDL ITNAVARLNK FLGAAGDEVI   480
SKQIISTHLN QAVLLGESVN SATQAGGSVA SAVFQNSAST NLADLTLSKY QVEQLSKYIS   540
EAIEKFGQLQ EVIADLLASM SNSQANRTDV AKAILQQTTA                         580

SEQ ID NO: 5              moltype = AA   length = 580
FEATURE                   Location/Qualifiers
REGION                    1..580
                          note = IpaB Mutant 2 K299/K395/K436
VARIANT                   299
                          note = X is a non-natural amino acid
VARIANT                   395
                          note = X is a non-natural amino acid
VARIANT                   436
                          note = X is a non-natural amino acid
source                    1..580
                          mol_type = protein
                          organism = synthetic construct
SEQUENCE: 5
MHNVNTTTTG LSLAKILAST ELGDNTIQAG NDAANKLFSL TIADLTANKN INTTNAHSTS    60
NILIPELKAP KSLNASSQLT LLIGNLIQIL GEKSLTALTN KITAWKSQQQ ARQQKNLEFS   120
DKINTLLSET EGLTRDYEKQ INKLKNADSK IKDLENKINQ IQTRLSELDP DSPEKKKLSR   180
EEIQLTIKKD AAVKDRTLIE QKTLSIHSKL TDKSMQLEKE IDSFSAFSNT ASAEQLSTQQ   240
KSLTGLASVT QLMATFIQLV GKNNEESLKN DLALFQSLQE SRKTEMERKS DEYAAEVRXA   300
EELNRVMGCV GKILGALLTI VSVVAAAFSG GASLALADVG LALMVTDAIV QAATGNSFME   360
QALNPIMKAV IEPLIKLLSD AFTKMLEGLG VDSKXAKMIG SILGAIAGAL VLVAAVVLVA   420
TVGKQAAAKL AENIGKIIGK TLTDLIPKFL KNFSSQLDDL ITNAVARLNK FLGAAGDEVI   480
SKQIISTHLN QAVLLGESVN SATQAGGSVA SAVFQNSAST NLADLTLSKY QVEQLSKYIS   540
EAIEKFGQLQ EVIADLLASM SNSQANRTDV AKAILQQTTA                         580

SEQ ID NO: 6              moltype = AA   length = 580
FEATURE                   Location/Qualifiers
REGION                    1..580
                          note = IpaB Mutant 3 K299/K368/K395
VARIANT                   299
                          note = X is a non-natural amino acid
VARIANT                   368
                          note = X is a non-natural amino acid
VARIANT                   395
                          note = X is a non-natural amino acid
source                    1..580
                          mol_type = protein
                          organism = synthetic construct
SEQUENCE: 6
MHNVNTTTTG LSLAKILAST ELGDNTIQAG NDAANKLFSL TIADLTANKN INTTNAHSTS    60
NILIPELKAP KSLNASSQLT LLIGNLIQIL GEKSLTALTN KITAWKSQQQ ARQQKNLEFS   120
DKINTLLSET EGLTRDYEKQ INKLKNADSK IKDLENKINQ IQTRLSELDP DSPEKKKLSR   180
EEIQLTIKKD AAVKDRTLIE QKTLSIHSKL TDKSMQLEKE IDSFSAFSNT ASAEQLSTQQ   240
KSLTGLASVT QLMATFIQLV GKNNEESLKN DLALFQSLQE SRKTEMERKS DEYAAEVRXA   300
EELNRVMGCV GKILGALLTI VSVVAAAFSG GASLALADVG LALMVTDAIV QAATGNSFME   360
QALNPIMXAV IEPLIKLLSD AFTKMLEGLG VDSKXAKMIG SILGAIAGAL VLVAAVVLVA   420
TVGKQAAAKL AENIGKIIGK TLTDLIPKFL KNFSSQLDDL ITNAVARLNK FLGAAGDEVI   480
SKQIISTHLN QAVLLGESVN SATQAGGSVA SAVFQNSAST NLADLTLSKY QVEQLSKYIS   540
EAIEKFGQLQ EVIADLLASM SNSQANRTDV AKAILQQTTA                         580

SEQ ID NO: 7              moltype = AA   length = 580
FEATURE                   Location/Qualifiers
REGION                    1..580
```

|  |  |  |
|---|---|---|
| VARIANT | 289 | |
| | note = IpaB Mutant 4 K289/K368/K395/K436 | |
| | note = X is a non-natural amino acid | |
| VARIANT | 368 | |
| | note = X is a non-natural amino acid | |
| VARIANT | 395 | |
| | note = X is a non-natural amino acid | |
| VARIANT | 436 | |
| | note = X is a non-natural amino acid | |
| source | 1..580 | |
| | mol_type = protein | |
| | organism = synthetic construct | |

SEQUENCE: 7
```
MHNVNTTTTG LSLAKILAST ELGDNTIQAG NDAANKLFSL TIADLTANKN INTTNAHSTS   60
NILIPELKAP KSLNASSQLT LLIGNLIQIL GEKSLTALTN KITAWKSQQQ ARQQKNLEFS  120
DKINTLLSET EGLTRDYEKQ INKLKNADSK IKDLENKINQ IQTRLSELDP DSPEKKKLSR  180
EEIQLTIKKD AAVKDRTLIE QKTLSIHSKL TDKSMQLEKE IDSFSAFSNT ASAEQLSTQQ  240
KSLTGLASVT QLMATFIQLV GKNNEESLKN DLALFQSLQE SRKTEMERXS DEYAAEVRKA  300
EELNRVMGCV GKILGALLTI VSVVAAAFSG GASLALADVG LALMVTDAIV QAATGNSFME  360
QALNPIMXAV IEPLIKLLSD AFTKMLEGLG VDSKXAKMIG SILGAIAGAL VLVAAVVLVA  420
TVGKQAAAKL AENIGXIIGK TLTDLIPKFL KNFSSQLDDL ITNAVARLNK FLGAAGDEVI  480
SKQIISTHLN QAVLLGESVN SATQAGGSVA SAVFQNSAST NLADLTLSKY QVEQLSKYIS  540
EAIEKFGQLQ EVIADLLASM SNSQANRTDV AKAILQQTTA                       580
```

|  |  |  |
|---|---|---|
| SEQ ID NO: 8 | moltype = AA  length = 580 | |
| FEATURE | Location/Qualifiers | |
| REGION | 1..580 | |
| | note = IpaB Mutant 5 K299/K395/K436/K470 | |
| VARIANT | 299 | |
| | note = X is a non-natural amino acid | |
| VARIANT | 395 | |
| | note = X is a non-natural amino acid | |
| VARIANT | 436 | |
| | note = X is a non-natural amino acid | |
| VARIANT | 470 | |
| | note = X is a non-natural amino acid | |
| source | 1..580 | |
| | mol_type = protein | |
| | organism = synthetic construct | |

SEQUENCE: 8
```
MHNVNTTTTG LSLAKILAST ELGDNTIQAG NDAANKLFSL TIADLTANKN INTTNAHSTS   60
NILIPELKAP KSLNASSQLT LLIGNLIQIL GEKSLTALTN KITAWKSQQQ ARQQKNLEFS  120
DKINTLLSET EGLTRDYEKQ INKLKNADSK IKDLENKINQ IQTRLSELDP DSPEKKKLSR  180
EEIQLTIKKD AAVKDRTLIE QKTLSIHSKL TDKSMQLEKE IDSFSAFSNT ASAEQLSTQQ  240
KSLTGLASVT QLMATFIQLV GKNNEESLKN DLALFQSLQE SRKTEMERKS DEYAAEVRXA  300
EELNRVMGCV GKILGALLTI VSVVAAAFSG GASLALADVG LALMVTDAIV QAATGNSFME  360
QALNPIMKAV IEPLIKLLSD AFTKMLEGLG VDSKXAKMIG SILGAIAGAL VLVAAVVLVA  420
TVGKQAAAKL AENIGKIIGK TLTDLIPKFL KNFSSQLDDL ITNAVARLNX FLGAAGDEVI  480
SKQIISTHLN QAVLLGESVN SATQAGGSVA SAVFQNSAST NLADLTLSKY QVEQLSKYIS  540
EAIEKFGQLQ EVIADLLASM SNSQANRTDV AKAILQQTTA                       580
```

|  |  |  |
|---|---|---|
| SEQ ID NO: 9 | moltype = AA  length = 580 | |
| FEATURE | Location/Qualifiers | |
| REGION | 1..580 | |
| | note = IpaB Mutant 6 K299/K368/K395/K436 | |
| VARIANT | 299 | |
| | note = X is a non-natural amino acid | |
| VARIANT | 368 | |
| | note = X is a non-natural amino acid | |
| VARIANT | 395 | |
| | note = X is a non-natural amino acid | |
| VARIANT | 436 | |
| | note = X is a non-natural amino acid | |
| source | 1..580 | |
| | mol_type = protein | |
| | organism = synthetic construct | |

SEQUENCE: 9
```
MHNVNTTTTG LSLAKILAST ELGDNTIQAG NDAANKLFSL TIADLTANKN INTTNAHSTS   60
NILIPELKAP KSLNASSQLT LLIGNLIQIL GEKSLTALTN KITAWKSQQQ ARQQKNLEFS  120
DKINTLLSET EGLTRDYEKQ INKLKNADSK IKDLENKINQ IQTRLSELDP DSPEKKKLSR  180
EEIQLTIKKD AAVKDRTLIE QKTLSIHSKL TDKSMQLEKE IDSFSAFSNT ASAEQLSTQQ  240
KSLTGLASVT QLMATFIQLV GKNNEESLKN DLALFQSLQE SRKTEMERKS DEYAAEVRXA  300
EELNRVMGCV GKILGALLTI VSVVAAAFSG GASLALADVG LALMVTDAIV QAATGNSFME  360
QALNPIMXAV IEPLIKLLSD AFTKMLEGLG VDSKXAKMIG SILGAIAGAL VLVAAVVLVA  420
TVGKQAAAKL AENIGXIIGK TLTDLIPKFL KNFSSQLDDL ITNAVARLNK FLGAAGDEVI  480
SKQIISTHLN QAVLLGESVN SATQAGGSVA SAVFQNSAST NLADLTLSKY QVEQLSKYIS  540
EAIEKFGQLQ EVIADLLASM SNSQANRTDV AKAILQQTTA                       580
```

|  |  |
|---|---|
| SEQ ID NO: 10 | moltype = AA  length = 834 |

```
FEATURE                 Location/Qualifiers
source                  1..834
                        mol_type = protein
                        organism = Streptococcus pyogenes
SEQUENCE: 10
MHHHHHHSGS ENLYFQGQVK ADDRASGETK ASNTHDDSLP KPETIQEAKA TIDAVEKTLS    60
QQKAELTELA TALTKTTAEI NHLKEQQDNE QKALTSAQEI YTNTLASSEE TLLAQGAEHQ   120
RELTATETEL HNAQADQHSK ETALSEQKAS ISAETTRAQD LVEQVKTSEQ NIAKLNAMIS   180
NPDAITKAAQ TANDNTKALS SELEKAKADL ENQKAVKKQ  LTEELAAQKA ALAEKEAELS   240
RLKSSAPSTQ DSIVGNNTMK APQGYPLEEL KKLEASGYIG SASYNNYYKE HADQIIAKAS   300
PGNQLNQYQD IPADRNRFVD PDNLTPEVQN ELAQFAAHMI NSVRRQLGLP PVTVTAGSQE   360
FARLLSTSYK KTHGNTRPSF VYGQPGVSGH YGVGPHDKTI IEDSAGASGL IRNDDNMYEN   420
IGAFNDVHTV NGIKRGIYDS IKYMLFTDHL HGNTYGHAIN FLRVDKHNPN APVYLGFSTS   480
NVGSLNEHFV MFPESNIANH QRFNKTPIKA VGSTKDYAQR VGTVSDTIAA IKGKVSSLEN   540
RLSAIHQEAD IMAAQAKVSQ LQGKLASTLK QSDSLNLQVR QLNDTKGSLR TELLAAKAKQ   600
AQLEATRDQS LAKLASLKAA LHQTEALAEQ AAARVTALVA KKAHLQYLRD FKLNPNRLQV   660
IRERIDNTKQ DLAKTTSSLL NAQEALAALQ AKQSSLEATI ATTEHQLTLL KTLANEKEYR   720
HLDEDIATVP DLQVAPPLTG VKPLSYSKID TTPLVQEMVK ETKQLLEASA RLAAENTSLV   780
AEALVGQTSE MVASNAIVSK ITSSITQPSS KTSYGSGSST TSNLISDVDE STQR         834

SEQ ID NO: 11           moltype = AA  length = 251
FEATURE                 Location/Qualifiers
source                  1..251
                        mol_type = protein
                        organism = Haemophilus influenzae
SEQUENCE: 11
GCSSHSSNMA NTQMKSDKII IAHRGASGYL PEHTLESKAL AFAQQADYLE QDLAMTKDGR    60
LVVIHDHFLD GLTDVAKKFP HRHRKDGRYY VIDFTLKEIQ SLEMTENFET KDGKQAQVYP   120
NRFPLWKSHF RIHTFEDEIE FIQGLEKSTG KKVGIYPEIK APWFHHQNGK DIAAETLKVL   180
KKYGYDKKTD MVYLQTFDFN ELKRIKTELL PQMGMDLKLV QLIAYTDWKE TQEKDPKGYW   240
VNYNYDWMFK P                                                       251

SEQ ID NO: 12           moltype = AA  length = 817
FEATURE                 Location/Qualifiers
REGION                  1..817
                        note = SPYAD [33-849 FRAGMENT] WT W/O LEADER
source                  1..817
                        mol_type = protein
                        organism = synthetic construct
SEQUENCE: 12
QVKADDRASG ETKASNTHDD SLPKPETIQE AKATIDAVEK TLSQQKAELT ELATALTKTT    60
AEINHLKEQQ DNEQKALTSA QEIYTNTLAS SEETLLAQGA EHQRELTATE TELHNAQADQ   120
HSKETALSEQ KASISAETTR AQDLVEQVKT SEQNIAKLNA MISNPDAITK AAQTANDNTK   180
ALSSELEKAK ADLENQKAKV KKQLTEELAA QKAALAEKEA ELSRLKSSAP STQDSIVGNN   240
TMKAPQGYPL EELKKLEASG YIGSASYNNY YKEHADQIIA KASPGNQLNQ YQDIPADRNR   300
FVDPDNLTPE VQNELAQFAA HMINSVRRQL GLPPVTVTAG SQEFARLLST SYKKTHGNTR   360
PSFVYGQPGV SGHYGVGPHD KTIIEDSAGA SGLIRNDDNM YENIGAFNDV HTVNGIKRGI   420
YDSIKYMLFT DHLHGNTYGH AINFLRVDKH NPNAPVYLGF STSNVGSLNE HFVMFPESNI   480
ANHQRFNKTP IKAVGSTKDY AQRVGTVSDT IAAIKGKVSS LENRLSAIHQ EADIMAAQAK   540
VSQLQGKLAS TLKQSDSLNL QVRQLNDTKG SLRTELLAAK AKQAQLEATR DQSLAKLASL   600
KAALHQTEAL AEQAAARVTA LVAKKAHLQY LRDFKLNPNR LQVIRERIDN TKQDLAKTTS   660
SLLNAQEALA ALQAKQSSLE ATIATTEHQL TLLKTLANEK EYRHLDEDIA TVPDLQVAPP   720
LTGVKPLSYS KIDTTPLVQE MVKETKQLLE ASARLAAENT SLVAEALVGQ TSEMVASNAI   780
VSKITSSITQ PSSKTSYGSG SSTTSNLISD VDESTQR                            817

SEQ ID NO: 13           moltype = AA  length = 818
FEATURE                 Location/Qualifiers
REGION                  1..818
                        note = SPYAD [33-849 FRAGMENT] NNAA (E.G., PAMF) W/O
                         LEADER, WITH G OVERHANG FROM CLEAVAGE
VARIANT                 33
                        note = X is a non-natural amino acid
VARIANT                 256
                        note = X is a non-natural amino acid
VARIANT                 355
                        note = X is a non-natural amino acid
VARIANT                 626
                        note = X is a non-natural amino acid
source                  1..818
                        mol_type = protein
                        organism = synthetic construct
SEQUENCE: 13
GQVKADDRAS GETKASNTHD DSLPKPETIQ EAXATIDAVE KTLSQQKAEL TELATALTKT    60
TAEINHLKEQ QDNEQKALTS AQEIYTNTLA SSEETLLAQG AEHQRELTAT ETELHNAQAD   120
QHSKETALSE QKASISAETT RAQDLVEQVK TSEQNIAKLN AMISNPDAIT KAAQTANDNT   180
KALSSELEKA KADLENQKAK VKKQLTEELA AQKAALAEKE AELSRLKSSA PSTQDSIVGN   240
NTMKAPQGYP LEELKXLEAS GYIGSASYNN YYKEHADQII AKASPGNQLN QYQDIPADRN   300
RFVDPDNLTP EVQNELAQFA AHMINSVRRQ LGLPPVTVTA GSQEFARLLS TSYKXTHGNT   360
RPSFVYGQPG VSGHYGVGPH DKTIIEDSAG ASGLIRNDDN MYENIGAFND VHTVNGIKRG   420
```

| | | | | | |
|---|---|---|---|---|---|
| IYDSIKYMLF | TDHLHGNTYG | HAINFLRVDK | HNPNAPVYLG | FSTSNVGSLN | EHFVMFPESN | 480
| IANHQRFNKT | PIKAVGSTKD | YAQRVGTVSD | TIAAIKGKVS | SLENRLSAIH | QEADIMAAQA | 540
| KVSQLQGKLA | STLKQSDSLN | LQVRQLNDTK | GSLRTELLAA | KAKQAQLEAT | RDQSLAKLAS | 600
| LKAALHQTEA | LAEQAAARVT | ALVAKXAHLQ | YLRDFKLNPN | RLQVIRERID | NTKQDLAKTT | 660
| SSLLNAQEAL | AALQAKQSSL | EATIATTEHQ | LTLLKTLANE | KEYRHLDEDI | ATVPDLQVAP | 720
| PLTGVKPLSY | SKIDTTPLVQ | EMVKETKQLL | EASARLAAEN | TSLVAEALVG | QTSEMVASNA | 780
| IVSKITSSIT | QPSSKTSYGS | GSSTTSNLIS | DVDESTQR | | | 818

CARRIER-PROTEIN POLYSACCHARIDE CONJUGATION METHODS

CROSS-REFERENCE TO RELATED APPLICATIONS

This application is a continuation of International Application No. PCT/US2021/046432, filed Aug. 18, 2021, which claims the benefit of U.S. Provisional Application No. 63/067,752, filed Aug. 19, 2020, the disclosure of which is hereby incorporated by reference in its entirety.

DESCRIPTION OF THE TEXT FILE SUBMITTED ELECTRONICALLY

The sequence listing associated with this application is provided in text format in lieu of a paper copy, and is hereby incorporated by reference into the specification. The name of the text file containing the sequence listing is STRO_012_01US_SeqList_ST26.xml. The text file is 36,449 bytes, was created on Feb. 17, 2023, and is being submitted electronically via Patent Center.

TECHNICAL FIELD

The present disclosure relates generally to novel methods of effecting click chemistry reactions.

SUMMARY

In some aspects are methods of preparing a heteroaryl-containing compound, the methods comprising contacting an azide compound with an alkyne compound in the presence of lauryldimethylamine oxide (LDAO), water, and DMSO to form the heteroaryl-containing compound,
 wherein the LDAO is at a concentration of up to 2% v/v;
 wherein the azide compound is a compound of formula (I)

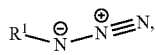
(I)

wherein the alkyne compound is a compound of formula (II) or (III)

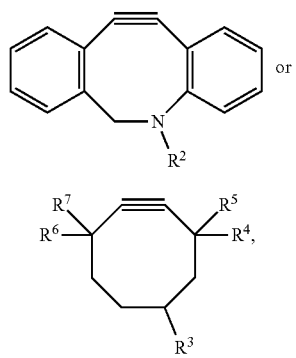

wherein
 $R^1$, $R^2$, and $R^3$ are independently selected from the group consisting of substituted or unsubstituted alkyl, substituted or unsubstituted alkenyl, substituted or unsubstituted alkynyl, substituted or unsubstituted alkoxy, substituted or unsubstituted cycloalkyl, substituted or unsubstituted aryl, substituted or unsubstituted heteroaryl, substituted or unsubstituted heterocyclyl, $-(CH_2)_a-C(O)R^{1a}$, $-(CH_2)_a-C(O)OR^{1a}$, $-(CH_2)_a-C(O)N(R^{1a})_2$, $-(CH_2)_a-C(O)NHCH(R^{1a})_2$, $-(CH_2)_a-N(R^{1a})_2$; wherein a is integer from zero to 10; wherein each $R^{1a}$ is independently hydrogen, substituted or unsubstituted alkyl, substituted or unsubstituted alkenyl, substituted or unsubstituted alkoxy, substituted or unsubstituted cycloalkyl, substituted or unsubstituted aryl, substituted or unsubstituted heteroaryl, and substituted or unsubstituted heterocyclyl; or
 $R^1$ is a first polypeptide comprising at least one non-natural amino acid residue (nnAAr) of formula (IV)

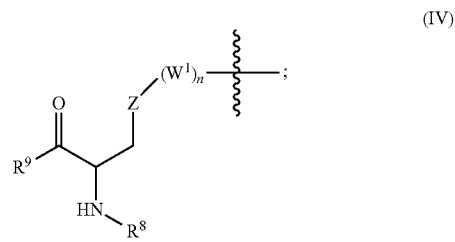
(IV)

wherein Z is absent or a 5-membered or 6-membered aryl or heteroaryl ring; $W^1$ is selected from the group consisting of $C_1$-$C_{10}$ alkylene, $-NH-$, $-O-$ and $-S-$; n is zero or 1; $R^8$ is H or an amino add residue of the first polypeptide, and $R^9$ is OH or an amino acid residue of the first polypeptide; and
 $R^2$ and $R^3$ are independently -$L^1$-$X^1$;
wherein
 $X^1$ is a polysaccharide or a second polypeptide;
 $L^1$ is optional, and when present is a linker selected from the group consisting of substituted or unsubstituted alkylene, substituted or unsubstituted alkenylene, $-O-$, $-O-$(substituted or unsubstituted alkylene)-, -(substituted or unsubstituted alkylene)-O-, $-O-$(substituted or unsubstituted alkylene)-C(O)$-Y^1-$, $-C(O)$-(substituted or unsubstituted alkylene)-NH$-Y^2-$, $-C(O)$-(substituted or unsubstituted alkylene)-C(O)$-$, $-C(O)$-(substituted or unsubstituted alkylene)-NH$-C(O)-(CH_2-CH_2-O)_n$-(substituted or unsubstituted alkylene)-NH$-$, $-C(O)$-(substituted or unsubstituted alkylene)-NH$-$, $-C(O)$-(substituted or unsubstituted alkylene)-NH$-C(O)-(CH_2-CH_2-O)_n$-(substituted or unsubstituted alkylene)-C(O)$-$, $-C(O)$-(substituted or unsubstituted alkylene)-C(O)$-$NH-(substituted or unsubstituted alkylene)-, $-C(O)-$, $-C(O)$-(substituted or unsubstituted alkylene)-, -(substituted or unsubstituted alkylene)-C(O)$-$, $-C(O)N(R^{L1})-$, $-C(O)N(R^{L1})$-(substituted or unsubstituted alkylene)-, -(substituted or unsubstituted alkylene)-C(O)N($R^{L1}$), -(substituted or unsubstituted alkylene)-C(O)$N^{L1}$-(substituted or unsubstituted alkylene)-, $-OC(O)N(R^{L1})-$, $-OC(O)N(R^{L1})$-(substituted or unsubstituted alkylene)-, -(substituted or unsubstituted alkylene)-OC(O)N($R^{L1}$)$-$, $-N(R^{L1})C(O)-$, $-NR^{L1}C(O)$-(substituted or unsubstituted alkylene)-, -(substituted or unsubstituted alkylene)-$NR^{L1}C(O)-$, $-S-$, $-S$-(substituted or unsubstituted alkylene)-, $-S(O)_k-$, $-S(O)_k$(alkylene or substituted alkylene)-, —C(S)—, —C(S)-(substituted or unsubstituted alkylene)-, —CSN($R^{L1}$)—, —CSN($R^{L1}$)-(substituted or unsubstituted alkylene)-, —N($R^{L1}$)C(O)O—, -(substituted or unsubstituted alkylene)-O—N=$CR^{L1}$—, -(substituted or unsubstituted alkylene)-S(O)$_k$-(substituted or unsubstituted alkylene)-S—, -(substituted or unsubstituted alkylene)-S—S—, —S(O)$_k$N($R^{L1}$)—, —N($R^{L1}$)C(O)N($R^{L1}$)—, —N($R^{L1}$)C(S)N($R^{L1}$)—, —N($R^{L1}$)S(O)$_k$N($R^{L1}$)—, —N($R^{L1}$)—N=, —C($R^{L1}$)=N—, —C($R^{L1}$)=N—N($R^{L1}$)—, —C($R^{L1}$)=N—N=, —C($R^{L1}$)$_2$—N=N—, and —C($R^{L1}$)$_2$—N($R^{L1}$)—N($R^{L1}$)—; wherein the bond on the left side of $L^1$, as drawn, is bound to the 8-membered ring of the compound of formula (II) or the compound of formula (III) and the bond on the right side of the $L^1$, as drawn, is bound to $X^1$;

$Y^1$ is a bond, —NH—, —O—, —S—, —NH($Y^{1a}$)—, —O($Y^{1a}$)— or —S($Y^{1a}$)—;

$Y^2$ is a bond, —C(=O)—, —S(=O)$_2$—, —C(=O)$Y^{2a}$—, —S(=O)$_2Y^{2a}$;

$Y^{1a}$ and $Y^{2a}$ are each independently $Y^3$ or $Y^3$NH—

$Y^3$ is substituted or unsubstituted $C_{1-10}$alkyl or —(CH$_2$CH$_2$O)$_{1-10}$—; and n is an integer from 1 to 30;

k is 1, 2, or 3;

each $R^{L1}$ is independently hydrogen or substituted or unsubstituted alkyl; and $R^4$, $R^5$, $R^6$, and $R^7$ are each independently hydrogen, halo, or substituted or unsubstituted alkyl.

In some aspects are a heteroaryl-containing bioconjugate comprising a polypeptide and antigen of any one of Formulae XIII, XIV, XV, or XVI:

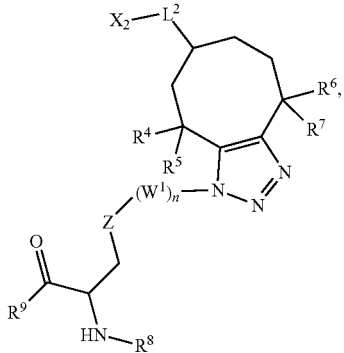

(XIII)

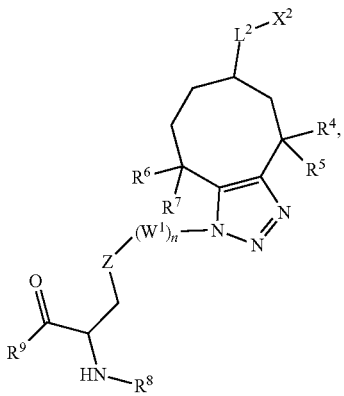

(XIV)

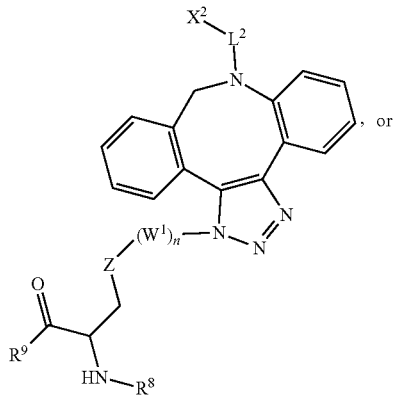

(XV)

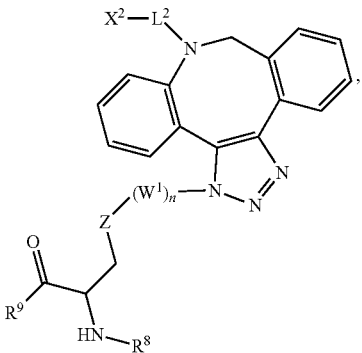

(XVI)

wherein the first polypeptide comprises at least one nnAAr comprising an azido moiety, of Formula (I'):

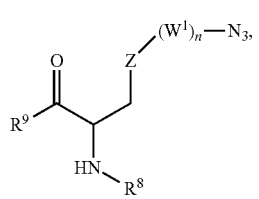

(I')

wherein Z is absent or a 5-membered or 6-membered aryl or heteroaryl ring; $W^1$ is selected from the group consisting of $C_1$-$C_{10}$ alkylene, —NH—, —O— and —S—; n is zero or 1; $R^8$ is H or an amino add residue of the first polypeptide, and $R^9$ is OH or an amino acid residue of the first polypeptide, wherein at least one of $R^8$ and $R^9$ is an amino acid residue of the first polypeptide;

wherein the azido moiety of the nnAAr is conjugated to an alkyne by contacting the nnAAr and the alkyne in the presence of LDAO, the alkyne is formula II'-A, III'-A, or III'-B:

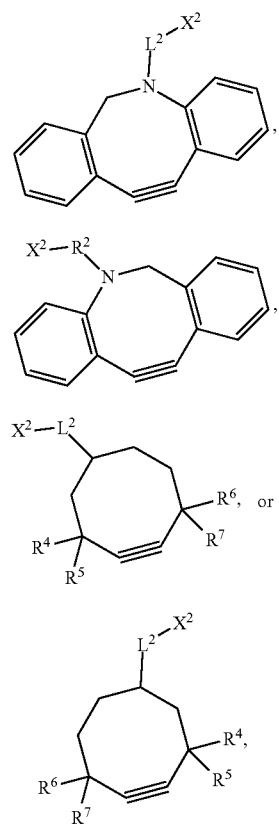

wherein
X² is an antigen comprising a polysaccharide or second polypeptide,
L² is optional, and when present is a linker selected from the group consisting of substituted or unsubstituted alkylene, substituted or unsubstituted alkenylene, —O—, —O-(substituted or unsubstituted alkylene)-, -(substituted or unsubstituted alkylene)-O—, —O-(substituted or unsubstituted alkylene)-C(O)—Y¹—, —C(O)-(substituted or unsubstituted alkylene)-NH—Y²—, —C(O)-(substituted or unsubstituted alkylene)-C(O)—, —C(O)-(substituted or unsubstituted alkylene)-NH—C(O)—(CH₂—CH₂—O)$_n$-(substituted or unsubstituted alkylene)-NH—, —C(O)-(substituted or unsubstituted alkylene)-NH—, —C(O)-(substituted or unsubstituted alkylene)-NH—C(O)—(CH₂—CH₂—O)$_n$-(substituted or unsubstituted alkylene)-C(O)—, —C(O)-(substituted or unsubstituted alkylene)-C(O)—NH-(substituted or unsubstituted alkylene)-, —C(O)—, —C(O)-(substituted or unsubstituted alkylene)-, -(substituted or unsubstituted alkylene)-C(O)—, —C(O)N(R$^{L1}$)—, —C(O)N(R$^{L1}$)-(substituted or unsubstituted alkylene)-, -(substituted or unsubstituted alkylene)-C(O)N(R$^{L1}$), -(substituted or unsubstituted alkylene)-C(O)NR$^{L1}$-(substituted or unsubstituted alkylene)-, —OC(O)N(R$^{L1}$)—, —OC(O)N(R$^{L1}$)-(substituted or unsubstituted alkylene)-, -(substituted or unsubstituted alkylene)-OC(O)N(R$^{L1}$)—, —N(R$^{L1}$)C(O)—,
—NR$^{L1}$C(O)-(substituted or unsubstituted alkylene)-, -(substituted or unsubstituted alkylene)-NR$^{L1}$C(O)—,
—S—, —S-(substituted or unsubstituted alkylene)-, —S(O)$_k$—, —S(O)$_k$(alkylene or substituted alkylene)-, —C(S)—, —C(S)-(substituted or unsubstituted alkylene)-, —CSN(R$^{L1}$)—, —CSN(R$^{L1}$)-(substituted or unsubstituted alkylene)-, —N(R$^{L1}$)C(O)O—, -(substituted or unsubstituted alkylene)-O—N=CR$^{L1}$—, -(substituted or unsubstituted alkylene)-S(O)$_k$— (substituted or unsubstituted alkylene)-S—, -(substituted or unsubstituted alkylene)-S—S—, —S(O)$_k$N(R$^{L1}$)—, —N(R$^{L1}$)C(O)N(R$^{L1}$)—, —N(R$^{L1}$)C(S)N(R$^{L1}$)—, —N(R$^{L1}$)S(O)$_k$N(R$^{L1}$)—, —N(R$^{L1}$)—N=, —C(R$^{L1}$)=N—, —C(R$^{L1}$)=N—N(R$^{L1}$)—, —C(R$^{L1}$)=N—N=, —C(R$^{L1}$)₂—N=N—, and —C(R$^{L1}$)₂—N(R$^{L1}$)—N(R$^{L1}$)—;

wherein the bond on the left side of L¹, as drawn, is bound to the 8-membered ring of the compound of formula (II) or the compound of formula (III) and the bond on the right side of the L¹, as drawn, is bound to X¹;

Y¹ is a bond, —NH—, —O—, —S—, —NH(Y$^{1a}$)—, —O(Y$^{1a}$)—, or —S(Y$^{1a}$)—;

Y² is a bond, —C(=O)—, —S(=O)₂—, —C(=O)Y$^{2a}$—, —S(=O)₂Y$^{2a}$;

Y$^{1a}$ and Y$^{2a}$ are each independently Y³ or Y³NH—

Y³ is substituted or unsubstituted C$_{1-10}$alkyl or —(CH₂CH₂O)$_{1-10}$—; and n is an integer from 1 to 30;

k is 1, 2, or 3;

each R$^{L1}$ is independently hydrogen or substituted or unsubstituted alkyl; and R⁴, R⁵, R⁶, and R⁷ are each independently hydrogen, halo, or substituted or unsubstituted alkyl; wherein the conjugate has a molecular weight of at least 1.3 times greater than the conjugate molecular weight when LDAO is not used.

The details of the disclosure are set forth in the accompanying description below. Although methods and materials similar or equivalent to those described herein can be used in the practice or testing of the present disclosure, illustrative methods and materials are now described. Other features, objects, and advantages of the disclosure will be apparent from the description and from the claims. In the specification and the appended claims, the singular forms also include the plural unless the context clearly dictates otherwise. Unless defined otherwise, all technical and scientific terms used herein have the same meaning as commonly understood by one of ordinary skill in the art to which this disclosure belongs. All patents and publications cited in this specification are incorporated herein by reference in their entireties.

Each embodiment described herein may be taken alone or in combination with any one or more other embodiments. Additional embodiments, features, and advantages of the invention will be apparent from the following detailed description and through practice of the invention.

BACKGROUND

The Huisgen cycloaddition is a 1,3-dipolar cycloaddition between an azide and an alkyne that gives a 1,2,3-triazole product (1,3-*Dipolar Cycloaddition Chemistry*; Ed: Padwa, A.; Wiley: New York, 1984; Vol. I, pp. 1-176).

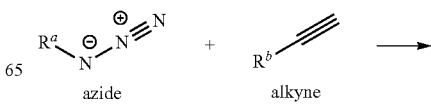

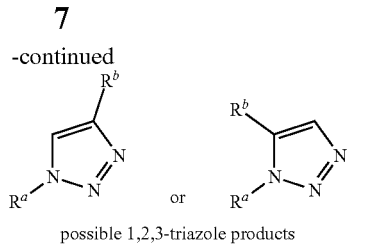

possible 1,2,3-triazole products

The 1,3-dipolar cycloaddition reaction (one type of "click" chemistry) can proceed thermally, or can be catalyzed by a metal such as copper (U.S. Pat. No. 7,375,234), resulting in both increased rate of reaction and increased selectivity for one regioisomer of the triazole product. The 1,3-dipolar cycloaddition of azides and alkynes, along with other click reactions, has found use in the synthesis of small-molecule pharmaceuticals, polymers, and conjugates (including bioconjugates).

Bioconjugation, the chemical modification or linking of one or more biomolecule (such as DNA, RNA, proteins, or carbohydrates) to a substrate (e.g., a drug) or probe (e.g., a dye or fluorophore), is used widely in biomedical research. Such bioconjugates are produced for use in both basic research and in the development of therapeutics.

The 1,3-dipolar azide-alkyne cycloaddition fits these criteria for bioconjugation, however, as mentioned previously, copper catalysts must often be employed in order to increase the rate of reaction. Copper catalysis is not ideal for use in biological systems, or for producing molecules (e.g., drugs) that will be used in biological systems, due to the toxicity of the metal. An alternative to metal-catalyzed click reactions is to use strained cyclic alkynes, which react more readily with azides than with acyclic terminal alkynes. Metal-free click reactions are particularly well-suited to bioconjugation because, ideally, neither the reactants nor products are toxic, they can be conducted in aqueous solutions (e.g., in cells or in live organisms), and they can be used to specifically label one component while leaving others untouched. General examples of metal-free click reactions used in biomedical applications can be found, for instance, in Kim, et al., *Chemical Science*, 2019, 10, 7835-7851.

Click reaction between azides and cyclic alkynes are still far slower than their metal-catalyzed counterparts, sometimes taking days for modest conversion of starting materials. There is still a need, therefore, for metal-free techniques that allow for rapid, highly selective, and high-yielding synthesis of bioconjugates. Described herein is a method for preparing heteroaryl-containing compounds using an accelerated click reaction.

BRIEF DESCRIPTION OF THE DRAWINGS

FIG. 1A shows the kinetics of a reaction between azidocoumarin and a DBCO linker under various reaction conditions.

FIG. 2A shows the antibody titers amongst all groups upon completion of treatment with conjugates made with and without LDAO. FIGS. 2B, 2C, and 2D show the antibody titers within each group post-dose 1, post-dose 2, and post-dose 3, respectively.

FIGS. 4A-4D show the saccharide monomer molecular structure and plots of conjugate molecular weight over the course of conjugation reactions for polysaccharides 3, 5, 18C, and 19A.

DETAILED DESCRIPTION

Figure 1C:
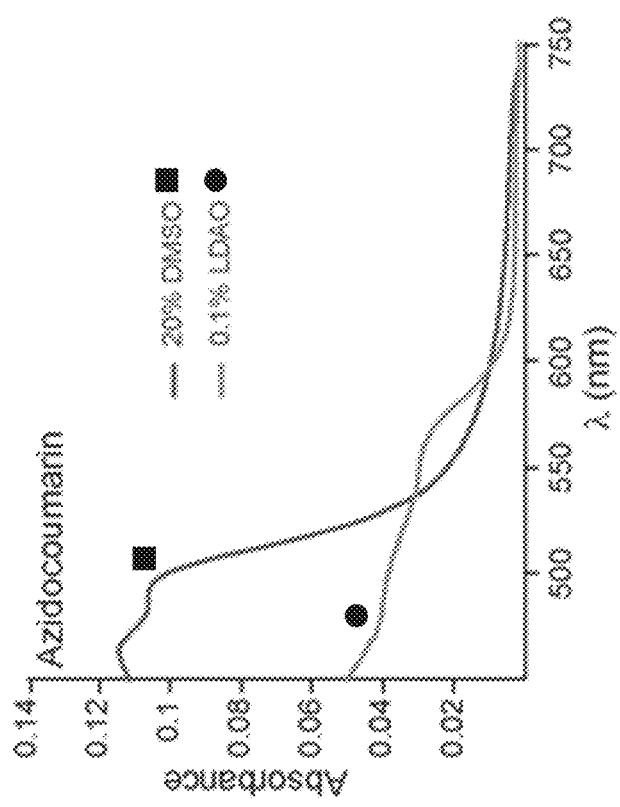
FIG. 1C shows the absorbance of azidocoumarin in both 20% DMSO and 0.1% LDAO.

As discussed herein, the present disclosure provides methods of preparing heteroaryl-containing compounds by reacting azide compounds of Formula (I) with an alkyne compound of Formula (II) or (III) in the presence of lauryldimethylamine oxide (LDAO). The presence of LDAO modifies the reaction kinetics, such that the reaction is accelerated. For some heteroaryl-containing compounds formed by the reaction between an azide compound of Formula (I) and an alkyne compound of Formula (II) or (III), the reaction may take days to run to completion. For some heteroaryl-containing compounds, when prepared by the methods of the present disclosure, the reaction time is reduced to from days to hours.

The methods of the present disclosure are scaleable and produce heteroaryl-containing compounds at good yields. The methods are suitable for both small-molecule reactants and larger molecules (e.g., biomolecules).

The articles "a" and "an" as used in this disclosure may refer to one or more than one (i.e., to at least one) of the grammatical object of the article. By way of example, "an element" means one element or more than one element.

As used in this disclosure, "and/or" may mean either "and" or "or" unless indicated otherwise.

Method of Preparing a Heteroaryl-Containing Compound

The present disclosure provides a method of preparing a heteroaryl-containing compound, the method comprising contacting an azide compound with an alkyne compound in the presence of lauryldimethylamine oxide (LDAO), water, and DMSO to form the heteroaryl-containing compound,
  wherein the LDAO is at a concentration of up to 2% v/v;
  wherein the azide compound is a compound of formula (I)

(I)

wherein the alkyne compound is a compound of formula (II) or (III)

(II)

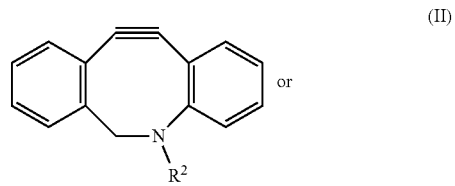

or

-continued

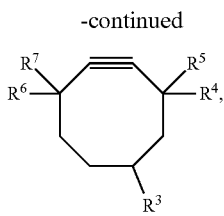

(III)

wherein

R¹, R², and R³ are independently selected from the group consisting of substituted or unsubstituted alkyl, substituted or unsubstituted alkenyl, substituted or unsubstituted alkynyl, substituted or unsubstituted alkoxy, substituted or unsubstituted cycloalkyl, substituted or unsubstituted aryl, substituted or unsubstituted heteroaryl, substituted or unsubstituted heterocyclyl, —(CH$_2$)$_a$—C(O)R$^{1a}$, —(CH$_2$)$_a$—C(O)OR$^{1a}$, —(CH$_2$)$_a$—C(O)N(R$^{1a}$)$_2$, —(CH$_2$)$_a$—C(O)NHCH(R$^{1a}$)$_2$, —(CH$_2$)$_a$—N(R$^{1a}$)$_2$; wherein a is integer from zero to 10; wherein each R$^{1a}$ is independently hydrogen, substituted or unsubstituted alkyl, substituted or unsubstituted alkenyl, substituted or unsubstituted alkoxy, substituted or unsubstituted cycloalkyl, substituted or unsubstituted aryl, substituted or unsubstituted heteroaryl, and substituted or unsubstituted heterocyclyl; or R¹ is a first polypeptide comprising at least one nnAAr of formula (IV)

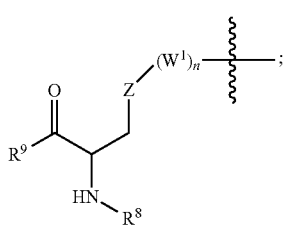

(IV)

wherein Z is absent or a 5-membered or 6-membered aryl or heteroaryl ring; W¹ is selected from the group consisting of C$_1$-C$_{10}$ alkylene, —NH—, —O— and —S—; n is zero or 1; R⁸ is H or an amino acid residue of the first polypeptide, and R⁹ is OH or an amino acid residue of the first polypeptide; and R² and R³ are independently -L¹-X¹;

wherein

X¹ is a polysaccharide or a second polypeptide;

L¹ is optional, and when present is a linker selected from the group consisting of substituted or unsubstituted alkylene, substituted or unsubstituted alkenylene, —O—, —O-(substituted or unsubstituted alkylene)-, -(substituted or unsubstituted alkylene)-O—, —O-(substituted or unsubstituted alkylene)-C(O)—Y¹—, —C(O)-(substituted or unsubstituted alkylene)-NH—Y²—, —C(O)-(substituted or unsubstituted alkylene)-C(O)—, —C(O)-(substituted or unsubstituted alkylene)-NH—C(O)—(CH$_2$—CH$_2$—O)$_n$-(substituted or unsubstituted alkylene)-NH—, —C(O)-(substituted or unsubstituted alkylene)-NH—, —C(O)-(substituted or unsubstituted alkylene)-NH—C(O)—(CH$_2$—CH$_2$—O)$_n$-(substituted or unsubstituted alkylene)-C(O)—, —C(O)-(substituted or unsubstituted alkylene)-C(O)—NH-(substituted or unsubstituted alkylene)-, —C(O)—, —C(O)-(substituted or unsubstituted alkylene)-, -(substituted or unsubstituted alkylene)-C(O)—, —C(O)N(R$^{L1}$)—, —C(O)N(R$^{L1}$)-(substituted or unsubstituted alkylene)-, -(substituted or unsubstituted alkylene)-C(O)N(R$^{L1}$), -(substituted or unsubstituted alkylene)-C(O)NR$^{L1}$-(substituted or unsubstituted alkylene)-, —OC(O)N(R$^{L1}$)—, —OC(O)N(R$^{L1}$)-(substituted or unsubstituted alkylene)-, -(substituted or unsubstituted alkylene)-OC(O)N(R$^{L1}$)—, —N(R$^{L1}$)C(O)—, —NR$^{L1}$C(O)-(substituted or unsubstituted alkylene)-, -(substituted or unsubstituted alkylene)-NR$^{L1}$C(O)—, —S—, —S-(substituted or unsubstituted alkylene)-, —S(O)$_k$—, —S(O)$_k$(alkylene or substituted alkylene)-, —C(S)—, —C(S)-(substituted or unsubstituted alkylene)-, —CSN(R$^{L1}$)—, —CSN(R$^{L1}$)-(substituted or unsubstituted alkylene)-, —N(R$^{L1}$)C(O)O—, -(substituted or unsubstituted alkylene)-O—N═CR$^{L1}$—, -(substituted or unsubstituted alkylene)-S(O)$_k$-(substituted or unsubstituted alkylene)-S—, -(substituted or unsubstituted alkylene)-S—S—, —S(O)$_k$N(R$^{L1}$)—, —N(R$^{L1}$)C(O)N(R$^{L1}$)—, —N(R$^{L1}$)C(S)N(R$^{L1}$)—, —N(R$^{L1}$)S(O)$_k$N(R$^{L1}$)—, —N(R$^{L1}$)—N═, —C(R$^{L1}$)═N—, —C(R$^{L1}$)═N—N(R$^{L1}$)—, —C(R$^{L1}$)═N—N═, —C(R$^{L1}$)$_2$—N═N—, and —C(R$^{L1}$)$_2$—N(R$^{L1}$)—N(R$^{L1}$)—; wherein the bond on the left side of L¹, as drawn, is bound to the 8-membered ring of the compound of formula (II) or the compound of formula (III) and the bond on the right side of the L¹, as drawn, is bound to X¹;

Y¹ is a bond, —NH—, —O—, —S—, —NH(Y$^{1a}$)—, —O(Y$^{1a}$)— or —S(Y$^{1a}$)—;

Y² is a bond, —C(═O)—, —S(═O)$_2$—, —C(═O)Y$^{2a}$—, or —S(═O)$_2$Y$^{2a}$;

Y$^{1a}$ and Y$^{2a}$ are each independently Y³ or Y³NH—

Y³ is substituted or unsubstituted C$_{1-10}$alkyl or —(CH$_2$CH$_2$O)$_{1-10}$—; and n is an integer from 1 to 30;

k is 1, 2, or 3;

each R$^{L1}$ is independently hydrogen or substituted or unsubstituted alkyl; and R⁴, R⁵, R⁶, and R⁷ are each independently hydrogen, halo, or substituted or unsubstituted alkyl.

"Alkyl", as used herein, refers to an unbranched or branched non-cyclic carbon chain (or carbon), which may be fully saturated, mono- or polyunsaturated and can include di- and multivalent radicals. The number of carbon atoms can be undesignated or designated (i.e., C$_1$-C$_6$ means one to six carbons). Examples of alkyl radicals include methyl, ethyl, propyl, isopropyl, n-butyl, sec-butyl, tert-butyl, pentyl, 2-pentyl, isopentyl, neopentyl, hexyl, 2-hexyl, 3-hexyl, and 3-methyl pentyl. When an alkyl residue having a specific number of carbons is named, all geometric isomers having that number of carbons may be encompassed. Thus, for example, "butyl" can include n-butyl, sec-butyl, isobutyl and t-butyl, and "propyl" can include n-propyl and isopropyl. In some embodiments, alkyl as used herein has 1 to 50 carbon atoms ((C$_1$-C$_{50}$)alkyl), 1 to 20 carbon atoms ((C$_1$-C$_{20}$)alkyl), 1 to 12 carbon atoms ((C$_1$-C$_{12}$)alkyl), 1 to 10 carbon atoms ((C$_1$-C$_{10}$)alkyl), 1 to 8 carbon atoms ((C$_1$-C$_8$)alkyl), 1 to 6 carbon atoms ((C$_1$-C$_6$)alkyl), or 1 to 4 carbon atoms ((C$_1$-C$_4$)alkyl). In other embodiments, alkyl as used herein has 2 to 6 carbon atoms ((C$_2$-C$_6$)alkyl). An alkyl group can be unsubstituted or substituted.

"Alkenyl," as used herein, includes an unbranched or branched hydrocarbon chain containing carbon atoms. The "alkenyl" group contains at least one double bond. The double bond of an alkenyl group can be unconjugated or conjugated to another unsaturated group. Examples of alkenyl groups include, but are not limited to, ethylenyl, vinyl, allyl, butenyl, pentenyl, hexenyl, butadienyl, pentadienyl, hexadienyl, 2-ethylhexenyl, 2-propyl-2-butenyl, 4-(2-methyl-3-butene)-pentenyl and the like. An alkenyl group can be unsubstituted or substituted. Alkenyl, as defined herein, may also be branched or straight. In some embodiments, alkenyl as used herein has 2 to 50 carbon atoms (($C_2$-$C_{50}$)alkenyl), 2 to 20 carbon atoms (($C_2$-$C_{20}$)alkenyl), 2 to 12 carbon atoms (($C_2$-$C_{12}$)alkenyl), 2 to 10 carbon atoms (($C_2$-$C_{10}$)alkenyl), 2 to 8 carbon atoms (($C_2$-$C_8$)alkenyl), 2 to 6 carbon atoms (($C_2$-$C_6$)alkenyl), or 2 to 4 carbon atoms (($C_2$-$C_4$)alkenyl). In other embodiments, alkenyl as used herein has 2 to 6 carbon atoms (($C_2$-$C_6$)alkenyl). An alkenyl group can be unsubstituted or substituted.

"Alkylene," as used herein, refers to a divalent radical derived from a branched or unbranched alkyl, as exemplified, but not limited, by —$CH_2CH_2CH_2CH_2$—. In some embodiments, alkylene as used herein has 1 to 50 carbon atoms (($C_1$-$C_{50}$)alkylene), 1 to 20 carbon atoms (($C_1$-$C_{20}$)alkylene), 1 to 12 carbon atoms (($C_1$-$C_{12}$)alkylene), 1 to 10 carbon atoms (($C_1$-$C_{10}$)alkylene), 1 to 8 carbon atoms (($C_1$-$C_8$)alkylene), 1 to 6 carbon atoms (($C_1$-$C_6$)alkylene), or 1 to 4 carbon atoms (($C_1$-$C_4$)alkylene). In other embodiments, alkylene as used herein has 2 to 6 carbon atoms (($C_2$-$C_6$)alkylene).

"Alkynyl," as used herein, refers to an unbranched or branched unsaturated hydrocarbon chain containing at least one triple bond. The triple bond of an alkynyl group can be unconjugated or conjugated to another unsaturated group. Examples of alkynyl groups include, but are not limited to, ethynyl, propynyl, butynyl, pentynyl, hexynyl, methylpropynyl, 4-methyl-1-butynyl, 4-propyl-2-pentynyl, 4-butyl-2-hexynyl and the like. Alkynyl, as defined herein, may also be branched or straight. In some embodiments, alkynyl as used herein has 2 to 50 carbon atoms (($C_2$-$C_{50}$)alkynyl), 2 to 20 carbon atoms (($C_2$-$C_{20}$)alkynyl), 2 to 12 carbon atoms (($C_2$-$C_{12}$)alkynyl), 2 to 10 carbon atoms (($C_2$-$C_{10}$)alkynyl), 2 to 8 carbon atoms (($C_2$-$C_8$)alkynyl), 2 to 6 carbon atoms (($C_2$-$C_6$)alkynyl), or 2 to 4 carbon atoms (($C_2$-$C_4$)alkynyl). In other embodiments, alkynyl as used herein has 2 to 6 carbon atoms (($C_2$-$C_6$)alkynyl). An alkynyl group can be unsubstituted or substituted.

"Alkoxy," as used herein, refers to a straight or branched saturated hydrocarbon containing a terminal "O" in the chain, i.e., —O(alkyl). Examples of alkoxy groups include, without limitation, methoxy, ethoxy, propoxy, butoxy, t-butoxy, or pentoxy groups. In some embodiments, alkoxy as used herein has 1 to 50 carbon atoms (—O(($C_1$-$C_{50}$)alkyl)), 1 to 20 carbon atoms (—O(($C_1$-$C_{20}$)alkyl)), 1 to 12 carbon atoms (—O(($C_1$-$C_{12}$)alkyl)), 1 to 10 carbon atoms (—O(($C_1$-$C_{10}$)alkyl)), 1 to 8 carbon atoms (—O(($C_1$-$C_8$)alkyl)), 1 to 6 carbon atoms (—O(($C_1$-$C_6$)alkyl)), or 1 to 4 carbon atoms (—O(($C_1$-$C_4$)alkyl)). In other embodiments, alkoxy as used herein has 2 to 6 carbon atoms (—O(($C_2$-$C_6$)alkyl)).

"Cycloalkyl," as used herein, refers to a monocyclic or polycyclic saturated hydrocarbon. In some embodiments, cycloalkyl has 3 to 50 carbon atoms (($C_3$-$C_{50}$)cycloalkyl), 3 to 20 carbon atoms (($C_3$-$C_{20}$)cycloalkyl), 3 to 12 carbon atoms (($C_3$-$C_{12}$)cycloalkyl), 3 to 10 carbon atoms (($C_3$-$C_{10}$)cycloalkyl), 3 to 8 carbon atoms (($C_3$-$C_8$)cycloalkyl), 3 to 6 carbon atoms (($C_3$-$C_6$)cycloalkyl), or 3 to 5 carbon atoms (($C_3$-$C_4$)cycloalkyl). Cycloalkyl includes monocyclic and polycyclic groups, such as fused bicycles, bridged rings, and spirocycles. Examples of cycloalkyl groups include cyclopropyl, cyclobutyl, cyclopentyl, cyclohexyl, octahydropentalenyl, octahydro-1H-indene, decahydronaphthalene, cubane, bicyclo[3.1.0]hexane, and bicyclo[1.1.1]pentane. A cycloalkyl group can be unsubstituted or substituted.

"Aryl," as used herein, refers to cyclic, aromatic hydrocarbon groups that have 1 to 3 aromatic rings, including monocyclic or bicyclic groups such as phenyl, biphenyl or naphthyl. In some embodiments, aryl groups have 5 to 20 ring atoms. Where containing two aromatic rings (bicyclic, etc.), the aromatic rings of the aryl group may be joined at a single point (e.g., biphenyl), or fused (e.g., naphthyl). The aryl group may be optionally substituted by one or more substituents, e.g., 1 to 5 substituents, at any point of attachment. The substituents can themselves be optionally substituted. Furthermore when containing two fused rings the aryl groups herein defined may have an unsaturated or partially saturated ring fused with a fully saturated ring. Exemplar ring systems of these aryl groups include, but are not limited to, phenyl, biphenyl, naphthyl, anthracenyl, phenalenyl, phenanthrenyl, indanyl, indenyl, tetrahydronaphthalenyl, tetrahydrobenzoannulenyl, and the like.

"Heteroaryl," as used herein, refers to a monovalent monocyclic or polycyclic aromatic radical of 5 to 18 ring atoms or a polycyclic aromatic radical, containing one or more ring heteroatoms selected from N, O, or S, the remaining ring atoms being C. Heteroaryl as herein defined also means a bicyclic heteroaromatic group wherein the heteroatom is selected from N, O, or S. The aromatic radical is optionally substituted independently with one or more substituents described herein. The substituents can themselves be optionally substituted. Examples include, but are not limited to, benzothiophene, furyl, thienyl, pyrrolyl, pyridyl, pyrazinyl, pyrazolyl, pyridazinyl, pyrimidinyl, imidazolyl, isoxazolyl, oxazolyl, oxadiazolyl, pyrazinyl, indolyl, thiophen-2-yl, quinolyl, benzopyranyl, isothiazolyl, thiazolyl, imidazolyl, triazolyl, triazinyl, indazolyl, pyrrolo[2,3-c] pyridinyl, benzoimidazolyl, benzothiazolyl, indolyl, indolinyl, indolinonyl, dihydrobenzothiophenvl, dihydrobenzofuranyl, benzofuran, chromanyl, thiochromanyl, tetrahydroquinolinyl, dihydrobenzothiazinyl, dihydrobenzoxanyl, quinolinyl, isoquinolinyl, 1,6-naphthyridinyl, and derivatives thereof. Furthermore, when containing two fused rings the heteroaryl groups herein defined may have an unsaturated or partially saturated ring fused with a fully saturated ring.

"Heterocyclyl," as used herein, refers to a saturated or partially unsaturated monocyclic or polycyclic ring containing carbon and at least one heteroatom selected from the group consisting of O, N, and S. Each ring S atom, where present, may independently be a sulfur oxide, such as —S(O)—, or —S(O)$_2$—. Heterocyclyl includes heterocycloalkyl, heteroaryl, and non-aromatic unsaturated heterocyclic groups such as heterocycloalkenyl. The heterocyclyl group may comprise 3, 4, 5, 6, 7, 8, 9, 10, 11, 12, or more ring atoms (e.g., be a 3-membered, 4-membered, 5-membered, 6-membered, 7-membered, 8-membered, 9-membered, 10-membered, 11-membered, or 12-membered heterocyclyl), and may include groups comprising 1 to 5 ring heteroatoms, 1 to 4 heteroatoms, 1 to 3 ring heteroatoms, 1 or 2 ring heteroatoms, or 1 ring heteroatom, wherein each heteroatom is independently selected from the group consisting of N, O, and S. In some embodiments, heterocyclyl is connected through an annular carbon atom, wherein the point of attachment of the heterocyclyl to another group is a ring carbon atom of the heterocyclyl.

It should also be noted that any carbon as well as heteroatom with unsatisfied valences in the text, schemes, examples and Tables herein is assumed to have the sufficient number of hydrogen atom(s) to satisfy the valences.

As used herein, references to hydrogen may also refer to a deuterium substitution if desired. The term "deuterium" as used herein means a stable isotope of hydrogen having odd numbers of protons and neutrons.

The term "halo" or "halogen" refers to fluorine, chlorine, bromine, or iodine.

In some embodiments, the present disclosure provides a method of preparing a heteroaryl-containing compound, the method comprising contacting an azide compound with an alkyne compound in the presence of lauryldimethylamine oxide (LDAO), water, and DMSO to form the heteroaryl-containing compound, wherein the LDAO is at a concentration of up to 2% v/v;

wherein the azide compound is a compound of formula (I)

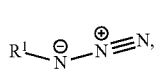
(I)

wherein the alkyne compound is a compound of formula (II)

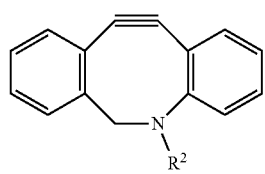
(II)

wherein $R^1$, $R^2$, and $R^3$ are independently selected from the group consisting of substituted or unsubstituted alkyl, substituted or unsubstituted alkenyl, substituted or unsubstituted alkynyl, substituted or unsubstituted alkoxy, substituted or unsubstituted cycloalkyl, substituted or unsubstituted aryl, substituted or unsubstituted heteroaryl, substituted or unsubstituted heterocyclyl, —$(CH_2)_a$—$C(O)R^{1a}$, —$(CH_2)_a$—$C(O)OR^{1a}$, —$(CH_2)_a$—$C(O)N(R^{1a})_2$, —$(CH_2)_a$—$C(O)NHCH(R^{1a})_2$, —$(CH_2)_a$—$N(R^{1a})_2$; wherein a is integer from zero to 10; wherein each $R^{1a}$ is independently hydrogen, substituted or unsubstituted alkyl, substituted or unsubstituted alkenyl, substituted or unsubstituted alkoxy, substituted or unsubstituted cycloalkyl, substituted or unsubstituted aryl, substituted or unsubstituted heteroaryl, and substituted or unsubstituted heterocyclyl.

In some embodiments, the present disclosure provides a method of preparing a heteroaryl-containing compound, the method comprising contacting an azide compound with an alkyne compound in the presence of lauryldimethylamine oxide (LDAO), water, and DMSO to form the heteroaryl-containing compound, wherein the LDAO is at a concentration of up to 2% v/v;

wherein the azide compound is a compound of formula (I)

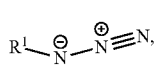
(I)

wherein the alkyne compound is a compound of formula (III)

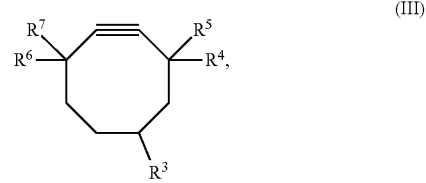
(III)

wherein $R^1$, $R^2$, and $R^3$ are independently selected from the group consisting of substituted or unsubstituted alkyl, substituted or unsubstituted alkenyl, substituted or unsubstituted alkynyl, substituted or unsubstituted alkoxy, substituted or unsubstituted cycloalkyl, substituted or unsubstituted aryl, substituted or unsubstituted heteroaryl, substituted or unsubstituted heterocyclyl, —$(CH_2)_a$—$C(O)R^{1a}$, —$(CH_2)_a$—$C(O)OR^{1a}$, —$(CH_2)_a$—$C(O)N(R^{1a})_2$, —$(CH_2)_a$—$C(O)NHCH(R^{1a})_2$, —$(CH_2)_a$—$N(R^{1a})_2$; wherein a is integer from zero to 10; wherein each $R^{1a}$ is independently hydrogen, substituted or unsubstituted alkyl, substituted or unsubstituted alkenyl, substituted or unsubstituted alkoxy, substituted or unsubstituted cycloalkyl, substituted or unsubstituted aryl, substituted or unsubstituted heteroaryl, and substituted or unsubstituted heterocyclyl.

In some embodiments, the present disclosure provides a method of preparing a heteroaryl-containing compound, the method comprising contacting an azide compound with an alkyne compound in the presence of lauryldimethylamine oxide (LDAO), water, and DMSO to form the heteroaryl-containing compound, wherein the LDAO is at a concentration of up to 2% v/v;

wherein the azide compound is a compound of formula (I)

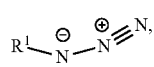
(I)

wherein the alkyne compound is a compound of formula (II)

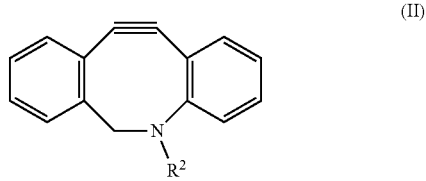
(II)

wherein

R¹ is a first polypeptide comprising at least one nnAAr of formula (IV)

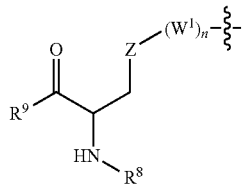

(IV)

wherein Z is absent or a 5-membered or 6-membered aryl or heteroaryl ring; W¹ is selected from the group consisting of $C_1$-$C_{10}$ alkylene, —NH—, —O— and —S—; n is zero or 1; R⁸ is H or an amino acid residue of the first polypeptide, and R⁹ is OH or an amino acid residue of the first polypeptide; and R² and R³ are independently -L¹-X¹;

wherein

X¹ is a polysaccharide or a second polypeptide;

L¹ is optional, and when present is a linker selected from the group consisting of substituted or unsubstituted alkylene, substituted or unsubstituted alkenylene, —O—, —O-(substituted or unsubstituted alkylene)-, -(substituted or unsubstituted alkylene)-O—, —O-(substituted or unsubstituted alkylene)-C(O)—Y¹—, —C(O)-(substituted or unsubstituted alkylene)-NH—Y²—, —C(O)-(substituted or unsubstituted alkylene)-C(O)—, —C(O)-(substituted or unsubstituted alkylene)-NH—C(O)—(CH₂—CH₂—O)$_n$-(substituted or unsubstituted alkylene)-NH—, —C(O)-(substituted or unsubstituted alkylene)-NH—, —C(O)-(substituted or unsubstituted alkylene)-NH—C(O)—(CH₂—CH₂—O)$_n$-(substituted or unsubstituted alkylene)-C(O)—, —C(O)-(substituted or unsubstituted alkylene)-C(O)—NH-(substituted or unsubstituted alkylene)-, —C(O)—, —C(O)-(substituted or unsubstituted alkylene)-, -(substituted or unsubstituted alkylene)-C(O)—, —C(O)N($R^{L1}$)—, —C(O)N($R^{L1}$)-(substituted or unsubstituted alkylene)-, -(substituted or unsubstituted alkylene)-C(O)N($R^{L1}$), -(substituted or unsubstituted alkylene)-C(O)N$R^{L1}$-(substituted or unsubstituted alkylene)-, —OC(O)N($R^{L1}$)—, —OC(O)N($R^{L1}$)-(substituted or unsubstituted alkylene)-, -(substituted or unsubstituted alkylene)-OC(O)N($R^{L1}$)—, —N($R^{L1}$)C(O)—, —N$R^{L1}$C(O)-(substituted or unsubstituted alkylene)-, -(substituted or unsubstituted alkylene)-N$R^{L1}$C(O)—, —S—, —S-(substituted or unsubstituted alkylene)-, —S(O)$_k$—, —S(O)$_k$(alkylene or substituted alkylene)-, —C(S)—, —C(S)-(substituted or unsubstituted alkylene)-, —CSN($R^{L1}$)—, —CSN($R^{L1}$)-(substituted or unsubstituted alkylene)-, —N($R^{L1}$)C(O)O—, -(substituted or unsubstituted alkylene)-O—N═C$R^{L1}$—, -(substituted or unsubstituted alkylene)-S(O)$_k$-(substituted or unsubstituted alkylene)-S—, -(substituted or unsubstituted alkylene)-S—S—, —S(O)$_k$N($R^{L1}$)—, —N($R^{L1}$)C(O)N($R^{L1}$)—, —N($R^{L1}$)C(S)N($R^{L1}$)—, —N($R^{L1}$)S(O)$_k$N($R^{L1}$)—, —N($R^{L1}$)—N═, —C($R^{L1}$)═N—, —C($R^{L1}$)═N—N($R^{L1}$)—, —C($R^{L1}$)═N—N═, —C($R^{L1}$)₂—N═N—, and —C($R^{L1}$)₂—N($R^{L1}$)—N($R^{L1}$)—; wherein the bond on the left side of L¹, as drawn, is bound to the 8-membered ring of the compound of formula (II) or the compound of formula (III) and the bond on the right side of the L¹, as drawn, is bound to X¹;

Y¹ is a bond, —NH—, —O—, —S—, —NH($Y^{1a}$)—, —O($Y^{1a}$)—, or —S($Y^{1a}$)—;

Y² is a bond, —C(═O)—, —S(═O)₂—, —C(═O)$Y^{2a}$—, or —S(═O)₂$Y^{2a}$;

$Y^{1a}$ and $Y^{2a}$ are each independently Y³ or Y³NH—

Y³ is substituted or unsubstituted $C_{1-10}$alkyl or —(CH₂CH₂O)$_{1-10}$—; and n is an integer from 1 to 30;

k is 1, 2, or 3;

each $R^{L1}$ is independently hydrogen or substituted or unsubstituted alkyl; and R⁴, R⁵, R⁶, and R⁷ are each independently hydrogen, halo, or substituted or unsubstituted alkyl.

A "non-natural amino acid" (nnAA) refers to an amino acid that is not one of the 20 common amino acids or pyrolysine or selenocysteine; other terms that are used synonymously with the term "non-natural amino acid" are "non-naturally encoded amino acid," "unnatural amino acid," "non-naturally occurring amino acid," and variously hyphenated and non-hyphenated versions thereof. Non-natural amino acids with bio-orthogonal reactive chemical side chains are able to be used as a chemical "handle" to conjugate various payloads to discrete sites in a protein. A "non-natural amino acid residue" (nnAAr) refers to an nnAA incorporated in a peptide. For example, an nnAAr of formula (IV) described herein. In some embodiments, the one or more nnAA comprise a click chemistry reactive group. Herein, a "click chemistry reactive group" refers to a moiety, such as an azide or an alkyne, capable of undergoing a click chemistry reaction with a second click chemistry reactive group. In some embodiments, one click chemistry reactive group reacts with a second click chemistry reactive group to form a substituted triazole. Examples of this type of click reaction can be found, for instance, in International PCT Publication No. WO 2018/126229. General examples of metal-free click reactions used in biomedical applications can be found, for instance, in Kim, et al., *Chemical Science*, 2019, 10, 7835-7851. Examples of nnAAs comprising click chemistry reactive groups include (4-azidophenyl)propanoic acid (pAF), 2-amino-4-azidobutanoic acid, 2-azido-3-phenylpropionic acid, 2-amino-3-azidopropanoic acid, 2-amino-3-(4-(azidomethyl)phenyl)propanoic acid (pAMF), 2-amino-3-(5-(azidomethyl)pyridin-2-yl)propanoic acid, 2-amino-3-(4-(azidomethyl)pyridin-2-yl)propanoic acid, 2-amino-3-(6-(azidomethyl)pyridin-3-yl)propanoic acid, and 2-amino-S-azidopentanoic acid.

In some embodiments, a polypeptide is a carrier protein. As used herein, "carrier protein" refers to a non-toxic or detoxified polypeptide containing a T-cell activating epitope which is able to be attached to an antigen (e.g., a polysaccharide) to enhance the humoral response to the conjugated antigen in a subject. The term includes any of the bacterial proteins used as epitope carriers in FDA-approved vaccines. In some embodiments, the carrier protein is *Corynebacterium diphtheriae* toxin, *Clostridium tetani* tetanospasmin, *Haemophilus influenzae* protein D (PD, HiD), outer membrane protein complex of serogroup B meningococcus (OMPC), CRM197, CRM-pAMF6 mutant, *Streptococcus pyogenes* Adhesion and Division (SpyAD) polypeptide, arginine deiminase (ADI), Protein D. or malaria ookinete specific surface protein Pfs25. In certain embodiments, the carrier protein is BB, derived from the G protein of *Streptococcus* strain G148. In some embodiments, the carrier protein is ferritin. A "native carrier protein" has only naturally occurring amino acids. An "enhanced carrier protein" has at least one non-natural amino acid replacing a naturally occurring amino acid in the carrier protein. The terms "carrier protein" and "carrier polypeptide" are used interchangeably herein.

In some embodiments, the polypeptide is CRM197 (SEQ ID NO:1). In certain embodiments, the polypeptide is CRM-pAMF6 mutant (SEQ ID NO:2). In certain embodiments, the polypeptide is SpyAD (SEQ ID NO: 10). In certain embodiments, the polypeptide is Protein D (SEQ ID NO:11).

The term "antigen" refers to any molecule or a linear molecular fragment that is able to be recognized by the highly variable antigen receptors (B-cell receptors, T-cell receptors, or both) of the adaptive immune system. Non-limiting examples of antigens include polysaccharides or glycans (e.g., bacterial capsular polysaccharides), polynucleotides, polyamino acids, lipids, and small molecules (e.g., haptens, drugs of abuse)

In some embodiments, a polypeptide is a polypeptide antigen.

In some embodiments, the polypeptide antigen is an Invasion Plasmid Antigen B (IpaB) polypeptide antigen. In some embodiments, the IpaB polypeptide antigen comprises an amino sequence substantially homologous to a wild type IpaB antigen sequence from a *Shigella* bacterium, such as *S. dysenteriae* (UniProt ID: Q03945), *S. flexneri* (UniProt ID: P18011), *S. boydii* (UniProt ID: Q8KXT4), or *S. sonnei* (UniProt ID: Q3YTQ2). In some embodiments, the IpaB polypeptide antigen comprises an amino acid sequence that is at least 75%, at least 80%, at least 90%, at least 95%, at least 96%, at least 97%, at least 99%, or 100% identical to the wild type IpaB polypeptide antigen sequence from a *Shigella* bacterium. Examples of suitable polypeptide antigens from a *Shigella* bacterium may be found in International Publication No. WO 2020/205584, the contents of which are incorporated herein in their entirety.

The full sequence of the wild type IpaB polypeptide antigen from *S. flexneri*, a 62,160 Da protein containing 580 amino acid residues, is provided in SEQ ID NO:3. Accordingly, in some embodiments, the IpaB polypeptide antigen is at least 75%, at least 80%, at least 90%, at least 95%, at least 96%, at least 97%, at least 99%, or 100% identical to SEQ ID NO:3.

In some embodiments, one or more nnAAs are incorporated into the IpaB polypeptide antigen sequence. In some embodiments, between 2 and 10 nnAAs are incorporated into the IpaB polypeptide antigen sequence. In some embodiments, at least 2, at least 3, at least 4, at least 5, at least 6, at least 7, at least, 8, at least 9, or at least 10 nnAAs are incorporated into the IpaB polypeptide antigen sequence. In some embodiments, the sites at which the nnAA is incorporated are selected from K241, K262, K269, K283, K289, K299, C309, K312, S329, S333, D347, E360, K368, E372, K376, D380, K384, E387, D392, K394, K395, K397, K424, K429, K436, K440, K448, K451, K470, and K482 of SEQ ID NO: 1. In some embodiments, the sites at which the nnAA is incorporated are selected from K289, K299, K368, K395, K436, and K470. Specification of an nnAA incorporated at a particular site refers to the replacement of the indicated amino acid at the indicated position of an nnAA. For example, incorporation of an nnAA at position K289 means that the lysine residue present at position 289 is replaced by a nnAA.

In some embodiments, the IpaB polypeptide antigen comprises an nnAA incorporated each of positions K289, K368, and K395 of SEQ ID NO: 3. For example, in some embodiments, the IpaB polypeptide antigen comprises the amino acid sequence of SEQ ID NO: 4. In some embodiments, the IpaB polypeptide antigen comprises an nnAA incorporated each of positions K299, K395, and K436 of SEQ ID NO: 3. For example, in some embodiments, the IpaB polypeptide antigen comprises the amino acid sequence of SEQ ID NO: 5.

In some embodiments, the IpaB polypeptide antigen comprises an nnAA incorporated each of positions K299, K368, and K395 of SEQ ID NO: 3. For example, in some embodiments, the IpaB polypeptide antigen comprises the amino acid sequence of SEQ ID NO: 6. In some embodiments, the IpaB polypeptide antigen comprises an nnAA incorporated each of positions K289, K368, K395, and K436 of SEQ ID NO: 3. For example, in some embodiments, the IpaB polypeptide antigen comprises the amino acid sequence of SEQ ID NO: 7.

In some embodiments, the IpaB polypeptide antigen comprises an nnAA incorporated each of positions K299, K395, K436, and K470 of SEQ ID NO: 3. For example, in some embodiments, the IpaB polypeptide antigen comprises the amino acid sequence of SEQ ID NO: 8. In some embodiments, the IpaB polypeptide antigen comprises an nnAA incorporated each of positions K299, K368, K395, and K436 of SEQ ID NO: 3. For example, in some embodiments, the IpaB polypeptide antigen comprises the amino acid sequence of SEQ ID NO: 9.

In some embodiments, the polypeptide antigen is a Group A *Streptococcus* (GAS) antigen. In some embodiments, a GAS polypeptide antigen is a full-length GAS antigen. In some embodiments, a GAS polypeptide antigen is a peptide fragment of a full-length GAS antigen. In some embodiments, a GAS polypeptide antigen is C5a peptidase, streptolysin O (SLO), Sib35, or Sfb1. Examples of suitable GAS antigens may be found in International Application No. PCT/US2021/018402, the contents of which are incorporated herein in their entirety.

In some embodiments, the polypeptide antigen is a SpyAD polypeptide. In some embodiments, a SpyAD polypeptide is a full-length SpyAD antigen. In some embodiments, a SpyAD polypeptide is a peptide fragment of a full-length SpyAD antigen. In some embodiments, the SpyAD polypeptide is at least 75%, at least 80%, at least 90%, at least 95%, at least 96%, at least 97%, at least 99%, or 100% identical to SEQ ID NO:12.

In some embodiments, one or more nnAAs are incorporated into the SpyAD sequence. In some embodiments, between 2 and 10 nnAAs are incorporated into the SpyAD sequence. In some embodiments, at least 2, at least 3, or at least 4 nnAAs are incorporated into the SpyAD sequence. In some embodiments, the sites at which the nnAA is incorporated are selected from K64, K287, K386, and K657. In some embodiments, the sites at which the nnAA is incorporated are K64, K287, K386, and K657. In some embodiments, the SpyAD sequence is at least 75%, at least 80%, at least 90%, at least 95%, at least 96%, at least 97%, at least 99%, or 100% identical to SEQ ID NO:13.

The term "T-cell activating epitope" refers to a structural unit of molecular structure which is capable of inducing T-cell immunity.

The term "polysaccharide" as used herein, is used in its ordinary sense, including, without limitation, saccharides comprising a plurality of repeating units, including, but not limited to polysaccharides having 50 or more repeat units, and oligosaccharides having 50 or less repeating units. Typically, polysaccharides have from about 50, 55, 60, 65, 70, 75, 80, 85, 90, or 95 repeating units to about 2,000 or more repeating units, and optionally from about 100, 150, 200, 250, 300, 350, 400, 500, 600, 700, 800, 900 or 1000 repeating units to about, 1100, 1200, 1300, 1400, 1500, 1600, 1700, 1800, or 1900 repeating units. Oligosaccharides typically have from about 6, 7, 8, 9, or 10 repeating units to about 15, 20, 25, 30, or 35 to about 40 or 45 repeating units.

The term "polypeptide" is intended to include any structure comprised of one or more amino acids, and thus includes dipeptides, oligopeptides, polypeptides, polypeptide fragments, antibodies, and proteins. The amino acids forming all or a part of a polypeptide may be any of the twenty conventional, naturally occurring amino acids, i.e., alanine (A), cysteine (C), aspartic acid (D), glutamic acid (E), phenylalanine (F), glycine (G), histidine (H), isoleucine (I), lysine (K), leucine (L), methionine (M), asparagine (N), proline (P), glutamine (Q), arginine (R), serine (S), threonine (T), valine (V), tryptophan (W), and tyrosine (Y), as well as non-conventional amino acids such as isomers and modifications of the conventional amino acids, e.g., D-amino acids, non-protein amino acids, post-translationally modified amino acids, enzymatically modified amino acids, β-amino acids, constructs or structures designed to mimic amino acids (e.g., α,α-disubstituted amino acids, N-alkyl amino acids, lactic acid, β-alanine, naphthylalanine, 3-pyridylalanine, 4-hydroxyproline, O-phosphoserine, N-acetylserine, N-formylmethionine, 3-methylhistidine, 5-hydroxylysine, and nor-leucine), and other non-conventional amino acids, as described, for example, in U.S. Pat. No. 5,679,782 to Rosenberg et al. The polypeptides described herein may include one or more nnAAs bearing a functional group that enables conjugation to a secondary antigen, e.g., a polysaccharide. Polypeptides can be (a) naturally occurring, (b) produced by chemical synthesis, (c) produced by recombinant DNA technology, (d) produced by biochemical or enzymatic fragmentation of larger molecules, (e) produced by methods resulting from a combination of methods (a) through (d) listed above, or (f) produced by any other means for producing peptides, such as cell-free protein synthesis, described infra.

In some embodiments, the present disclosure provides a method of preparing a heteroaryl-containing compound, the method comprising contacting an azide compound with an alkyne compound in the presence of lauryldimethylamine oxide (LDAO), water, and DMSO to form the heteroaryl-containing compound, wherein the LDAO is at a concentration of up to 2% v/v;
wherein the azide compound is a compound of formula (I)

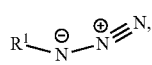

(I)

wherein the alkyne compound is a compound of formula (III)

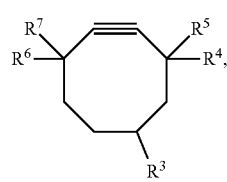

(III)

wherein
$R^1$ is a first polypeptide comprising at least one nnAAr of formula (IV)

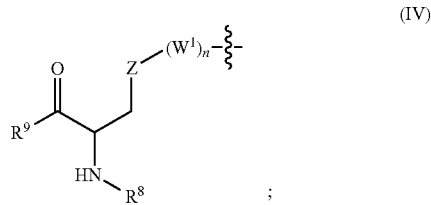

(IV)

wherein Z is absent or a 5-membered or 6-membered aryl or heteroaryl ring; $W^1$ is selected from the group consisting of $C_1$-$C_{10}$ alkylene, —NH—, —O— and —S—; n is zero or 1; $R^8$ is H or an amino acid residue of the first polypeptide, and $R^9$ is OH or an amino acid residue of the first polypeptide; and
$R^2$ and $R^3$ are independently -$L^1$-$X^1$;
wherein
$X^1$ is a polysaccharide or a second polypeptide;
$L^1$ is optional, and when present is a linker selected from the group consisting of substituted or unsubstituted alkylene, substituted or unsubstituted alkenylene, —O—, —O-(substituted or unsubstituted alkylene)-, -(substituted or unsubstituted alkylene)-O—, —O-(substituted or unsubstituted alkylene)-C(O)—$Y^1$—, —C(O)-(substituted or unsubstituted alkylene)-NH—$Y^2$—, —C(O)-(substituted or unsubstituted alkylene)-C(O)—, —C(O)-(substituted or unsubstituted alkylene)-NH—C(O)—$(CH_2$—$CH_2$—O$)_n$-(substituted or unsubstituted alkylene)-NH—, —C(O)-(substituted or unsubstituted alkylene)-NH—, —C(O)-(substituted or unsubstituted alkylene)-NH—C(O)—$(CH_2$—$CH_2$—O$)_n$-(substituted or unsubstituted alkylene)-C(O)—, —C(O)-(substituted or unsubstituted alkylene)-C(O)—NH-(substituted or unsubstituted alkylene)-, —C(O)—, —C(O)-(substituted or unsubstituted alkylene)-, -(substituted or unsubstituted alkylene)-C(O)—, —C(O)N($R^{L1}$)—, —C(O)N($R^{L1}$)-(substituted or unsubstituted alkylene)-, -(substituted or unsubstituted alkylene)-C(O)N($R^{L1}$), -(substituted or unsubstituted alkylene)-C(O)N$R^{L1}$-(substituted or unsubstituted alkylene)-, —OC(O)N($R^{L1}$)—, —OC(O)N($R^{L1}$)-(substituted or unsubstituted alkylene)-, -(substituted or unsubstituted alkylene)-OC(O)N($R^{L1}$)—, —N($R^H$)C(O)—, —N$R^{L1}$C(O)-(substituted or unsubstituted alkylene)-, -(substituted or unsubstituted alkylene)-N$R^{L1}$C(O)—, —S—, —S-(substituted or unsubstituted alkylene)-, —S(O)$_k$—, —S(O)$_k$(alkylene or substituted alkylene)-, —C(S)—, —C(S)-(substituted or unsubstituted alkylene)-, —CSN($R^{L1}$)—, —CSN($R^{L1}$)-(substituted or unsubstituted alkylene)-, —N($R^{L1}$)C(O)O—, -(substituted or unsubstituted alkylene)-O—N=C$R^{L1}$—, -(substituted or unsubstituted alkylene)-S(O)$_k$-(substituted or unsubstituted alkylene)-S—, -(substituted or unsubstituted alkylene)-S—S—, —S(O)$_k$N($R^{L1}$)—, —N($R^{L1}$)C(O)N($R^{L1}$)—, —N($R^{L1}$)C(S)N($R^{L1}$)—, —N($R^{L1}$)S(O)$_k$N($R^{L1}$)—, —N($R^{L1}$)—N=, —C($R^{L1}$)=N—, —C($R^{L1}$)=N—N($R^{L1}$)—, —C($R^{L1}$)=N—N=, —C($R^{L1}$)$_2$—N=N—, and —C($R^{L1}$)$_2$—N($R^{L1}$)—N($R^{L1}$)—; wherein the bond on the left side of $L^1$, as drawn, is bound to the 8-membered ring of the compound of formula (II) or the compound of formula (III) and the bond on the right side of the $L^1$, as drawn, is bound to $X^1$;

$Y^1$ is a bond, —NH—, —O—, —S—, —NH($Y^{1a}$)—, —O($Y^{1a}$)— or —S($Y^{1a}$)—;

$Y^2$ is a bond, —C(=O)—, —S(=O)$_2$—, —C(=O)$Y^{2a}$—, or —S(=O)$_2Y^{2a}$;

$Y^{1a}$ and $Y^{2a}$ are each independently $Y^3$ or $Y^3$NH—

$Y^3$ is substituted or unsubstituted $C_{1-10}$alkyl or —(CH$_2$CH$_2$O)$_{1-10}$—; and n is an integer from 1 to 30;

k is 1, 2, or 3;

each $R^{L1}$ is independently hydrogen or substituted or unsubstituted alkyl; and $R^4$, $R^5$, $R^6$, and $R^7$ are each independently hydrogen, halo, or substituted or unsubstituted alkyl.

Azide Reactant

In some embodiments is an azide compound of Formula (I):

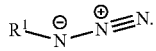

In some embodiments, $R^1$ is selected from the group consisting of substituted or unsubstituted alkyl, substituted or unsubstituted alkenyl, substituted or unsubstituted alkynyl, substituted or unsubstituted alkoxy, substituted or unsubstituted cycloalkyl, substituted or unsubstituted aryl, substituted or unsubstituted heteroaryl, substituted or unsubstituted heterocyclyl, —(CH$_2$)$_a$—C(O)R$^{1a}$, —(CH$_2$)$_a$—C(O)OR$^{1a}$, —(CH$_2$)$_a$—C(O)N(R$^{1a}$)$_2$, —(CH$_2$)$_a$—C(O)NHCH(R$^{1a}$)$_2$, —(CH$_2$)$_a$—N(R$^{1a}$)$_2$.

In some embodiments, a is integer from zero to 10. In some embodiments, a is 0. In some embodiments, a is 1. In some embodiments, a is 2. In some embodiments, a is 3. In some embodiments, a is 4. In some embodiments, a is 5. In some embodiments, a is 6. In some embodiments, a is 7. In some embodiments, a is 8. In some embodiments, a is 9. In some embodiments, a is 10. In some embodiments, each $R^{1a}$ is independently hydrogen, substituted or unsubstituted alkyl, substituted or unsubstituted alkenyl, substituted or unsubstituted alkoxy, substituted or unsubstituted cycloalkyl, substituted or unsubstituted aryl, substituted or unsubstituted heteroaryl, and substituted or unsubstituted heterocyclyl.

In some embodiments, $R^1$ is heterocyclyl. In certain embodiments, $R^1$ is coumarinyl. In certain embodiments, the azide compound is

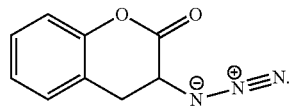

In some embodiments, the azide compound is a compound of Formula (I):

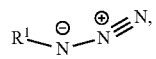

and $R^1$ is a first polypeptide comprising at least one nnAAr of Formula (IV):

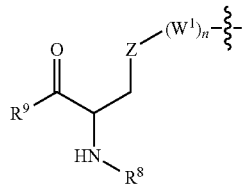

In some embodiments, Z is absent or a 5-membered or 6-membered aryl or heteroaryl ring. In certain embodiments, Z is a 5-membered aryl or heteroaryl ring. In certain embodiments, Z is a 5-membered aryl ring. In certain embodiments, Z is a 5-membered heteroaryl ring. In some embodiments, Z is a 6-membered aryl ring. In certain embodiments, Z is a 6-membered heteroaryl ring.

In some embodiments, $W^1$ is selected from the group consisting of $C_1$-$C_{10}$ alkylene, —NH—, —O— and —S—. In some embodiments, $W^1$ is —CH$_2$—.

In some embodiments n is zero or 1. In certain embodiments n is 0. In certain embodiments, n is 1.

In some embodiments, $R^8$ is H or an amino acid residue of the first polypeptide, and $R^9$ is OH or an amino acid residue of the first polypeptide. In certain embodiments, $R^8$ is H and $R^9$ is OH. In some embodiments, $R^8$ is H and $R^9$ is an amino acid residue of the first polypeptide. In certain embodiments, $R^8$ an amino acid residue of the first polypeptide and $R^9$ is OH. In certain embodiments, $R^8$ is H or an amino acid residue of the first polypeptide and $R^9$ is OH or an amino acid residue of the first polypeptide.

In some embodiments of the azide compound of Formula (I), $R^1$ is a first polypeptide comprising at least one non-natural amino acid residue of Formula (IV), wherein Z is phenyl, and n is zero. In certain embodiments of the azide compound of Formula (I), $R^1$ is a first polypeptide comprising at least one non-natural amino acid residue of Formula (IV), wherein Z is phenyl, and n is 1. In certain embodiments of the azide compound of Formula (I), $R^1$ is a first polypeptide comprising at least one non-natural amino acid residue of Formula (IV), wherein Z is phenyl, n is 1, and W is $C_1$-$C_{10}$ alkylene. In certain embodiments of the azide compound of Formula (I), $R^1$ is a first polypeptide comprising at least one non-natural amino acid residue of Formula (IV), wherein Z is pyridinyl, and n is 1. In certain embodiments of the azide compound of Formula (I), $R^1$ is a first polypeptide comprising at least one non-natural amino acid residue of Formula (IV), wherein Z is pyridinyl, n is 1, and W is $C_1$-$C_{10}$ alkylene. In certain embodiments of the azide compound of Formula (I), $R^1$ is a first polypeptide comprising at least one non-natural amino acid residue of Formula (IV), wherein Z is phenyl, and n is 1. In some embodiments of the azide compound of Formula (I), $R^1$ is a first polypeptide comprising at least one non-natural amino acid residue of Formula (IV), wherein Z is absent, n is 1, and W is $C_1$-$C_{10}$ alkylene. In some embodiments of the azide compound of Formula (I), $R^1$ is a first polypeptide comprising at least one nnAAr of Formula (IV), wherein Z is absent, n is 1, and W is $C_2$ alkylene.

In certain embodiments, a polypeptide comprises at least 1 nnAA residue. In another embodiment, the at least 1 non-natural amino acids is selected from the group consisting of 2-amino-3-(4-azidophenyl)propanoic acid (pAF), 2-amino-3-(4-(azidomethyl)phenyl)propanoic acid (pAMF), 2-amino-3-(5-(azidomethyl)pyridin-2-yl)propanoic acid, 2-amino-3-(4-(azidomethyl)pyridin-2-yl)propanoic acid, 2-amino-3-(6-(azidomethyl)pyridin-3-yl)propanoic acid, 2-amino-S-azidopentanoic acid, or 2-amino-3-(4-(azidomethyl)phenyl)propanoic acid, and any combination thereof.

In some embodiments, the nnAAr of Formula (IV) is:

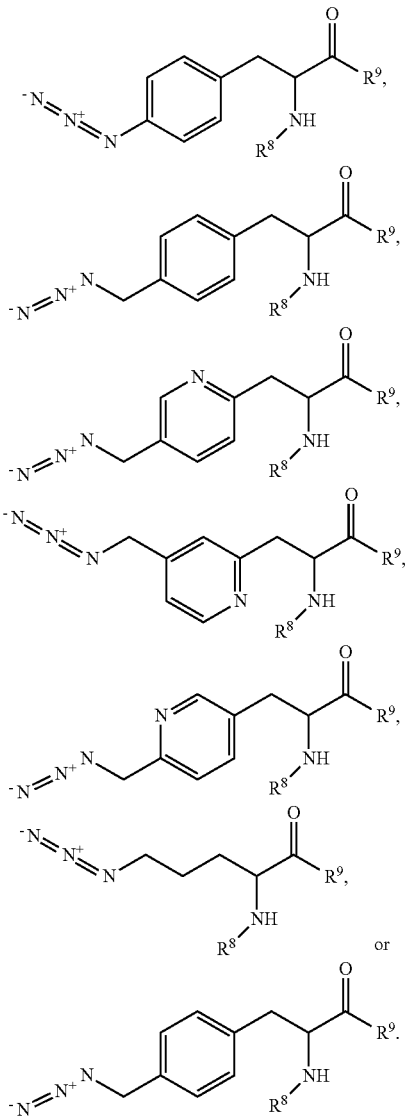

In some embodiments, $R^1$ is a polypeptide comprising at least one nnAArs of Formula (IV). In some embodiments, $R^1$ is a polypeptide comprising at least 2 nnAArs of Formula (IV). In some embodiments, $R^1$ is a polypeptide comprising at least 3 nnAArs of Formula (IV). In some embodiments, $R^1$ is a polypeptide comprising at least 4 nnAArs of Formula (IV). In some embodiments, $R^1$ is a polypeptide comprising at least 5 nnAArs of Formula (IV). In some embodiments, $R^1$ is a polypeptide comprising at least 6 nnAArs of Formula (IV). In certain embodiments, $R^1$ is a polypeptide comprising one nnAArs of Formula (IV). In some embodiments, $R^1$ is a polypeptide comprising at least 7 nnAArs of Formula (IV). In some embodiments, $R^1$ is a polypeptide comprising at least 8 nnAArs of Formula (IV). In some embodiments, $R^1$ is a polypeptide comprising at least 9 nnAArs of Formula (IV). In some embodiments, $R^1$ is a polypeptide comprising at least 10 nnAArs of Formula (IV). In some embodiments, $R^1$ is a polypeptide comprising at least 11 nnAArs of Formula (IV). In some embodiments, $R^1$ is a polypeptide comprising at least 12 nnAArs of Formula (IV).

In certain embodiments, $R^1$ is a polypeptide comprising 1-2 nnAArs of Formula (IV). In certain embodiments, $R^1$ is a polypeptide comprising 2-4 nnAArs of Formula (IV). In certain embodiments, $R^1$ is a polypeptide comprising 4-6 nnAArs of Formula (IV). In certain embodiments, $R^1$ is a polypeptide comprising 6-8 nnAArs of Formula (IV). In certain embodiments, $R^1$ is a polypeptide comprising 6-8 nnAArs of Formula (IV). In certain embodiments, $R^1$ is a polypeptide comprising 8-10 nnAArs of Formula (IV). In certain embodiments, $R^1$ is a polypeptide comprising 10-12 nnAArs of Formula (IV). In certain embodiments, $R^1$ is a polypeptide comprising 6 nnAArs of Formula (IV). In certain embodiments, $R^1$ is a polypeptide comprising 1-6 nnAArs of Formula (IV). In certain embodiments, $R^1$ is a polypeptide comprising 2-6 nnAArs of Formula (IV). In certain embodiments, $R^1$ is a polypeptide comprising 3-6 nnAArs of Formula (IV). In certain embodiments, $R^1$ is a polypeptide comprising 4-6 nnAArs of Formula (IV). In certain embodiments, $R^1$ is a polypeptide comprising 5-6 nnAArs of Formula (IV). In certain embodiments, $R^1$ is a polypeptide comprising 6-7 nnAArs of Formula (IV). In certain embodiments, $R^1$ is a polypeptide comprising 6-8 nnAArs of Formula (IV). In certain embodiments, $R^1$ is a polypeptide comprising 6-9 nnAArs of Formula (IV). In certain embodiments, $R^1$ is a polypeptide comprising 6-10 nnAArs of Formula (IV). In certain embodiments, $R^1$ is a polypeptide comprising 6-11 nnAArs of Formula (IV). In certain embodiments, $R^1$ is a polypeptide comprising 6-12 nnAArs of Formula (IV). In certain embodiments, $R^1$ is a polypeptide comprising 6-8 nnAArs of Formula (IV). In certain embodiments, $R^1$ is a polypeptide comprising 5-7 nnAArs of Formula (IV). In certain embodiments, $R^1$ is a polypeptide comprising 1-10 nnAArs of Formula (IV). In certain embodiments, $R^1$ is a polypeptide comprising 5-10 nnAArs of Formula (IV). In certain embodiments, $R^1$ is a polypeptide comprising greater than 10 nnAArs of Formula (IV).

In some embodiments, $R^1$ is a polypeptide comprising more than one nnAAr, wherein all the incorporated nnAArs are the same nnAAr structure. In certain embodiments, $R^1$ is a polypeptide comprising more than one nnAAr, wherein more than one type of nnAAr is incorporated.

In some embodiments, the nnAAr of Formula (IV) replaces any one of the 20 naturally occurring amino acids in the polypeptide comprising at least one non-natural amino acid. In some embodiments, the nnAAR replaces a lysine residue in the polypeptide comprising at least one non-natural amino acid. In some embodiments, each of the nnAAr present in a polypeptide replaces a lysine residue of the polypeptide. In some embodiments, the nnAAr replaces a phenylalanine residue. In some embodiments, each of the nnAAr present in a polypeptide replaces a phenylalanine residue of the polypeptide.

In some embodiments, $R^1$ is a polypeptide comprising at least one non-natural amino acid residue (nnAAr) and having a molecular weight between 1 and 1000 kDa. In certain embodiments, $R^1$ is a polypeptide comprising at least one nnAAr and having a molecular weight between 1 and 500 kDa. In some embodiments, $R^1$ is a polypeptide comprising at least one nnAAr and having a molecular weight between 1 and 250 kDa. In some embodiments, $R^1$ is a polypeptide comprising at least one nnAAr and having a molecular weight between 1 and 100 kDa. In some embodiments, $R^1$ is a polypeptide comprising at least one nnAAR and having a molecular weight between 1 and 50 kDa. In some embodiments, $R^1$ is a polypeptide comprising at least one n nnAAR and having a molecular weight between 50 and 100 kDa. In some embodiments, $R^1$ is a polypeptide comprising at least one nnAAR and having a molecular weight between 50 and 60 kDa. In some embodiments, $R^1$ is a polypeptide comprising at least one nnAAR and having a molecular weight of at least 500 kDa.

In certain embodiments, $R^1$ is a polypeptide with at least 80% sequence identity to SEQ ID NO:1. In certain embodiments, $R^1$ is a polypeptide with at least 85% sequence identity to SEQ ID NO:1. In certain embodiments, $R^1$ is a polypeptide with at least 90% sequence identity to SEQ ID NO:1. In certain embodiments, $R^1$ is a polypeptide with at least 95% sequence identity to SEQ ID NO:1. In some embodiments, $R^1$ is a polypeptide, wherein the polypeptide is a polypeptide of SEQ ID NO:1, wherein at least one lysine residue is replaced by a nnAAr of Formula IV.

In some embodiments, $R^1$ is a polypeptide, wherein the polypeptide is a polypeptide of SEQ ID NO:2.

In some embodiments, $R^1$ is a polypeptide with at least 80% sequence identity to SEQ ID NO:3. In certain embodiments, $R^1$ is a polypeptide with at least 85% sequence identity to SEQ ID NO:3. In certain embodiments, $R^1$ is a polypeptide with at least 90% sequence identity to SEQ ID NO:3. In certain embodiments, $R^1$ is a polypeptide with at least 95% sequence identity to SEQ ID NO:3. In some embodiments, $R^1$ is a polypeptide, wherein the polypeptide is a polypeptide of SEQ ID NO:3, wherein at least one lysine residue is replaced by a nnAAr of Formula IV.

In some embodiments, $R^1$ is a polypeptide, wherein the polypeptide is a polypeptide of SEQ ID NO:4. In some embodiments, $R^1$ is a polypeptide, wherein the polypeptide is a polypeptide of SEQ ID NO:5. In some embodiments, $R^1$ is a polypeptide, wherein the polypeptide is a polypeptide of SEQ ID NO:6. In some embodiments, $R^1$ is a polypeptide, wherein the polypeptide is a polypeptide of SEQ ID NO:7. In some embodiments, $R^1$ is a polypeptide, wherein the polypeptide is a polypeptide of SEQ ID NO:8. In some embodiments, $R^1$ is a polypeptide, wherein the polypeptide is a polypeptide of SEQ ID NO:9.

In some embodiments, $R^1$ is a polypeptide, wherein the polypeptide is a polypeptide of SEQ ID NO:12. In certain embodiments, $R^1$ is a polypeptide with at least 80% sequence identity to SEQ ID NO:12. In certain embodiments, $R^1$ is a polypeptide with at least 85% sequence identity to SEQ ID NO:12. In certain embodiments, $R^1$ is a polypeptide with at least 90% sequence identity to SEQ ID NO:12. In certain embodiments, $R^1$ is a polypeptide with at least 95% sequence identity to SEQ ID NO:12. In some embodiments, $R^1$ is a polypeptide, wherein the polypeptide is a polypeptide of SEQ ID NO:12, wherein at least one lysine residue is replaced by a nnAAr of Formula IV.

In some embodiments, $R^1$ is a polypeptide, wherein the polypeptide is a polypeptide of SEQ ID NO:13. In certain embodiments, $R^1$ is a polypeptide with at least 80% sequence identity to SEQ ID NO:13. In certain embodiments, $R^1$ is a polypeptide with at least 85% sequence identity to SEQ ID NO:13. In certain embodiments, $R^1$ is a polypeptide with at least 90% sequence identity to SEQ ID NO:13. In certain embodiments, $R^1$ is a polypeptide with at least 95% sequence identity to SEQ ID NO:13. In some embodiments, $R^1$ is a polypeptide, wherein the polypeptide is a polypeptide of SEQ ID NO:13, wherein at least one lysine residue is replaced by a nnAAr of Formula IV.

The term "sequence identity" or "percent identity" in the context of two or more nucleic acids or polypeptide sequences, refers to two or more sequences that are the same or have a specified percentage of amino acid residues or nucleotides that are the same, when compared and aligned for maximum correspondence over a comparison window, as measured using a sequence comparison algorithm (e.g., BLASTP for amino acid sequences). As used herein, the percent identity is determined over the full-length sequence, such as the reference sequence set forth in SEQ ID NO:1. The method for calculating the sequence identity as provided herein is the BLASTP program having its defaults set at a wordlength (W) of 3, an expectation (E) of 10, and the BLOSUM62 scoring matrix (see, e.g., Henikoff & Henikoff, 1989, *Proc Natl Acad Sci USA* 89:10915). See e.g., the BLAST alignment tool available on the WWW at blast.ncbi.nlm.nih.gov/Blast.cgi.

In some embodiments, $R^1$ is a polypeptide, wherein the polypeptide comprises at least one residue sequence, selected from the group consisting of residue sequences 271-290, 321-340, 331-350, 351-370, 411-430, and 431-450 of SEQ ID NO:1, that does not contain the at least 1 nnAArs.

In some embodiments, $R^1$ is a polypeptide of SEQ ID NO:1, wherein at least one nnAAr replaces an amino acid residue selected from the group consisting of K11, K25, K34, K38, K40, K83, K104, K105, K126, K158, K173, K213, K215, K217, K222, K228, K230, K237, K243, K245, K265, K300, K386, K457, K475, K499, K517, K523, K527, K535, F13, F54, F124, F128, F141, F168, F251, F390, F531, F532, D212, D296, D353, D392, D466, D468, D508, D520, N297, N360, N400, N482, N487, N503, N525, E241, E249, E250, E257, E260, E293, E363, Q253, Q288, R378, R408, R456, R461, R463, R473, R494, S199, S201, S232, S234, S240, S262, S375, S382, S398, S452, S476, S495, S496, S497, S502, S506, T254, T266, T268, T270, T294, T387, T401, T409, T470, and T518.

In some embodiments, $R^1$ is a polypeptide of SEQ ID NO:1, wherein at least one nnAAr replaces an amino acid selected from: a) a first group consisting of K25, K34, K38, K40, K213, K215, K228, K245, K265, K386, K523, and K527; b) a second group consisting of K25, K34, K38 and K40; c) a third group consisting of K213 and K215; d) a fourth group consisting of K11, K25, K34, K38, K40, K83, K104, K105, K126, K158, K173, K213, K215, K222, K228, K237, K243, K245, K265, K386, K475, K499, K523, K527, F13, F54, F124, F128, F141, F168, F251, F390, F531, and F532; and e) a fifth group consisting of K25, K215, K228, K265, K386, and K523.

In some embodiments, $R^1$ is a polypeptide of SEQ ID NO:1, wherein 2-4 nnAAr replace amino acid residues selected from the group consisting of K228, K245, K265, K386, K523, and K527.

Alkyne Reactant

In some embodiments is an alkyne compound. In certain embodiments, the alkyne compound is a compound of Formula (II):

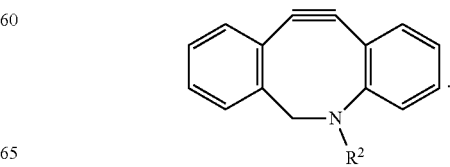

In certain embodiments, the alkyne compound is a compound of Formula (III):

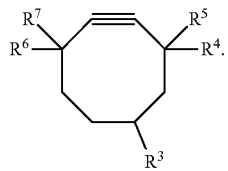

In some embodiments, $R^2$ or $R^3$ are selected from the group consisting of substituted or unsubstituted alkyl, substituted or unsubstituted alkenyl, substituted or unsubstituted alkynyl, substituted or unsubstituted alkoxy, substituted or unsubstituted cycloalkyl, substituted or unsubstituted aryl, substituted or unsubstituted heteroaryl, substituted or unsubstituted heterocyclyl, —$(CH_2)_a$—$C(O)R^{1a}$, —$(CH_2)_a$—$C(O)OR^{1a}$, —$(CH_2)_a$—$C(O)N(R^{1a})_2$, —$(CH_2)_a$—$C(O)NHCH(R^{1a})_2$, —$(CH_2)_a$—$N(R^{1a})_2$.

In some embodiments, a is integer from zero to 10. In some embodiments, a is 0. In some embodiments, a is 1. In some embodiments, a is 2. In some embodiments, a is 3. In some embodiments, a is 4. In some embodiments, a is 5. In some embodiments, a is 6. In some embodiments, a is 7. In some embodiments, a is 8. In some embodiments, a is 9. In some embodiments, a is 10. In some embodiments, each $R^{1a}$ is independently hydrogen, substituted or unsubstituted alkyl, substituted or unsubstituted alkenyl, substituted or unsubstituted alkoxy, substituted or unsubstituted cycloalkyl, substituted or unsubstituted aryl, substituted or unsubstituted heteroaryl, and substituted or unsubstituted heterocyclyl.

In some embodiments, $R^2$ is -$L^1$-$X^1$. In some embodiments, $R^3$ is -$L^1$-$X^1$. In some embodiments, $X^1$ is a polysaccharide or a second polypeptide. In some embodiments, $X^1$ is a polysaccharide. In some embodiments, $X^1$ is a polypeptide.

In some embodiments, $L^1$ is optional. In certain embodiments, $L^1$ is present. In certain embodiments, $L^1$ is not present. In certain embodiments, $L^1$ is present and is a linker selected from the group consisting of substituted or unsubstituted alkylene, substituted or unsubstituted alkenylene, —O—, —O-(substituted or unsubstituted alkylene)-, -(substituted or unsubstituted alkylene)-O—, (substituted or unsubstituted alkylene)-C(O)—$Y^1$—, —C(O)-(substituted or unsubstituted alkylene)-NH—$Y^2$—, —C(O)-(substituted or unsubstituted alkylene)-C(O)—, —C(O)-(substituted or unsubstituted alkylene)-NH—C(O)—$(CH_2$—$CH_2$—$O)_n$-(substituted or unsubstituted alkylene)-NH—, —C(O)-(substituted or unsubstituted alkylene)-NH—, —C(O)-(substituted or unsubstituted alkylene)-NH—C(O)—$(CH_2$—$CH_2$—$O)_n$-(substituted or unsubstituted alkylene)-C(O)—, —C(O)-(substituted or unsubstituted alkylene)-C(O)—NH-(substituted or unsubstituted alkylene)-, —C(O)—, —C(O)-(substituted or unsubstituted alkylene)-, -(substituted or unsubstituted alkylene)-C(O)—, —C(O)N($R^{L1}$)—, —C(O)N($R^{L1}$)-(substituted or unsubstituted alkylene)-, -(substituted or unsubstituted alkylene)-C(O)N($R^{L1}$), -(substituted or unsubstituted alkylene)-C(O)N$R^{L1}$-(substituted or unsubstituted alkylene)-, —OC(O)N($R^{L1}$)—, —OC(O)N($R^{L1}$)-(substituted or unsubstituted alkylene)-, -(substituted or unsubstituted alkylene)-OC(O)N($R^{L1}$)—, —N($R^{L1}$)C(O)—, —N$R^{L1}$C(O)-(substituted or unsubstituted alkylene)-, -(substituted or unsubstituted alkylene)-N$R^{L1}$C(O)—, —S—, —S-(substituted or unsubstituted alkylene)-, —S(O)$_k$—, —S(O)$_k$(alkylene or substituted alkylene)-, —C(S)—, —C(S)-(substituted or unsubstituted alkylene)-, —CSN($R^{L1}$)—, —CSN($R^{L1}$)-(substituted or unsubstituted alkylene)-, —N($R^{L1}$)C(O)O—, -(substituted or unsubstituted alkylene)-O—N=C$R^{L1}$—, -(substituted or unsubstituted alkylene)-S(O)$_k$-(substituted or unsubstituted alkylene)-S—, -(substituted or unsubstituted alkylene)-S—S—, —S(O)$_k$N($R^{L1}$)—, —N($R^{L1}$)C(O)N($R^{L1}$)—, —N($R^{L1}$)C(S)N($R^{L1}$)—, —N($R^{L1}$)S(O)$_k$N($R^{L1}$)—, —N($R^{L1}$)—N=, —C($R^{L1}$)=N—, —C($R^{L1}$)=N—N($R^{L1}$)—, —C($R^{L1}$)=N—N=, —C($R^{L1}$)$_2$—N=N—, and —C($R^{L1}$)$_2$—N($R^{L1}$)—N($R^{L1}$)—; wherein the bond on the left side of $L^1$, as drawn, is bound to the 8-membered ring of the compound of formula (II) or the compound of formula (III) and the bond on the right side of the $L^1$, as drawn, is bound to $X^1$.

In some embodiments, $Y^1$ is a bond, —NH—, —O—, —S—, —NH($Y^{1a}$)—, —O($Y^{1a}$)—, or —S($Y^{1a}$)—. In certain embodiments, $Y^1$ is a bond. In certain embodiments, $Y^1$ is —NH—. In certain embodiments, $Y^1$ is —O—. In certain embodiments, $Y^1$ is —S—. In certain embodiments, $Y^1$ is —NH($Y^{1a}$)—. In certain embodiments, $Y^1$ is —O($Y^{1a}$)—. In certain embodiments, $Y^1$ is —S($Y^{1a}$)—.

In some embodiments, $Y^2$ is a bond, —C(=O)—, —S(=O)$_2$—, —C(=O)$Y^{2a}$—, —S(=O)$_2Y^{2a}$. In certain embodiments, $Y^2$ is a bond. In certain embodiments, $Y^2$ is —C(=O)—. In certain embodiments, $Y^2$ is —S(=O)$_2$—. In certain embodiments, $Y^2$ is —C(=O)$Y^{2a}$—. In certain embodiments, $Y^2$ is —S(=O)$_2Y^{2a}$.

In some embodiments, $Y^{1a}$ is $Y^3$ or $Y^3$NH—. In certain embodiments, $Y^{1a}$ is $Y^{1a}$ is $Y^3$. In some embodiments, $Y^{1a}$ is $Y^3$NH—. In some embodiments, $Y^{2a}$ is $Y^3$ or $Y^3$NH—. In certain embodiments, $Y^{2a}$ is $Y^3$. In some embodiments, $Y^{2a}$ is $Y^3$NH—.

In some embodiments, $Y^3$ is substituted or unsubstituted $C_{1-10}$alkyl or —$(CH_2CH_2O)_{1-10}$—. In certain embodiments, $Y^3$ is substituted $C_{1-10}$alkyl or —$(CH_2CH_2O)_{1-10}$—. In certain embodiments, $Y^3$ is unsubstituted $C_{1-10}$alkyl or —$(CH_2CH_2O)_{1-10}$—. In certain embodiments, $Y^3$ is substituted $C_{1-10}$alkyl. In certain embodiments, $Y^3$ is substituted —$(CH_2CH_2O)_{1-10}$—. In certain embodiments, $Y^3$ is unsubstituted $C_{1-10}$alkyl. In certain embodiments, $Y^3$ is unsubstituted —$(CH_2CH_2O)_{1-10}$—.

In some embodiments, n is an integer from 1 to 30. In certain embodiments, n is an integer from 1-5. In certain embodiments, n is an integer from 1-10. In certain embodiments, n is an integer from 10-15. In certain embodiments, n is an integer from 10-20. In certain embodiments, n is an integer from 20-25. In certain embodiments, n is an integer from 25-30. In some embodiments, n is 1. In certain embodiments, n is 2. In certain embodiments, n is 3. In certain embodiments, n is 4. In certain embodiments, n is 5.

In some embodiments, k is 1, 2, or 3. In certain embodiments, k is 1. In certain embodiments, k is 2. In certain embodiments, k is 3.

In some embodiments, each $R^{L1}$ is independently hydrogen or substituted or unsubstituted alkyl. In some embodiments, $R^4$, $R^5$, $R^6$, and $R^7$ are each independently hydrogen, halo, or substituted or unsubstituted alkyl.

In some embodiments, an alkyne compound is a compound of formula (II), wherein $R^2$ is -$L^1$-$X^1$, wherein $L^1$ is —C(O)-(substituted or unsubstituted alkylene)-NH—C(O)—$(CH_2$—$CH_2$—$O)_n$-(substituted or unsubstituted alkylene)-NH—; wherein n is 1-10. In certain embodiments, an alkyne compound is a compound of formula (II), wherein $R^2$ is -$L^1$-$X^1$, wherein $L^1$ is —C(O)-(substituted or unsubstituted alkylene)-NH—C(O)—$(CH_2$—$CH_2$—$O)_n$-(substituted or unsubstituted alkylene)-NH—; wherein n is 4.

In some embodiments, an alkyne compound is a compound of formula (V), (VI), (VII), (VIII), (IX), (X), (XI), or (XII):

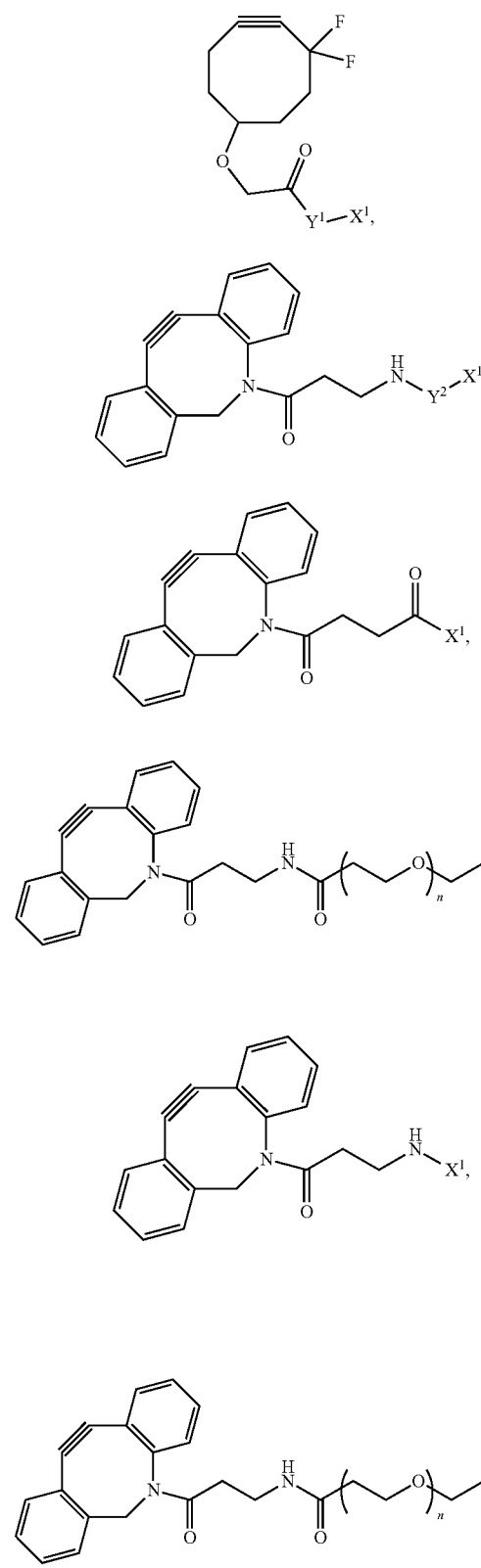

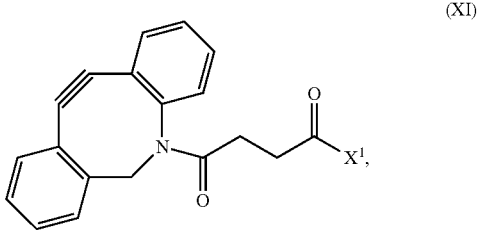

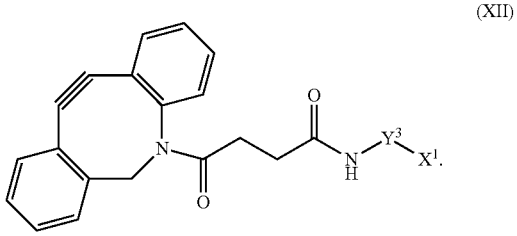

In some embodiments, $X^1$ is a polypeptide or polysaccharide. In certain embodiments, $X^1$ is a polypeptide. In certain embodiments, $X^1$ is a polysaccharide. In some embodiments, $X^1$ is a capsular polysaccharide from a bacterium selected from the group consisting of *Streptococcus pneumoniae, Neisseria meningitidis, Haemophilus influenzae, Streptococcus pyogenes, Streptococcus agalactiae,* and *Porphyromonas gingivalis*. In certain embodiments, $X^1$ is a capsular polysaccharide from a bacterium selected from the group consisting of *Streptococcus pneumoniae*.

In some embodiments, $X^1$ is a capsular polysaccharide of a *S. pneumoniae* serotype selected from the group consisting of 1, 3, 4, 5, 6A, 6B, 7F, 9V, 14, 18C, 19A, 19F and 23F, 2, 6C, 8, 9N, 10A, 12F, 15A, 15B, 15C, 16F, 17F, 20, 20A, 20B, 22F, 23A, 23B, 24F, 24B, 31, 33F, 34, 35B, 35F and 38.

In some embodiments, $X^1$ is an O-antigen *Shigella* polysaccharide. The O-antigen *Shigella* polysaccharide domain of lipopolysaccharide (LPS) is both an essential virulence factor and a protective antigen of *Shigella*. In some embodiments, the O-antigen *Shigella* polysaccharide is selected from serotypes 1a, 1b, 2a, 2b, 3b, 4a, 4b, 5a, 5b, 6, 7a, 7b, or combinations thereof. In some embodiments, an alkyne compound is a compound of Formula (VIII), wherein $X^1$ is a capsular polysaccharide from a bacterium selected from the group consisting of *Streptococcus pneumoniae, Neisseria meningitidis, Haemophilus influenzae, Streptococcus pyogenes, Streptococcus agalactiae, Porphyromonas gingivalis, Shigella flexneri, Shigella sonnei,* and *Shigella dysenteriae*. In certain embodiments, $X^1$ is a capsular polysaccharide from a bacterium selected from the group consisting of *Streptococcus pneumoniae*. In some embodiments, an alkyne compound is a compound of Formula (VIII), wherein $X^1$ is a capsular polysaccharide from a bacterium selected from the group consisting of *Shigella flexneri, Shigella dysenteriae,* and *Shigella sonnei*.

Reaction Conditions

This disclosure provides reaction conditions for any of the methods of preparing heteroaryl-containing compounds as described herein. In some embodiments is an amount of lauryldimethylamine oxide (LDAO) suitable for catalyzing the reaction producing a heteroaryl-containing compound.

In some embodiments of a method of preparing a heteroaryl-containing compound, the lauryldimethylamine oxide (LDAO) is at a concentration of up to 2% v/v. In some embodiments, the LDAO is at a concentration of less than 0.1%. In some embodiments, the LDAO is at a concentration of about 0.01% to 0.02%. In certain embodiments, the LDAO is at a concentration of about 0.01% to 0.03%. In certain embodiments, the LDAO is at a concentration of about 0.01% to 0.04%. In certain embodiments, the LDAO is at a concentration of about 0.01% to 0.05%. In certain embodiments, the LDAO is at a concentration of about 0.02% to 0.03%. In certain embodiments, the LDAO is at a concentration of about 0.03% to 0.04%. In certain embodiments, the LDAO is at a concentration of about 0.04% to 0.5%. In certain embodiments, the LDAO is at a concentration of about 0.05% to 0.06%. In certain embodiments, the LDAO is at a concentration of about 0.06% to 0.07%. In certain embodiments, the LDAO is at a concentration of about 0.07% to 0.08%. In certain embodiments, the LDAO is at a concentration of about 0.08% to 0.09%. In certain embodiments, the LDAO is at a concentration of about 0.09% to 0.1%. In certain embodiments, the LDAO is at a concentration of about 0.01% to 0.1%. In certain embodiments, the LDAO is at a concentration of about 0.1% v/v. In certain embodiments, the LDAO is at a concentration of about 0.01% to 2% v/v. In certain embodiments, the LDAO is at a concentration of between about 0.5% and 2% v/v. In certain embodiments, the LDAO is at a concentration of between about 0.1% and about 1% v/v. In certain embodiments, the LDAO is at a concentration of between about 1% and 2% v/v. In certain embodiments, the LDAO is at a concentration of between about 0.1% and about 0.2% v/v. In certain embodiments, the LDAO is at a concentration of between about 0.2% and about 0.4% v/v. In certain embodiments, the LDAO is at a concentration of between about 0.4% and about 0.6% v/v. In certain embodiments, the LDAO is at a concentration of between about 0.6% and about 0.8% v/v. In certain embodiments, the LDAO is at a concentration of between about 0.8% and about 1% v/v. In certain embodiments, the LDAO is at a concentration of between about 1% and about 1.2% v/v. In certain embodiments, the LDAO is at a concentration of between about 1.2% and about 1.4% v/v. In certain embodiments, the LDAO is at a concentration of between about 1.4% and about 1.6% v/v. In certain embodiments, the LDAO is at a concentration of between about 1.6% and about 1.8% v/v. In certain embodiments, the LDAO is at a concentration of between about 1.8% and 2% v/v. In some embodiments, the LDAO is at a concentration of 2% v/v.

In some embodiments of a method of preparing a heteroaryl-containing compound, the method is performed in 10% to 20% v/v DMSO. In certain embodiments, the method is performed in 10% to 20% v/v DMSO. In certain embodiments, the method is performed in about 10% to 12% v/v DMSO. In certain embodiments, the method is performed in about 12% to 14% v/v DMSO. In certain embodiments, the method is performed in about 14% to 16% v/v DMSO. In certain embodiments, the method is performed in about 16% to 18% v/v DMSO. In certain embodiments, the method is performed in about 18% to 20% v/v DMSO. In certain embodiments, the method is performed in about 20% to 22% v/v DMSO. In certain embodiments, the method is performed in about 22% to 24% v/v DMSO. In certain embodiments, the method is performed in about 24% to 26% v/v DMSO. In certain embodiments, the method is performed in about 26% to 28% v/v DMSO. In certain embodiments, the method is performed in about 28% to 30% v/v DMSO. In certain embodiments, the method is performed in 15% v/v DMSO.

In some embodiments of a method of preparing a heteroaryl-containing compound, the alkyne compound is at a concentration of 0.5 mg/ml to 2 mg/ml. In certain embodiments, the alkyne compound is at a concentration of 0.5 mg/ml to 1 mg/ml. In certain embodiments, the alkyne compound is at a concentration of 1 mg/ml to 2 mg/ml. In certain embodiments, the alkyne compound is at a concentration of 1 mg/ml to 1.5 mg/ml. In certain embodiments, the alkyne compound is at a concentration of 1.5 mg/ml to 2 mg/ml. In certain embodiments, the alkyne compound is at a concentration of 2 mg/ml.

In some embodiments of a method of preparing a heteroaryl-containing compound, a first polypeptide comprising at least one non-natural amino acid (nnAA) is at a concentration of 0.5 mg/ml to 2 mg/ml. In certain embodiments, the first polypeptide comprising at least one non-natural amino acid is at a concentration of 0.5 mg/ml to 1 mg/ml. In certain embodiments, the first polypeptide comprising at least one non-natural amino acid is at a concentration of 1 mg/ml to 2 mg/ml. In certain embodiments, the first polypeptide comprising at least one non-natural amino acid is at a concentration of 1 mg/ml to 1.5 mg/ml. In certain embodiments, the first polypeptide comprising at least one non-natural amino acid is at a concentration of 1.5 mg/ml to 2 mg/ml. In certain embodiments, the first polypeptide comprising at least one non-natural amino acid is at a concentration of 2 mg/ml.

In some embodiments, a method of preparing a heteroaryl-containing compound is performed at a temperature from 0° C. to 100° C. In certain embodiments, a method of preparing a heteroaryl-containing compound is performed at a temperature from 0° C. to 50° C. In some embodiments, a method of preparing a heteroaryl-containing compound is performed at a temperature from 0° C. to room temperature. In certain embodiments, a method of preparing a heteroaryl-containing compound is performed at room temperature. In some embodiments, a method of preparing a heteroaryl-containing compound is performed at a temperature from 22° C. to 25° C.

In some embodiments, a method of preparing a heteroaryl-containing compound is performed for less than one hour. In certain embodiments, a method of preparing a heteroaryl-containing compound is performed for 1 to 24 hours. In certain embodiments, a method of preparing a heteroaryl-containing compound is performed for 2-4 hours. In certain embodiments, a method of preparing a heteroaryl-containing compound is performed for 2-4 hours.

Exemplary Heteroaryl-Containing Compounds

The present disclosure provides for heteroaryl-containing compounds of formulae XVII, XVIII, XIX, or XX:

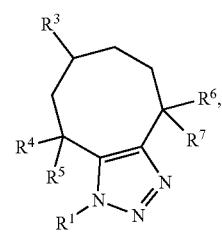

(XVII)

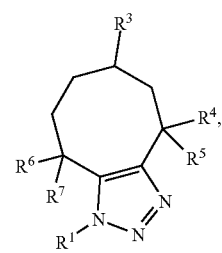

(XVIII)

(XIX)

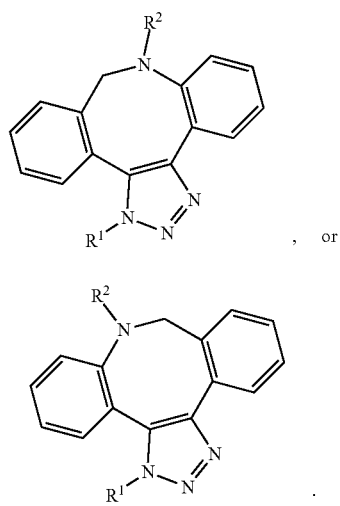

, or (XX)

In some embodiments, the heteroaryl-containing compound is a compound of formula (XXI-A), (XXI-B), (XXI-C), or (XXI-D):

(XXI-A)

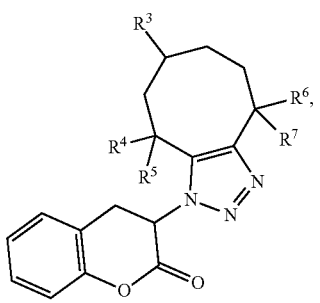

(XXI-B)

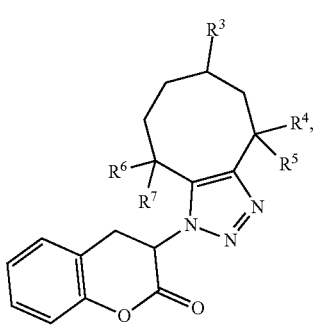

(XXI-C)

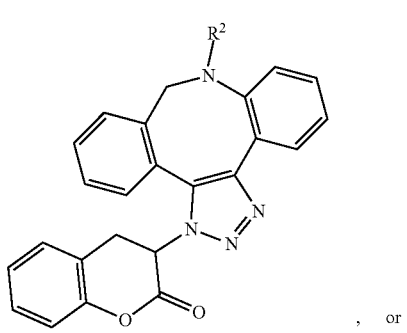

, or (XXI-D)

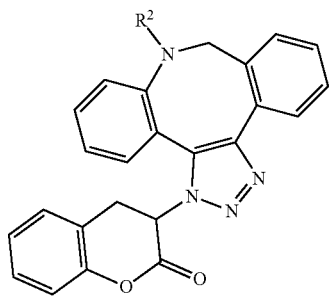

In some embodiments, the heteroaryl-containing compound is a compound of formula (XXII-A) or (XXI-B):

(XXII-A)

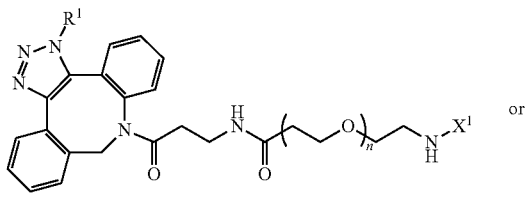

or (XXII-B)

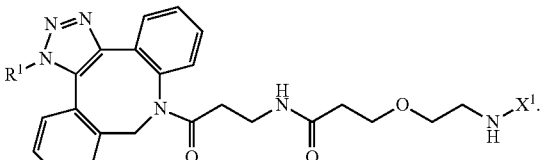

Conjugates

The present disclosure provides for heteroaryl-containing bioconjugates prepared using any of the methods disclosed herein. As used herein, a heteroaryl-containing bioconjugate refers to a heteroaryl-containing compound wherein $R^1$ is a polypeptide. Thus, in some embodiments, the present disclosure provides for a heteroaryl-containing bioconjugate, wherein $R^1$ is a first polypeptide comprising at least one nnAAr of Formula (IV). In some embodiments is a heteroaryl-containing compound comprising 1 nnAAr. In certain embodiments is a heteroaryl-containing compound comprising 2 nnAArs. In certain embodiments is a heteroaryl-containing compound comprising 3 nnAArs. In certain embodiments is a heteroaryl-containing compound comprising 4 nnAArs. In certain embodiments is a heteroaryl-containing compound comprising 5 nnAArs. In certain embodiments is a heteroaryl-containing compound comprising 6 nnAArs. In certain embodiments is a heteroaryl-containing compound comprising greater than 6 nnAArs.

In some embodiments, the present disclosure provides a heteroaryl-containing bioconjugate comprising a first polypeptide and antigen of any one of Formulae XIII, XIV, XV, or XVI:

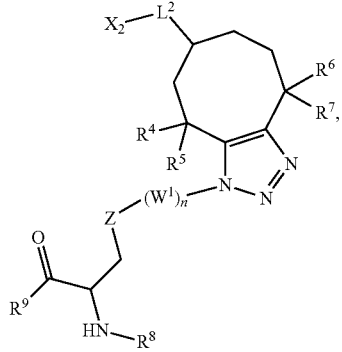

(XIII)

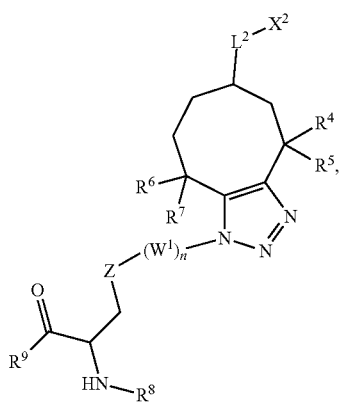

(XIV)

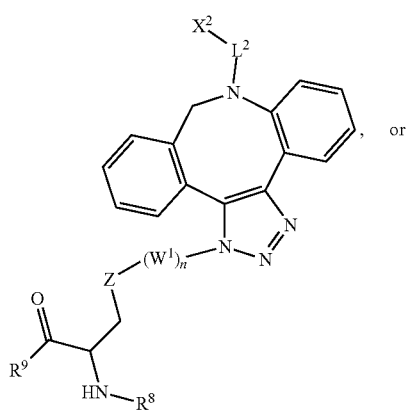

(XV), or

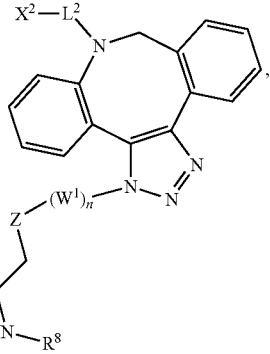

(XVI)

wherein
the first polypeptide comprises at least one nnAAr comprising an azido moiety, of Formula (I'):

(I')

wherein Z is absent or a 5-membered or 6-membered aryl or heteroaryl ring; $W^1$ is selected from the group consisting of $C_1$-$C_{10}$ alkylene, —NH—, —O— and —S—; n is zero or 1; $R^8$ is H or an amino acid residue of the first polypeptide, and $R^9$ is OH or an amino acid residue of the first polypeptide wherein at least one of $R^8$ and $R^9$ is an amino acid residue of the first polypeptide;
the azido moiety of the nnAAr is conjugated to an alkyne by contacting the nnAAr and the alkyne in the presence of LDAO,
the alkyne is formula II'-A, III'-A, or III'-B:

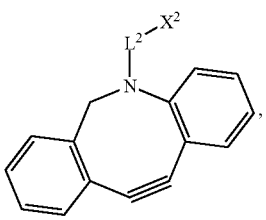

(II'-A)

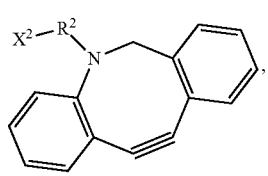

(II'-B)

-continued

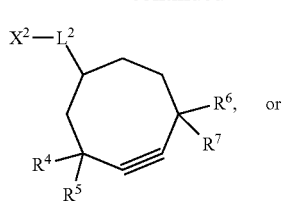
(III'-A)

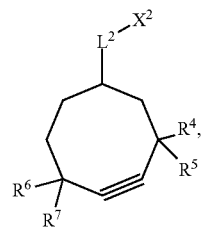
(III'-B)

wherein

X$^2$ is an antigen comprising a polysaccharide or second polypeptide,

L$^2$ is optional, and when present is a linker selected from the group consisting of substituted or unsubstituted alkylene, substituted or unsubstituted alkenylene, —O—, —O-(substituted or unsubstituted alkylene)-, -(substituted or unsubstituted alkylene)-O—, —O-(substituted or unsubstituted alkylene)-C(O)—Y$^1$—, —C(O)-(substituted or unsubstituted alkylene)-NH—Y$^2$—, —C(O)-(substituted or unsubstituted alkylene)-C(O)—, —C(O)-(substituted or unsubstituted alkylene)-NH—C(O)—(CH$_2$—CH$_2$—O)$_n$-(substituted or unsubstituted alkylene)-NH—, —C(O)-(substituted or unsubstituted alkylene)-NH—, —C(O)-(substituted or unsubstituted alkylene)-NH—C(O)—(CH$_2$—CH$_2$—O)$_n$-(substituted or unsubstituted alkylene)-C(O)—, —C(O)-(substituted or unsubstituted alkylene)-C(O)—NH-(substituted or unsubstituted alkylene)-, —C(O)—, —C(O)-(substituted or unsubstituted alkylene)-, -(substituted or unsubstituted alkylene)-C(O)—, —C(O)N(R$^{L1}$)—, —C(O)N(R$^{L1}$)-(substituted or unsubstituted alkylene)-, -(substituted or unsubstituted alkylene)-C(O)N(R$^{L1}$)-, -(substituted or unsubstituted alkylene)-C(O)NR$^{L1}$-(substituted or unsubstituted alkylene)-, —OC(O)N(R$^{L1}$)—, —OC(O)N(R$^{L1}$)-(substituted or unsubstituted alkylene)-, -(substituted or unsubstituted alkylene)-OC(O)N(R$^{L1}$)—, —N(R$^{L1}$)C(O)—, —NR$^{L1}$C(O)-(substituted or unsubstituted alkylene)-, -(substituted or unsubstituted alkylene)-NR$^{L1}$C(O)—, —S—, —S-(substituted or unsubstituted alkylene)-, —S(O)$_k$—, —S(O)$_k$(alkylene or substituted alkylene)-, —C(S)—, —C(S)-(substituted or unsubstituted alkylene)-, —CSN(R$^{L1}$)—, —CSN(R$^{L1}$)-(substituted or unsubstituted alkylene)-, —N(R$^{L1}$)C(O)O—, -(substituted or unsubstituted alkylene)-O—N=CR$^{L1}$—, -(substituted or unsubstituted alkylene)-S(O)$_k$-(substituted or unsubstituted alkylene)-S—, -(substituted or unsubstituted alkylene)-S—S—, —S(O)$_k$N(R$^{L1}$)—, —N(R$^{L1}$)C(O)N(R$^{L1}$)—, —N(R$^{L1}$)C(S)N(R$^{L1}$)—, —N(R$^{L1}$)S(O)$_k$N(R$^{L1}$)—, —N(R$^{L1}$)—N=, —C(R$^{L1}$)=N—, —C(R$^{L1}$)=N—N(R$^{L1}$)—, —C(R$^{L1}$)=N—N=, —C(R$^{L1}$)$_2$—N=N—, and —C(R$^{L1}$)$_2$—N(R$^{L1}$)—N(R$^{L1}$)—; wherein the bond on the left side of L$^1$, as drawn, is bound to the 8-membered ring of the compound of formula (II) or the compound of formula (III) and the bond on the right side of the L$^1$, as drawn, is bound to X$^1$;

Y$^1$ is a bond, —NH—, —O—, —S—, —NH(Y$^{1a}$)—, —O(Y$^{1a}$)— or —S(Y$^{1a}$)—;

Y$^2$ is a bond, —C(=O)—, —S(=O)$_2$—, —C(=O)Y$^{2a}$—, —S(=O)$_2$Y$^{2a}$;

Y$^{1a}$ and Y$^{2a}$ are each independently Y$^3$ or Y$^3$NH—

Y$^3$ is substituted or unsubstituted C$_{1-10}$alkyl or —(CH$_2$CH$_2$O)$_{1-10}$—; and n is an integer from 1 to 30;

k is 1, 2, or 3;

each R$^{L1}$ is independently hydrogen or substituted or unsubstituted alkyl; and R$^4$, R$^5$, R$^6$, and R$^7$ are each independently hydrogen, halo, or substituted or unsubstituted alkyl;

wherein the antibody titer upon challenge is greater for the conjugate compared to antibody titer upon challenge of a conjugate of the same formula where conjugation of the first polypeptide and the antigen is performed in the absence of LDAO, when tested under equivalent challenge conditions.

In some embodiments, the present disclosure provides a heteroaryl-containing bioconjugate comprising a first polypeptide and antigen of any one of Formulae XIII, XIV, XV, or XVI:

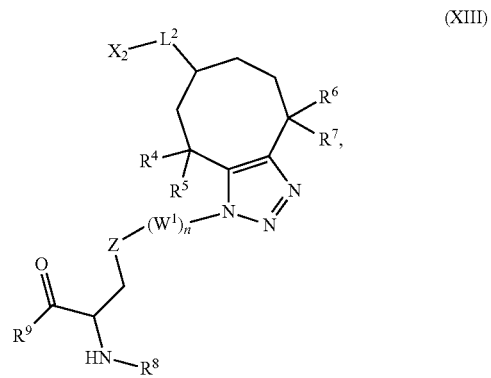
(XIII)

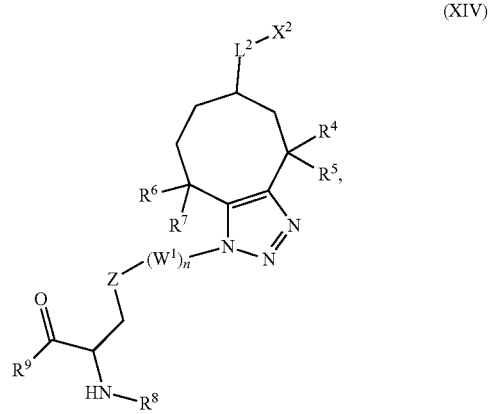
(XIV)

(XV)

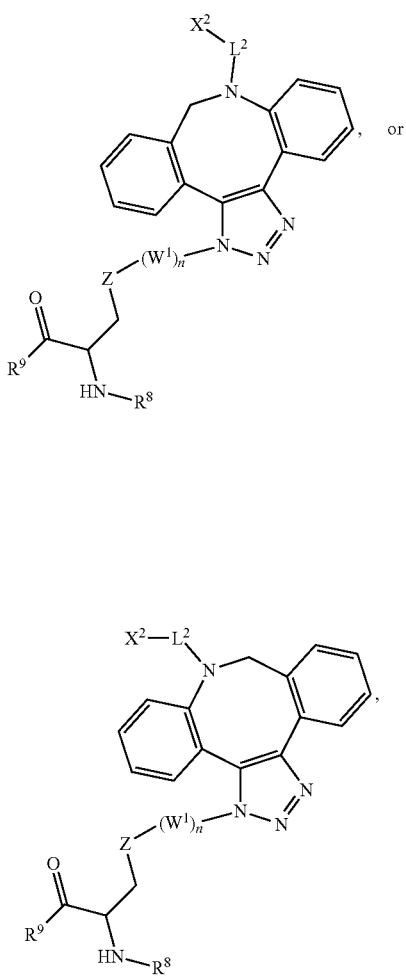

(XVI)

wherein
the first polypeptide comprises at least one nnAAr comprising an azido moiety, of Formula (I'):

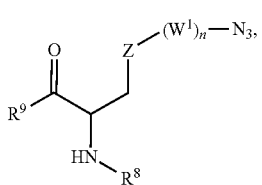

(I')

wherein Z is absent or a 5-membered or 6-membered aryl or heteroaryl ring; $W^1$ is selected from the group consisting of $C_1$-$C_{10}$ alkylene, —NH—, —O— and —S—; n is zero or 1; $R^8$ is H or an amino acid residue of the first polypeptide, and $R^9$ is OH or an amino acid residue of the first polypeptide, wherein at least one of $R^8$ and $R^9$ is an amino acid residue of the first polypeptide;

the azido moiety of the nnAAr is conjugated to an alkyne by contacting the nnAAr and the alkyne in the presence of LDAO, the alkyne is formula II'-A, III'-A, or III'-B:

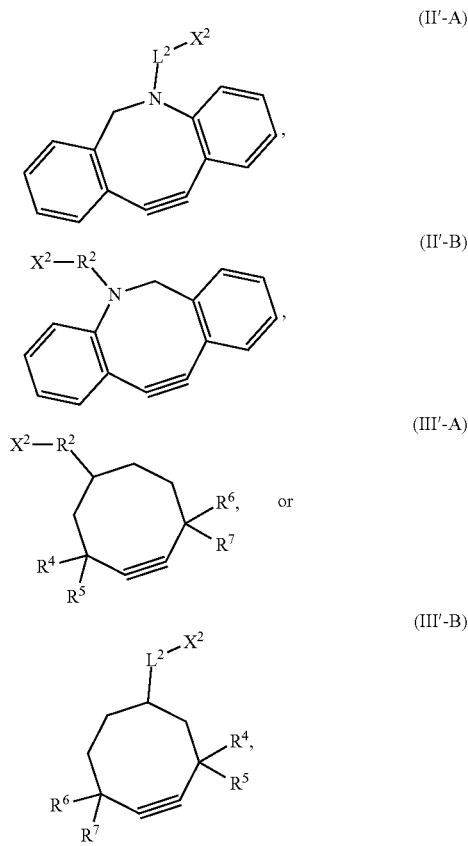

wherein
$X^2$ is an antigen comprising a polysaccharide or second polypeptide,
$L^2$ is optional, and when present is a linker selected from the group consisting of substituted or unsubstituted alkylene, substituted or unsubstituted alkenylene, —O—, —O-(substituted or unsubstituted alkylene)-, -(substituted or unsubstituted alkylene)-O—, —O-(substituted or unsubstituted alkylene)-C(O)—$Y^1$—, —C(O)-(substituted or unsubstituted alkylene)-NH—$Y^2$—, —C(O)-(substituted or unsubstituted alkylene)-C(O)—, —C(O)-(substituted or unsubstituted alkylene)-NH—C(O)—($CH_2$—$CH_2$—O)$_n$-(substituted or unsubstituted alkylene)-NH—, —C(O)-(substituted or unsubstituted alkylene)-NH—, —C(O)-(substituted or unsubstituted alkylene)-NH—C(O)—($CH_2$—$CH_2$—O)$_n$-(substituted or unsubstituted alkylene)-C(O)—, —C(O)-(substituted or unsubstituted alkylene)-C(O)—NH-(substituted or unsubstituted alkylene)-, —C(O)—, —C(O)-(substituted or unsubstituted alkylene)-, -(substituted or unsubstituted alkylene)-C(O)—, —C(O)N($R^{L1}$)—, —C(O)N($R^{L1}$)-(substituted or unsubstituted alkylene)-, -(substituted or unsubstituted alkylene)-C(O)N($R^{L1}$), -(substituted or unsubstituted alkylene)-C(O)N$R^{L1}$-(substituted or unsubstituted alkylene)-, —OC(O)N($R^{L1}$)—, —OC(O)N($R^{L1}$)-(substituted or unsubstituted alkylene)-, -(substituted or unsubstituted alkylene)-OC(O)N($R^{L1}$)—, —N($R^H$)C(O)—, —N$R^{L1}$C(O)-(substituted or unsubstituted alkylene)-, -(substituted or unsubstituted alkylene)-N$R^{L1}$C(O)—, —S—, —S-(substituted or unsubstituted alkylene)-, —S(O)$_k$—, —S(O)$_k$(alkylene or substituted alkylene)-, —C(S)—, —C(S)-(substituted or unsubstituted alkylene)-, —CSN($R^{L1}$)—, —CSN($R^{L1}$)-(substituted or unsubstituted alkylene)-, —N($R^{L1}$)C(O)O—, -(substituted or unsubstituted alkylene)-O— N=C$R^{L1}$—, -(substituted or unsubstituted alkylene)-S(O)$_k$-(substituted or unsubstituted alkylene)-S—, -(substituted or unsubstituted alkylene)-S—S—, —S(O)$_k$N($R^{L1}$)—, —N($R^{L1}$)C(O)N($R^{L1}$)—, —N($R^{L1}$)C(S)N($R^{L1}$)—, —N($R^{L1}$)S(O)$_k$N($R^{L1}$)—, —N($R^{L1}$)—N=, —C($R^{L1}$)=N—, —C($R^{L1}$)=N—N($R^{L1}$)—, —C($R^{L1}$)=N—N=, —C($R^{L1}$)$_2$—N=N—, and —C($R^{L1}$)$_2$—N($R^{L1}$)—N($R^{L1}$)—; wherein the bond on the left side of $L^1$, as drawn, is bound to the 8-membered ring of the compound of formula (II) or the compound of formula (III) and the bond on the right side of the $L^1$, as drawn, is bound to $X^1$;

$Y^1$ is a bond, —NH—, —O—, —S—, —NH($Y^{1a}$)—, —O($Y^{1a}$)— or —S($Y^{1a}$)—;

$Y^2$ is a bond, —C(=O)—, —S(=O)$_2$—, —C(=O)$Y^{2a}$—, —S(=O)$_2Y^{2a}$;

$Y^{1a}$ and $Y^{2a}$ are each independently $Y^3$ or $Y^3$NH—

$Y^3$ is substituted or unsubstituted $C_{1-10}$alkyl or —(CH$_2$CH$_2$O)$_{1-10}$—; and n is an integer from 1 to 30;

k is 1, 2, or 3;

each $R^{L1}$ is independently hydrogen or substituted or unsubstituted alkyl; and $R^4$, $R^5$, $R^6$, and $R^7$ are each independently hydrogen, halo, or substituted or unsubstituted alkyl;

wherein the conjugate has a molecular weight of at least 1.3 times greater than the conjugate molecular weight when LDAO is not used.

In some embodiments, heterocycle-containing conjugate is a conjugate of formulae (XXII-A) or (XXII-B):

LDAO is not used. In some embodiments, the conjugate has a molecular weight of at least 1.5 times greater than the conjugate molecular weight when LDAO is not used. In some embodiments, the conjugate has a molecular weight of at least 1.6 times greater than the conjugate molecular weight when LDAO is not used. In some embodiments, the conjugate has a molecular weight of at least 1.7 times greater than the conjugate molecular weight when LDAO is not used. In some embodiments, the conjugate has a molecular weight of at least 1.8 times greater than the conjugate molecular weight when LDAO is not used. In some embodiments, the conjugate has a molecular weight of at least 1.9 times greater than the conjugate molecular weight when LDAO is not used. In some embodiments, the conjugate has a molecular weight of at least 2.0 times greater than the conjugate molecular weight when LDAO is not used. In some embodiments, the conjugate has a molecular weight of at least 2.1 times greater than the conjugate molecular weight when LDAO is not used. In some embodiments, the conjugate has a molecular weight of at least 2.2 times greater than the conjugate molecular weight when LDAO is not used. In some embodiments, the conjugate has a molecular weight of at least 2.3 times greater than the conjugate molecular weight when LDAO is not used. In some embodiments, the conjugate has a molecular weight of at least 2.4 times greater than the conjugate molecular weight when LDAO is not used. In some embodiments, the conjugate has a molecular weight of at least 2.5 times greater than the conjugate molecular weight when LDAO is not used.

In some embodiments, the conjugate comprises a first polypeptide and one or more PS3, wherein the first polypeptide is CRM-pAMF6 mutant, and wherein the conjugate (XXII-A)

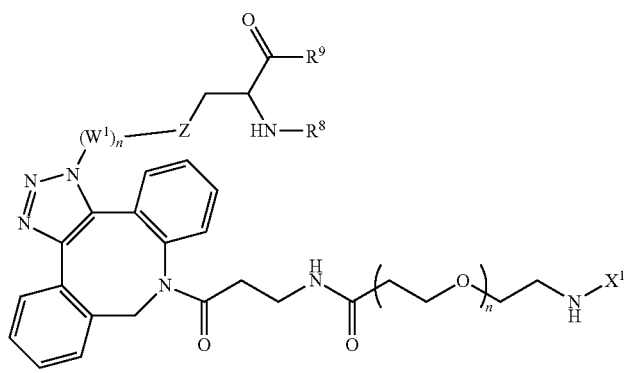

or (XXII-B)

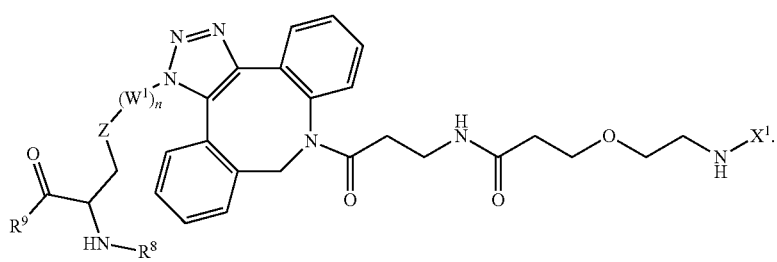

In some embodiments, the conjugate has a molecular weight of at least 1.3 times greater than the conjugate molecular weight when LDAO is not used. In some embodiments, the conjugate has a molecular weight of at least 1.4 times greater than the conjugate molecular weight when has a molecular weight of at least 1.6 times greater the conjugate molecular weight when LDAO is not used. In some embodiments, the conjugate comprises a first polypeptide and one or more PS5, wherein the first polypeptide is CRM-pAMF6 mutant, and wherein the conjugate has a molecular weight of at least 2.2 times greater than the conjugate molecular weight when LDAO is not used. In some embodiments, the conjugate comprises a first polypeptide and one or more PS18, wherein the first polypeptide is CRM-pAMF6 mutant, and wherein the conjugate has a molecular weight of at least 2.2 times greater than the conjugate molecular weight when LDAO is not used. In some embodiments, the conjugate comprises a first polypeptide and one or more PS19A, wherein the first polypeptide is CRM-pAMF6 mutant, and wherein the conjugate has a molecular weight of at least 1.5 times greater than the conjugate molecular weight when LDAO is not used.

In some embodiments is a conjugate comprising a first polypeptide and antigen, wherein the first polypeptide is selected from the group consisting of SEQ ID NO:1 and SEQ ID NO:2. In certain embodiments, the first polypeptide is a polypeptide of SEQ ID NO:1. In certain embodiments, the first polypeptide is a polypeptide with at least 80% sequence identity to SEQ ID NO:1. In certain embodiments, the first polypeptide is a polypeptide with at least 85% sequence identity to SEQ ID NO:1. In certain embodiments, the first polypeptide is a polypeptide with at least 90% sequence identity to SEQ ID NO:1. In certain embodiments, the first polypeptide is a polypeptide with at least 95% sequence identity to SEQ ID NO:1. In some embodiments is a conjugate comprising a first polypeptide and antigen, wherein the first polypeptide is a polypeptide of SEQ ID NO:2. In certain embodiments, the first polypeptide is a polypeptide with at least 80% sequence identity to SEQ ID NO:2. In certain embodiments, the first polypeptide is a polypeptide with at least 85% sequence identity to SEQ ID NO:2. In certain embodiments, the first polypeptide is a polypeptide with at least 90% sequence identity to SEQ ID NO:2. In certain embodiments, the first polypeptide is a polypeptide with at least 95% sequence identity to SEQ ID NO:2.

In some embodiments is a conjugate comprising a first polypeptide and antigen, wherein the first polypeptide is selected from the group consisting of SEQ ID NO:1 and SEQ ID NO:2, and the antigen is a polysaccharide. In certain embodiments, the first polypeptide is a polypeptide of SEQ ID NO:1, and the antigen is a polysaccharide. In certain embodiments, the first polypeptide is a polypeptide with at least 80% sequence identity to SEQ ID NO:1, and the antigen is a polysaccharide. In certain embodiments, the first polypeptide is a polypeptide with at least 85% sequence identity to SEQ ID NO:1, and the antigen is a polysaccharide. In certain embodiments, the first polypeptide is a polypeptide with at least 90% sequence identity to SEQ ID NO:1, and the antigen is a polysaccharide. In certain embodiments, the first polypeptide is a polypeptide with at least 95% sequence identity to SEQ ID NO:1, and the antigen is a polysaccharide. In some embodiments is a conjugate comprising a first polypeptide and antigen, wherein the first polypeptide is a polypeptide of SEQ ID NO:2, and the antigen is a polysaccharide. In certain embodiments, the first polypeptide is a polypeptide with at least 80% sequence identity to SEQ ID NO:2, and the antigen is a polysaccharide. In certain embodiments, the first polypeptide is a polypeptide with at least 85% sequence identity to SEQ ID NO:2, and the antigen is a polysaccharide. In certain embodiments, the first polypeptide is a polypeptide with at least 90% sequence identity to SEQ ID NO:2, and the antigen is a polysaccharide. In certain embodiments, the first polypeptide is a polypeptide with at least 95% sequence identity to SEQ ID NO:2, and the antigen is a polysaccharide.

In some embodiments is a conjugate comprising a first polypeptide and antigen, wherein the first polypeptide is a polypeptide of SEQ ID NO:3. In certain embodiments, the first polypeptide is a polypeptide with at least 80% sequence identity to SEQ ID NO:3. In certain embodiments, the first polypeptide is a polypeptide with at least 85% sequence identity to SEQ ID NO:3. In certain embodiments, the first polypeptide is a polypeptide with at least 90% sequence identity to SEQ ID NO:3. In certain embodiments, the first polypeptide is a polypeptide with at least 95% sequence identity to SEQ ID NO:3.

In some embodiments is a conjugate comprising a first polypeptide and antigen, wherein the first polypeptide is a polypeptide of SEQ ID NO:3, and the antigen is a polysaccharide. In certain embodiments, the first polypeptide is a polypeptide with at least 80% sequence identity to SEQ ID NO:3, and the antigen is a polysaccharide. In certain embodiments, the first polypeptide is a polypeptide with at least 85% sequence identity to SEQ ID NO:3, and the antigen is a polysaccharide. In certain embodiments, the first polypeptide is a polypeptide with at least 90% sequence identity to SEQ ID NO:3, and the antigen is a polysaccharide. In certain embodiments, the first polypeptide is a polypeptide with at least 95% sequence identity to SEQ ID NO:3, and the antigen is a polysaccharide.

In some embodiments is a conjugate comprising a first polypeptide and antigen, wherein the first polypeptide is a polypeptide of SEQ ID NO:10. In certain embodiments, the first polypeptide is a polypeptide with at least 80% sequence identity to SEQ ID NO:10. In certain embodiments, the first polypeptide is a polypeptide with at least 85% sequence identity to SEQ ID NO:10. In certain embodiments, the first polypeptide is a polypeptide with at least 90% sequence identity to SEQ ID NO:10. In certain embodiments, the first polypeptide is a polypeptide with at least 95% sequence identity to SEQ ID NO:10.

In some embodiments is a conjugate comprising a first polypeptide and antigen, wherein the first polypeptide is a polypeptide of SEQ ID NO:10, and the antigen is a polysaccharide. In certain embodiments, the first polypeptide is a polypeptide with at least 80% sequence identity to SEQ ID NO:10, and the antigen is a polysaccharide. In certain embodiments, the first polypeptide is a polypeptide with at least 85% sequence identity to SEQ ID NO:10, and the antigen is a polysaccharide. In certain embodiments, the first polypeptide is a polypeptide with at least 90% sequence identity to SEQ ID NO:10, and the antigen is a polysaccharide. In certain embodiments, the first polypeptide is a polypeptide with at least 95% sequence identity to SEQ ID NO:10, and the antigen is a polysaccharide.

In some embodiments is a conjugate comprising a first polypeptide and antigen, wherein the first polypeptide is a polypeptide of SEQ ID NO:11. In certain embodiments, the first polypeptide is a polypeptide with at least 80% sequence identity to SEQ ID NO:11. In certain embodiments, the first polypeptide is a polypeptide with at least 85% sequence identity to SEQ ID NO:11. In certain embodiments, the first polypeptide is a polypeptide with at least 90% sequence identity to SEQ ID NO:11. In certain embodiments, the first polypeptide is a polypeptide with at least 95% sequence identity to SEQ ID NO:11.

In some embodiments is a conjugate comprising a first polypeptide and antigen, wherein the first polypeptide is a polypeptide of SEQ ID NO:11, and the antigen is a polysaccharide. In certain embodiments, the first polypeptide is a polypeptide with at least 80% sequence identity to SEQ ID NO:11, and the antigen is a polysaccharide. In certain embodiments, the first polypeptide is a polypeptide with at least 85% sequence identity to SEQ ID NO:11, and the antigen is a polysaccharide. In certain embodiments, the first polypeptide is a polypeptide with at least 90% sequence identity to SEQ ID NO:11, and the antigen is a polysaccharide. In certain embodiments, the first polypeptide is a polypeptide with at least 95% sequence identity to SEQ ID NO:11, and the antigen is a polysaccharide.

In some embodiments is a conjugate comprising a first polypeptide and antigen, wherein the first polypeptide is a polypeptide of SEQ ID NO:13, and the antigen is a polysaccharide. In certain embodiments, the first polypeptide is a polypeptide with at least 80% sequence identity to SEQ ID NO:13, and the antigen is a polysaccharide. In certain embodiments, the first polypeptide is a polypeptide with at least 85% sequence identity to SEQ ID NO:13, and the antigen is a polysaccharide. In certain embodiments, the first polypeptide is a polypeptide with at least 90% sequence identity to SEQ ID NO:13, and the antigen is a polysaccharide. In certain embodiments, the first polypeptide is a polypeptide with at least 95% sequence identity to SEQ ID NO:13, and the antigen is a polysaccharide.

In some embodiments is a conjugate comprising a first polypeptide and antigen, wherein the first polypeptide comprises at least one nnAAr of Formula (IV). In certain embodiments, the first polypeptide comprises one nnAAr of Formula (IV). In certain embodiments, the first polypeptide comprises 1-2 nnAAr of Formula (IV). In certain embodiments, $R^1$ is a polypeptide comprising 2-4 nnAAr of Formula (IV). In certain embodiments, the first polypeptide comprises 4-6 nnAAr of Formula (IV). In certain embodiments, the first polypeptide comprises 6-8 nnAAr of Formula (IV). In certain embodiments, the first polypeptide comprises 6 nnAAr of Formula (IV). In certain embodiments, the first polypeptide comprises 1-10 nnAAr of Formula (IV). In certain embodiments, the first polypeptide comprises 5-10 nnAAr of Formula (IV). In certain embodiments, the first polypeptide comprises greater than 10 nnAAr of Formula (IV).

In some embodiments is a conjugate comprising a first polypeptide and antigen, wherein the nnAAr of Formula (IV) replaces a lysine residue in the polypeptide comprising at least one non-natural amino acid. In some embodiments, $R^1$ is a polypeptide comprising at least one nnAAr having a molecular weight between 1 and 1000 kDa. In certain embodiments, $R^1$ is a polypeptide comprising at least one nnAAr having a molecular weight between 1 and 500 kDa. In some embodiments, $R^1$ is a polypeptide comprising at least one nnAAr having a molecular weight between 1 and 250 kDa. In some embodiments, $R^1$ is a polypeptide comprising at least one nnAAr having a molecular weight between 1 and 100 kDa. In some embodiments, $R^1$ is a polypeptide comprising at least one nnAAr having a molecular weight between 1 and 50 kDa. In some embodiments, $R^1$ is a polypeptide comprising at least one nnAAr having a molecular weight between 50 and 100 kDa. In some embodiments, $R^1$ is a polypeptide comprising at least one nnAAr having a molecular weight between 50 and 60 kDa. In some embodiments, $R^1$ is a polypeptide comprising at least one nnAAr having a molecular weight of at least 500 kDa.

In some embodiments is a conjugate comprising a first polypeptide and antigen, wherein the azido moiety of the nnAAr is conjugated to the alkyne of formula II' or III' in the presence of LDAO. In some embodiments is a conjugate comprising a first polypeptide and antigen, wherein the azido moiety of the nnAAr is conjugated to the alkyne of formula II' in the presence of LDAO. In some embodiments is a conjugate comprising a first polypeptide and antigen, wherein the azido moiety of the nnAAr is conjugated to the alkyne of formula III' in the presence of LDAO.

In some embodiments is a conjugate comprising a first polypeptide and antigen, wherein the antigen is a compound of the formula -A-$L^2$-$X^2$, and $X^2$ is a polysaccharide or second polypeptide. In certain embodiments is a conjugate comprising a first polypeptide and antigen, wherein the antigen is a compound of the formula -A-$L^2$-$X^2$, and $X^2$ is a polysaccharide. In some embodiments is a conjugate comprising a first polypeptide and antigen, wherein the antigen is a compound of the formula -A-$L^2$-$X^2$, and $X^2$ is a second polypeptide.

In some embodiments, an antigen is a polysaccharide. In certain embodiments, the polysaccharide or antigen is a *Streptococcus pneumoniae* capsular polysaccharide serotype selected from 1, 2, 3, 4, 5, 6A, 6B, 7F, 7A, 7B, 7C, 8, 9A, 9L, 9N, 9V, 10F, 10A, 10B, 10C, 11F, 11A, 11B, 11C, 11D, 12F, 12A, 12B, 13, 14, 15F, 15A, 15B, 15C, 16F, 16A, 17F, 17A, 18F, 18A, 18B, 18C, 19F, 19A, 19B, 19C, 20, 21, 22F, 22A, 23F, 23A, 23B, 24F, 24A, 24B, 25F, 25A, 27, 28F, 28A, 29, 31, 32F, 32A, 33F, 33A, 33B, 33C, 33D, 34, 35F, 35A, 35B, 35C, 36, 37, 38, 39, 40, 41F, 41A, 42, 43, 44, 45, 46, 47F, 47A, and 48 (Henrichsen *J Clin Microbiol* 1995; 33:2759-2762). A subset of these serotypes are commonly responsible for bacterial infection, which include serotypes 1, 2, 3, 4, 5, 6A, 6B, 7F, 8, 9V, 9N, 10A, 11A, 12F, 13, 14, 15B, 16, 17F, 18C, 19A, 19F, 20, 22F, 23F, 24F, 31, and 33F. Serotypes 6C, 7C, 15A, 15C, 16F, 23A, 23B, 31, 34, 35B, 35F, 37 and 38 have also become of clinical concern, as have serotypes 20A, 20B and 24B. In another embodiment, the antigen is a *Streptococcus pneumoniae* capsular polysaccharide selected from serotypes 1, 2, 3, 4, 5, 6A, 6B, 7F, 8, 9V, 9N, 10A, 11A, 12F, 13, 14, 15B, 16, 17F, 18C, 19A, 19F, 20, 22F, 23F, 24F, 31, and 33F. In a another embodiment, the antigen is a *Streptococcus pneumoniae* capsular polysaccharide selected from serotypes 6C, 7C, 15A, 15C, 16F, 23A, 23B, 31, 34, 35B, 35F, 37 and 38. The embodiments described herein can also additionally comprise one or more of *Streptococcus pneumoniae* capsular polysaccharide selected from serotypes 20A, 20B and 24B.

In some embodiments, the antigen is a *Streptococcus pneumoniae* capsular polysaccharide selected from serotypes 1, 2, 3, 4, 5, 6A, 6B, 7F, 8, 9V, 9N, 10A, 11A, 12F, 14, 15B, 17F, 18C, 19A, 19F, 20B, 22F, 23F, and 33F. In some embodiments, the antigen is a *Streptococcus pneumoniae* capsular polysaccharide selected from serotypes 1, 2, 3, 4, 5, 6A, 6B, 7C, 7F, 8, 9V, 9N, 10A, 11A, 12F, 14, 15A, 15B, 16F, 17F, 18C, 19A, 19F, 20B, 22F, 23A, 23B, 23F, 31, 33F, and 35B.

Polysaccharides of *Streptococcus pneumoniae* can be abbreviated with "PS." For example, *Streptococcus pneumoniae* polysaccharide serotype 1 can be abbreviated as "PS1."

In some embodiments, the conjugate has a molecular weight of at least 400 kDa. In certain embodiments, the conjugate can have a molecular weight of at least 600 kDa, at least 800 kDa, at least 900 kDa, or at least 1 MDa e.g. between 1-5MDa.

In some embodiments, the polysaccharide is a Group A *Streptococcus* (GAS) polysaccharide, such as the group A carbohydrate (GAC). The GAC is composed of a polyrhamnose backbone with an immunodominant GlcNAc side chain and is present on the surface of strains of all GAS serotypes irrespective of M type and has been examined as a GAS vaccine candidate. Therefore, in some embodiments, the conjugate polysaccharide is a variant of the GAC that lacks the immunodominant GlcNAc side chain (See e.g., International PCT Publication No. WO 2013/020090). In some embodiments, the conjugate polysaccharide is a GAC comprising a polyrhamanose core. In some embodiments, the conjugate polysaccharide has an average molecular weight of about 3 kDa to about 10 kDa, about 5 kDa to about 10 kDa, about 9 kDa to about 10 kDa, about 9 kDa to about 10 kDa, about 3 kDa to about 9 kDa, about 3 kDa to about 7 kDa, about 3 kDa to about 5 kDa, about 5 kDa to about 9 kDa, or about 5 kDa to about 7 kDa. In some embodiments, the conjugate polysaccharide has an average molecular weight of about 3 kDa, 4 kDa, 5 kDa, 6 kDa, 7 kDa, 8 kDa, 9 kDa, or about 10 kDa. In some embodiments, the conjugate polysaccharide is a tetramer, a pentamer, a hexamer, a septamer, an octamer, a nonomer, or a decamer polysaccharide.

In some embodiments, the polysaccharide is an O-antigen *Shigella* polysaccharide. In certain embodiments, the O-antigen *Shigella* polysaccharide is selected from serotypes 1a, 1b, 2a, 2b, 3b, 4a, 4b, 5a, 5b, 6, 7a, 7b, or combinations thereof. In certain embodiments, the O-antigen *Shigella* polysaccharide is from *Shigella flexneri*. In certain embodiments, the O-antigen *Shigella* polysaccharide is from *Shigella sonnei*. In certain embodiments, the O-antigen *Shigella* polysaccharide is from *Shigella dysenteriae*.

In some embodiments, the antibody titer upon challenge is greater for the conjugate compared to antibody titer upon challenge of a conjugate of the same formula where conjugation of the first polypeptide and the antigen is performed in the absence of LDAO, when tested under equivalent challenge conditions. In certain embodiments, the antibody titer upon challenge is between 10% to 50% greater. In certain embodiments, the antibody titer upon challenge is between 50% to 100% greater. In certain embodiments, the antibody titer upon challenge is between 100% to 200% greater. In certain embodiments, the antibody titer upon challenge is between 400% to 500% greater. In certain embodiments, the antibody titer upon challenge is more than 500% greater.

Table 1 shows nine exemplary polypeptides of this disclosure. X=site of nnAA incorporation.

TABLE 1

Exemplary Polypeptides

| SEQ ID | Name/Description | Amino acid sequence |
|---|---|---|
| 1 | CRM197 | GADDVVDSSKSFVMENFSSYHGTKPGYVDSIQKGIQKPKSGTQGNY DDDWKEFYSTDNKYDAAGYSVDNENPLSGKAGGVVKVTYPGLTK VLALKVDNAETIKKELGLSLTEPLMEQVGTEEFIKRFGDGASRVVLS LPFAEGSSSVEYINNWEQAKALSVELEINFETRGKRGQDAMYEYMA QACAGNRVRRSVGSSLSCINLDWDVIRDKTKTKIESLKEHGPIKNKM SESPNKTVSEEKAKQYLEEFHQTALEHPELSELKTVTGTNPVFAGAN YAAWAVNVAQVIDSETADNLEKTTAALSILPGIGSVMGIADGAVHH NTEEIVAQSIALSSLMVAQAIPLVGELVDIGFAAYNFVESIINLFQVVH NSYNRPAYSPGHKTQPFLHDGYAVSWNTVEDSIIRTGFQGESGHDIK ITAENTPLPIAGVLLPTIPGKLDVNKSKTHISVNGRKIRMRCRAIDGD VTFCRPKSPVYVGNGVHANLHVAFHRSSSEKIHSNEISSDSIGVLGYQ KTVDHTKVNSKLSLFFEIKS |
| 2 | CRM-pAMF6 mutant<br>X = pAMF | MGADDVVDSSKSFVMENFSSYHGTKPGYVDSIQXGIQKPKSGTQGN YDDDWKEFYSTDNKYDAAGYSVDNENPLSGKAGGVVKVTYPGLT KVLALKVDNAETIKKELGLSLTEPLMEQVGTEEFIKRFGDGASRVVL SLPFAEGSSSVEYINNWEQAKALSVELEINFETRGKRGQDAMYEYM AQACAGNRVRNSVGSSLSCINLDWDVIRDXTKTKIESLKEHGPIKNK MSESPNKTVSEEKAXQYLEEFHQTALEHPELSELKTVTGTNPVFAGA NYAAWAVNVAQVIDSETADNLEKTTAALSILPGIGSVMGIADGAVH HNTEEIVAQSIALSSLMVAQAIPLVGELVDIGFAAYNFVESIINLFQVV HNSYNRPAYSPGHXTQPFLHDGYAVSWNTVEDSIIRTGFQGESGHDI KITAENTPLPIAGVLLPTIPGKLDVNKSKTHISVNGRKIRMRCRAIDG DVTFCRPKSPVYVGNGVHANLHVAFHRSSSEKIHSNEISSDSIGVLGY QKTVDHTKVNSXLSLFFEIKS |
| 3 | WT IpaB | MHNVNTTTTGLSLAKILASTELGDNTIQAGNDAANKLFSLTIADLTA NKNINTTNAHSTSNILIPELKAPKSLNASSQLTLLIGNLIQILGEKSLTA LTNKITAWKSQQQARQQKNLEFSDKINTLLSETEGLTRDYEKQINKL KNADSKIKDLENKINQIQTRLSELDPDSPEKKKLSREEIQLTIKKDAA VKDRTLIEQKTLSIHSKLTDKSMQLEKEIDSFSAFSNTASAEQLSTQQ KSLTGLASVTQLMATFIQLVGKNNEESLKNDLALFQSLQESRKTEME RKSDEYAAEVRKAEELNRVMGCVGKILGALLTIVSVVAAAFSGGAS LALADVGLALMVTDAIVQAATGNSFMEQALNPIMKAVIEPLIKLLSD AFTKMLEGLGVDSKKAKMIGSILGAIAGALVLVAAVVLVATVGKQ AAAKLAENIGKIIGKTLTDLIPKFLKNFSSQLDDLITNAVARLNKFLG AAGDEVISKQIISTHLNQAVLLGESVNSATQAGGSVASAVFQNSAST NLADLTLSKYQVEQLSKYISEAIEKFGQLQEVIADLLASMSNSQANR TDVAKAILQQTTA |
| 4 | IpaB Mutant 1<br>K289/K368/K395 | MHNVNTTTTGLSLAKILASTELGDNTIQAGNDAANKLFSLTIADLTA NKNINTTNAHSTSNILIPELKAPKSLNASSQLTLLIGNLIQILGEKSLTA LTNKITAWKSQQQARQQKNLEFSDKINTLLSETEGLTRDYEKQINKL KNADSKIKDLENKINQIQTRLSELDPDSPEKKKLSREEIQLTIKKDAA VKDRTLIEQKTLSIHSKLTDKSMQLEKEIDSFSAFSNTASAEQLSTQQ KSLTGLASVTQLMATFIQLVGKNNEESLKNDLALFQSLQESRKTEME RXSDEYAAEVRKAEELNRVMGCVGKILGALLTIVSVVAAAFSGGAS LALADVGLALMVTDAIVQAATGNSFMEQALNPIMXAVIEPLIKLLSD |

TABLE 1-continued

Exemplary Polypeptides

| SEQ ID | Name/Description | Amino acid sequence |
|---|---|---|
| | | AFTKMLEGLGVDSKXAKMIGSILGAIAGALVLVAAVVLVATVGKQ<br>AAAKLAENIGKIIGKTLTDLIPKFLKNFSSQLDDLITNAVARLNKFLG<br>AAGDEVISKQIISTHLNQAVLLGESVNSATQAGGSVASAVFQNSAST<br>NLADLTLSKYQVEQLSKYISEAIEKFGQLQEVIADLLASMSNSQANR<br>TDVAKAILQQTTA |
| 5 | IpaB Mutant 2<br>K299/K395/K436 | MHNVNTTTTGLSLAKILASTELGDNTIQAGNDAANKLFSLTIADLTA<br>NKNINTTNAHSTSNILIPELKAPKSLNASSQLTLLIGNLIQILGEKSLTA<br>LTNKITAWKSQQQARQQKNLEFSDKINTLLSETEGLTRDYEKQINKL<br>KNADSKIKDLENKINQIQTRLSELDPDSPEKKKLSREEIQLTIKKDAA<br>VKDRTLIEQKTLSIHSKLTDKSMQLEKEIDSFSAFSNTASAEQLSTQQ<br>KSLTGLASVTQLMATFIQLVGKNNEESLKNDLALFQSLQESRKTEME<br>RKSDEYAAEVRXAEELNRVMGCVGKILGALLTIVSVVAAAFSGGAS<br>LALADVGLALMVTDAIVQAATGNSFMEQALNPIMKAVIEPLIKLLSD<br>AFTKMLEGLGVDSKXAKMIGSILGAIAGALVLVAAVVLVATVGKQ<br>AAAKLAENIGXIIGKTLTDLIPKFLKNFSSQLDDLITNAVARLNKFLG<br>AAGDEVISKQIISTHLNQAVLLGESVNSATQAGGSVASAVFQNSAST<br>NLADLTLSKYQVEQLSKYISEAIEKFGQLQEVIADLLASMSNSQANR<br>TDVAKAILQQTTA |
| 6 | IpaB Mutant 3<br>K299/K368/K395 | MHNVNTTTTGLSLAKILASTELGDNTIQAGNDAANKLFSLTIADLTA<br>NKNINTTNAHSTSNILIPELKAPKSLNASSQLTLLIGNLIQILGEKSLTA<br>LTNKITAWKSQQQARQQKNLEFSDKINTLLSETEGLTRDYEKQINKL<br>KNADSKIKDLENKINQIQTRLSELDPDSPEKKKLSREEIQLTIKKDAA<br>VKDRTLIEQKTLSIHSKLTDKSMQLEKEIDSFSAFSNTASAEQLSTQQ<br>KSLTGLASVTQLMATFIQLVGKNNEESLKNDLALFQSLQESRKTEME<br>RKSDEYAAEVRXAEELNRVMGCVGKILGALLTIVSVVAAAFSGGAS<br>LALADVGLALMVTDAIVQAATGNSFMEQALNPIMXAVIEPLIKLLSD<br>AFTKMLEGLGVDSKXAKMIGSILGAIAGALVLVAAVVLVATVGKQ<br>AAAKLAENIGKIIGKTLTDLIPKFLKNFSSQLDDLITNAVARLNKFLG<br>AAGDEVISKQIISTHLNQAVLLGESVNSATQAGGSVASAVFQNSAST<br>NLADLTLSKYQVEQLSKYISEAIEKFGQLQEVIADLLASMSNSQANR<br>TDVAKAILQQTTA |
| 7 | IpaB Mutant 4<br>K289/K368/K395/<br>K436 | MHNVNTTTTGLSLAKILASTELGDNTIQAGNDAANKLFSLTIADLTA<br>NKNINTTNAHSTSNILIPELKAPKSLNASSQLTLLIGNLIQILGEKSLTA<br>LTNKITAWKSQQQARQQKNLEFSDKINTLLSETEGLTRDYEKQINKL<br>KNADSKIKDLENKINQIQTRLSELDPDSPEKKKLSREEIQLTIKKDAA<br>VKDRTLIEQKTLSIHSKLTDKSMQLEKEIDSFSAFSNTASAEQLSTQQ<br>KSLTGLASVTQLMATFIQLVGKNNEESLKNDLALFQSLQESRKTEME<br>RXSDEYAAEVRKAEELNRVMGCVGKILGALLTIVSVVAAAFSGGAS<br>LALADVGLALMVTDAIVQAATGNSFMEQALNPIMXAVIEPLIKLLSD<br>AFTKMLEGLGVDSKXAKMIGSILGAIAGALVLVAAVVLVATVGKQ<br>AAAKLAENIGXIIGKTLTDLIPKFLKNFSSQLDDLITNAVARLNKFLG<br>AAGDEVISKQIISTHLNQAVLLGESVNSATQAGGSVASAVFQNSAST<br>NLADLTLSKYQVEQLSKYISEAIEKFGQLQEVIADLLASMSNSQANR<br>TDVAKAILQQTTA |
| 8 | IpaB Mutant 5<br>K299/K395/K436/<br>K470 | MHNVNTTTTGLSLAKILASTELGDNTIQAGNDAANKLFSLTIADLTA<br>NKNINTTNAHSTSNILIPELKAPKSLNASSQLTLLIGNLIQILGEKSLTA<br>LTNKITAWKSQQQARQQKNLEFSDKINTLLSETEGLTRDYEKQINKL<br>KNADSKIKDLENKINQIQTRLSELDPDSPEKKKLSREEIQLTIKKDAA<br>VKDRTLIEQKTLSIHSKLTDKSMQLEKEIDSFSAFSNTASAEQLSTQQ<br>KSLTGLASVTQLMATFIQLVGKNNEESLKNDLALFQSLQESRKTEME<br>RKSDEYAAEVRXAEELNRVMGCVGKILGALLTIVSVVAAAFSGGAS<br>LALADVGLALMVTDAIVQAATGNSFMEQALNPIMKAVIEPLIKLLSD<br>AFTKMLEGLGVDSKXAKMIGSILGAIAGALVLVAAVVLVATVGKQ<br>AAAKLAENIGXIIGKTLTDLIPKFLKNXSSQLDDLITNAVARLNXFLG<br>AAGDEVISKQIISTHLNQAVLLGESVNSATQAGGSVASAVFQNSAST<br>NLADLTLSKYQVEQLSKYISEAIEKFGQLQEVIADLLASMSNSQANR<br>TDVAKAILQQTTA |
| 9 | IpaB Mutant 6<br>K299/K368/K395/<br>K436 | MHNVNTTTTGLSLAKILASTELGDNTIQAGNDAANKLFSLTIADLTA<br>NKNINTTNAHSTSNILIPELKAPKSLNASSQLTLLIGNLIQILGEKSLTA<br>LTNKITAWKSQQQARQQKNLEFSDKINTLLSETEGLTRDYEKQINKL<br>KNADSKIKDLENKINQIQTRLSELDPDSPEKKKLSREEIQLTIKKDAA<br>VKDRTLIEQKTLSIHSKLTDKSMQLEKEIDSFSAFSNTASAEQLSTQQ<br>KSLTGLASVTQLMATFIQLVGKNNEESLKNDLALFQSLQESRKTEME<br>RKSDEYAAEVRXAEELNRVMGCVGKILGALLTIVSVVAAAFSGGAS<br>LALADVGLALMVTDAIVQAATGNSFMEQALNPIMXAVIEPLIKLLSD<br>AFTKMLEGLGVDSKXAKMIGSILGAIAGALVLVAAVVLVATVGKQ<br>AAAKLAENIGXIIGKTLTDLIPKFLKNFSSQLDDLITNAVARLNKFLG<br>AAGDEVISKQIISTHLNQAVLLGESVNSATQAGGSVASAVFQNSAST<br>NLADLTLSKYQVEQLSKYISEAIEKFGQLQEVIADLLASMSNSQANR<br>TDVAKAILQQTTA |

TABLE 1-continued

Exemplary Polypeptides

| SEQ ID | Name/Description | Amino acid sequence |
|---|---|---|
| 10 | SpyAD-WT | MHHHHHHGSGENLYFQGQVKADDRASGETKASNTHDDSLPKPETIQ<br>EAKATIDAVEKTLSQQKAELTELATALTKTTAEINHLKEQQDNEQK<br>ALTSAQEIYTNTLASSEETLLAQGAEHQRELTATETELHNAQADQHS<br>KETALSEQKASISAETTRAQDLVEQVKTSEQNIAKLNAMISNPDAITK<br>AAQTANDNTKALSSELEKAKADLENQKAKVKKQLTEELAAQKAAL<br>AEKEAELSRLKSSAPSTQDSIVGNNTMKAPQGYPLEELKKLEASGYI<br>GSASYNNYYKEHADQIIAKASPGNQLNQYQDIPADRNRFVDPDNLT<br>PEVQNELAQFAAHMINSVRRQLGLPPVTVTAGSQEFARLLSTSYKKT<br>HGNTRPSFVYGQPGVSGHYGVGPHDKTIIEDSAGASGLIRNDDNMY<br>ENIGAFNDVHTVNGIKRGIYDSIKYMLFTDHLHGNTYGHAINFLRVD<br>KHNPNAPVYLGFSTSNVGSLNEHFVMFPESNIANHQRFNKTPIKAVG<br>STKDYAQRVGTVSDTIAAIKGKVSSLENRLSAIHQEADIMAAQAKVS<br>QLQGKLASTLKQSDSLNLQVRQLNDTKGSLRTELLAAKAKQAQLEA<br>TRDQSLAKLASLKAALHQTEALAEQAAARVTALVAKKAHLQYLRD<br>FKLNPNRLQVIRERIDNTKQDLAKTTSSLLNAQEALAALQAKQSSLE<br>ATIATTEHQLTLLKTLANEKEYRHLDEDIATVPDLQVAPPLTGVKPL<br>SYSKIDTTPLVQEMVKETKQLLEASARLAAENTSLVAEALVGQTSE<br>MVASNAIVSKITSSITQPSSKTSYGSGSSTTSNLISDVDESTQR |
| 11 | Protein D | GCSSHSSNMANTQMKSDKIIIAHRGASGYLPEHTLESKALAFAQQAD<br>YLEQDLAMTKDGRLVVIHDHFLDGLTDVAKKFPHRHRKDGRYYVI<br>DFTLKEIQSLEMTENFETKDGKQAQVYPNRFPLWKSHFRIHTFEDEIE<br>FIQGLEKSTGKKVGIYPEIKAPWFHHQNGKDIAAETLKVLKKYGYD<br>KKTDMVYLQTFDFNELKRIKTELLPQMGMDLKLVQLIAYTDWKET<br>QEKDPKGYWVNYNYDWMFKP |
| 12 | SPYAD [33-849 FRAGMENT] WT W/O LEADER | QVKADDRASGETKASNTHDDSLPKPETIQEAKATIDAVEKTLSQQK<br>AELTELATALTKTTAEINHLKEQQDNEQKALTSAQEIYTNTLASSEET<br>LLAQGAEHQRELTATETELHNAQADQHSKETALSEQKASISAETTRA<br>QDLVEQVKTSEQNIAKLNAMISNPDAITKAAQTANDNTKALSSELEK<br>AKADLENQKAKVKKQLTEELAAQKAALAEKEAELSRLKSSAPSTQD<br>SIVGNNTMKAPQGYPLEELKKLEASGYIGSASYNNYYKEHADQIIAK<br>ASPGNQLNQYQDIPADRNRFVDPDNLTPEVQNELAQFAAHMINSVR<br>RQLGLPPVTVTAGSQEFARLLSTSYKKTHGNTRPSFVYGQPGVSGHY<br>GVGPHDKTIIEDSAGASGLIRNDDNMYENIGAFNDVHTVNGIKRGIY<br>DSIKYMLFTDHLHGNTYGHAINFLRVDKHNPNAPVYLGFSTSNVGS<br>LNEHFVMFPESNIANHQRFNKTPIKAVGSTKDYAQRVGTVSDTIAAI<br>KGKVSSLENRLSAIHQEADIMAAQAKVSQLQGKLASTLKQSDSLNL<br>QVRQLNDTKGSLRTELLAAKAKQAQLEATRDQSLAKLASLKAALH<br>QTEALAEQAAARVTALVAKKAHLQYLRDFKLNPNRLQVIRERIDNT<br>KQDLAKTTSSLLNAQEALAALQAKQSSLEATIATTEHQLTLLKTLAN<br>EKEYRHLDEDIATVPDLQVAPPLTGVKPLSYSKIDTTPLVQEMVKET<br>KQLLEASARLAAENTSLVAEALVGQTSEMVASNAIVSKITSSITQPSS<br>KTSYGSGSSTTSNLISDVDESTQR |
| 13 | SPYAD [33-849 FRAGMENT] NNAA (E.G., PAMF) W/O LEADER, WITH G OVERHANG FROM CLEAVAGE | GQVKADDRASGETKASNTHDDSLPKPETIQEAXATIDAVEKTLSQQ<br>KAELTELATALTKTTAEINHLKEQQDNEQKALTSAQEIYTNTLASSE<br>ETLLAQGAEHQRELTATETELHNAQADQHSKETALSEQKASISAETT<br>RAQDLVEQVKTSEQNIAKLNAMISNPDAITKAAQTANDNTKALSSEL<br>EKAKADLENQKAKVKKQLTEELAAQKAALAEKEAELSRLKSSAPST<br>QDSIVGNNTMKAPQGYPLEELKXLEASGYIGSASYNNYYKEHADQII<br>AKASPGNQLNQYQDIPADRNRFVDPDNLTPEVQNELAQFAAHMINS<br>VRRQLGLPPVTVTAGSQEFARLLSTSYKXTHGNTRPSFVYGQPGVSG<br>HYGVGPHDKTIIEDSAGASGLIRNDDNMYENIGAFNDVHTVNGIKRG<br>IYDSIKYMLFTDHLHGNTYGHAINFLRVDKHNPNAPVYLGFSTSNVG<br>SLNEHFVMFPESNIANHQRFNKTPIKAVGSTKDYAQRVGTVSDTIAA<br>IKGKVSSLENRLSAIHQEADIMAAQAKVSQLQGKLASTLKQSDSLNL<br>QVRQLNDTKGSLRTELLAAKAKQAQLEATRDQSLAKLASLKAALH<br>QTEALAEQAAARVTALVAKXAHLQYLRDFKLNPNRLQVIRERIDNT<br>KQDLAKTTSSLLNAQEALAALQAKQSSLEATIATTEHQLTLLKTLAN<br>EKEYRHLDEDIATVPDLQVAPPLTGVKPLSYSKIDTTPLVQEMVKET<br>KQLLEASARLAAENTSLVAEALVGQTSEMVASNAIVSKITSSITQPSS<br>KTSYGSGSSTTSNLISDVDESTQR |

EXEMPLARY EMBODIMENTS

Embodiment I-1. A method of preparing a heteroaryl-containing compound, the method comprising contacting an azide compound with an alkyne compound in the presence of lauryldimethylamine oxide (LDAO), water, and DMSO to form the heteroaryl-containing compound,
wherein the LDAO is at a concentration of up to 2% v/v;
wherein the azide compound is a compound of formula (I)

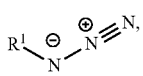

(I)

wherein the alkyne compound is a compound of formula (II) or (III)

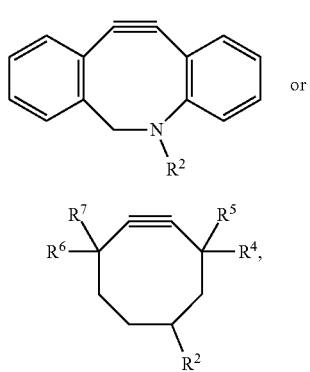

wherein
$R^1$, $R^2$, and $R^3$ are independently selected from the group consisting of substituted or unsubstituted alkyl, substituted or unsubstituted alkenyl, substituted or unsubstituted alkynyl, substituted or unsubstituted alkoxy, substituted or unsubstituted cycloalkyl, substituted or unsubstituted aryl, substituted or unsubstituted heteroaryl, substituted or unsubstituted heterocyclyl, —$(CH_2)_a$—$C(O)R^{1a}$, —$(CH_2)_a$—$C(O)OR^{1a}$, —$(CH_2)_a$—$C(O)N(R^{1a})_2$, —$(CH_2)_a$—$C(O)NHCH(R^{1a})_2$, —$(CH_2)_a$—$N(R^{1a})_2$; wherein a is integer from zero to 10; wherein each $R^{1a}$ is independently hydrogen, substituted or unsubstituted alkyl, substituted or unsubstituted alkenyl, substituted or unsubstituted alkoxy, substituted or unsubstituted cycloalkyl, substituted or unsubstituted aryl, substituted or unsubstituted heteroaryl, and substituted or unsubstituted heterocyclyl; or
$R^1$ is a first polypeptide comprising at least one non-natural amino acid residue (nnAAr) of formula (IV)

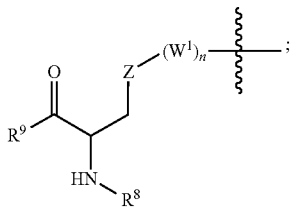

(IV)

wherein Z is absent or a 5-membered or 6-membered aryl or heteroaryl ring; $W^1$ is selected from the group consisting of $C_1$-$C_{10}$ alkylene, —NH—, —O— and —S—; n is zero or 1; $R^8$ is H or an amino acid residue of the first polypeptide, and $R^9$ is OH or an amino acid residue of the first polypeptide; and
$R^2$ and $R^3$ are independently -$L^1$-$X^1$;
wherein
$X^1$ is a polysaccharide or a second polypeptide;
$L^1$ is optional, and when present is a linker selected from the group consisting of substituted or unsubstituted alkylene, substituted or unsubstituted alkenylene, —O—, —O-(substituted or unsubstituted alkylene)-, -(substituted or unsubstituted alkylene)-O—, —O-(substituted or unsubstituted alkylene)-C(O)—$Y^1$—, —C(O)-(substituted or unsubstituted alkylene)-NH—$Y^2$—, —C(O)-(substituted or unsubstituted alkylene)-C(O)—, —C(O)-(substituted or unsubstituted alkylene)-NH—C(O)—$(CH_2$—$CH_2$—$O)_n$-(substituted or unsubstituted alkylene)-NH—, —C(O)-(substituted or unsubstituted alkylene)-NH—, —C(O)-(substituted or unsubstituted alkylene)-NH—C(O)—$(CH_2$—$CH_2$—$O)_n$-(substituted or unsubstituted alkylene)-C(O)—, —C(O)-(substituted or unsubstituted alkylene)-C(O)—NH-(substituted or unsubstituted alkylene)-, —C(O)—, —C(O)-(substituted or unsubstituted alkylene)-, -(substituted or unsubstituted alkylene)-C(O)—, —C(O)N($R^{L1}$)—, —C(O)N($R^{L1}$)-(substituted or unsubstituted alkylene)-, -(substituted or unsubstituted alkylene)-C(O)N($R^{L1}$), -(substituted or unsubstituted alkylene)-C(O)N$R^{L1}$-(substituted or unsubstituted alkylene)-, —OC(O)N($R^{L1}$)—, —OC(O)N($R^{L1}$)-(substituted or unsubstituted alkylene)-, -(substituted or unsubstituted alkylene)-OC(O)N($R^{L1}$)—, —N($R^{L1}$)C(O)—, —N$R^{L1}$C(O)-(substituted or unsubstituted alkylene)-, -(substituted or unsubstituted alkylene)-N$R^{L1}$C(O)—, —S—, —S-(substituted or unsubstituted alkylene)-, —S(O)$_k$—, —S(O)$_k$(alkylene or substituted alkylene)-, —C(S)—, —C(S)-(substituted or unsubstituted alkylene)-, —CSN($R^{L1}$)—, —CSN($R^{L1}$)-(substituted or unsubstituted alkylene)-, —N($R^{L1}$)C(O)O—, -(substituted or unsubstituted alkylene)-O—N=$CR^{L1}$—, -(substituted or unsubstituted alkylene)-S(O)$_k$-(substituted or unsubstituted alkylene)-S—, -(substituted or unsubstituted alkylene)-S—S—, —S(O)$_k$N($R^{L1}$)—, —N($R^{L1}$)C(O)N($R^{L1}$)—, —N($R^{L1}$)C(S)N($R^{L1}$)—, —N($R^{L1}$)S(O)$_k$N($R^{L1}$)—, —N($R^{L1}$)—N=, —C($R^{L1}$)=N—, —C($R^{L1}$)=N—N($R^{L1}$)—, —C($R^{L1}$)=N—N=, —C($R^{L1}$)$_2$—N=N—, and —C($R^{L1}$)$_2$—N($R^{L1}$)—N($R^{L1}$)—; wherein the bond on the left side of $L^1$, as drawn, is bound to the 8-membered ring of the compound of formula (II) or the compound of formula (III) and the bond on the right side of the $L^1$, as drawn, is bound to $X^1$;
$Y^1$ is a bond, —NH—, —O—, —S—, —NH($Y^{1a}$)—, —O($Y^{1a}$)—, or —S($Y^{1a}$)—;
$Y^2$ is a bond, —C(=O)—, —S(=O)$_2$—, —C(=O)$Y^{2a}$—, —S(=O)$_2 Y^{2a}$;
$Y^{1a}$ and $Y^{2a}$ are each independently $Y^3$ or $Y^3$NH—
$Y^3$ is substituted or unsubstituted $C_{1-10}$alkyl or —$(CH_2CH_2O)_{1-10}$—; and
n is an integer from 1 to 30;
k is 1, 2, or 3;
each $R^{L1}$ is independently hydrogen or substituted or unsubstituted alkyl; and
$R^4$, $R^5$, $R^6$, and $R^7$ are each independently hydrogen, halo, or substituted or unsubstituted alkyl.

Embodiment I-2. The method of embodiment I-1, wherein $R^1$ is a polypeptide comprising at least one non-natural amino acid residue (nnAAr).

Embodiment I-3. The method of any one of embodiments I-1 to I-2, wherein $R^1$ is a polypeptide comprising at least one non-natural amino acid residue (nnAAr) having a molecular weight of at least 15 kDa.

Embodiment I-4. The method of any one of embodiments I-2 to I-3, wherein the polypeptide comprising at least one non-natural amino acid residue (nnAAr) comprises 4-6 non-natural amino acids of formula (IV).

Embodiment I-5. The method of any one of embodiments I-2 to I-4, wherein the non-natural amino acid residue of formula (IV), replaces a lysine residue in the polypeptide comprising at least one non-natural amino acid.

Embodiment I-6. The method of any one of embodiments I-1 to I-4, wherein the polypeptide has at least 80% sequence identity, at least 85% sequence identity, at least 90% sequence identity, or at least 95% sequence identity to SEQ ID NO:1 or SEQ ID NO:2.

Embodiment I-7. The method of embodiment I-6, wherein the polypeptide comprises at least one residue sequence selected from the group consisting of residue sequences 271-290, 321-340, 331-350, 351-370, 411-430, and 431-450 of SEQ ID NO:1 that does not contain the at least 2 nnAArs.

Embodiment I-8. The method of embodiment I-6, wherein at least one nnAAr replaces an amino acid residue in SEQ ID NO:1 selected from the group consisting of K11, K25, K34, K38, K40, K83, K104, K105, K126, K158, K173, K213, K215, K217, K222, K228, K230, K237, K243, K245, K265, K300, K386, K457, K475, K499, K517, K523, K527, K535, F13, F54, F124, F128, F141, F168, F251, F390, F531, F532, D212, D296, D353, D392, D466, D468, D508, D520, N297, N360, N400, N482, N487, N503, N525, E241, E249, E250, E257, E260, E293, E363, Q253, Q288, R378, R408, R456, R461, R463, R473, R494, S199, S201, S232, S234, S240, S262, S375, S382, S398, S452, S476, S495, S496, S497, S502, S506, T254, T266, T268, T270, T294, T387, T401, T409, T470, and T518.

Embodiment I-9. The method of embodiment I-6, wherein at least one nnAAr replaces an amino acid residue in SEQ ID NO:1 selected from:
  a) a first group consisting of K25, K34, K38, K40, K213, K215, K228, K245, K265, K386, K523, and K527;
  b) a second group consisting of K25, K34, K38 and K40;
  c) a third group consisting of K213 and K215;
  d) a fourth group consisting of K11, K25, K34, K38, K40, K83, K104, K105, K126, K158, K173, K213, K215, K222, K228, K237, K243, K245, K265, K386, K475, K499, K523, K527, F13, F54, F124, F128, F141, F168, F251, F390, F531, and F532; and
  e) a fifth group consisting of K25, K215, K228, K265, K386, and K523.

Embodiment I-10. The method of embodiment I-6, wherein 2-4 nnAArs replace amino acid residues in SEQ ID NO:1 selected from the group consisting of K228, K245, K265, K386, K523, and K527.

Embodiment I-11. The method of any one of embodiments I-1 to I-3, wherein $R^1$ is SEQ ID NO:2.

Embodiment I-12. The method of any one of embodiments I-1 to I-3, wherein Z is aryl.

Embodiment I-13. The method of any one of embodiments I-1 to I-3, wherein Z is heteroaryl.

Embodiment I-14. The method of any one of embodiments I-1 to I-3, wherein $W^1$ is —CH$_2$—.

Embodiment I-15. The method of any one of embodiments I-1 to I-3, wherein n is zero.

Embodiment I-16. The method of any one of embodiments I-1 to I-3, wherein the nnAAr of formula (IV) is selected from the group consisting of

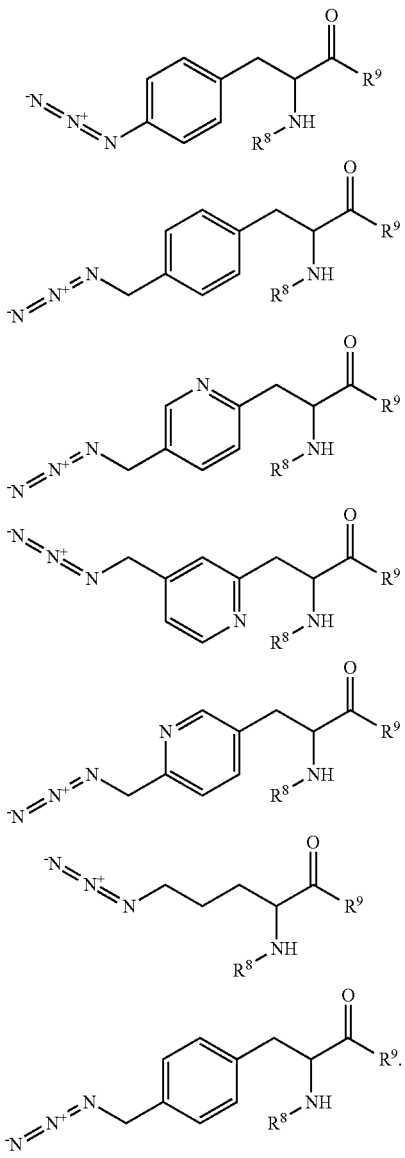

Embodiment I-17. The method of embodiment I-1, wherein $R^1$ is selected from the group consisting of substituted or unsubstituted alkyl, substituted or unsubstituted alkenyl, substituted or unsubstituted alkynyl, substituted or unsubstituted alkoxy, substituted or unsubstituted cycloalkyl, substituted or unsubstituted aryl, substituted or unsubstituted heteroaryl, substituted or unsubstituted heterocyclyl, —(CH$_2$)$_a$—C(O)R$^{1a}$, —(CH$_2$)$_a$—C(O)OR$^{1a}$, —(CH$_2$)$_a$—C(O)N(R$^{1a}$)$_2$, —(CH$_2$)$_a$—C(O)NHCH(R$^{1a}$)$_2$, —(CH$_2$)$_a$—N(R$^{1a}$)$_2$; wherein a is integer from zero to 10; wherein each R$^{1a}$ is independently hydrogen, substituted or unsubstituted alkyl, substituted or unsubstituted alkenyl, substituted or unsubstituted alkoxy, substituted or unsubstituted cycloalkyl, substituted or unsubstituted aryl, substituted or unsubstituted heteroaryl, and substituted or unsubstituted heterocyclyl.

Embodiment I-18. The method of any one of embodiments I-1 to I-2, wherein the azide compound is

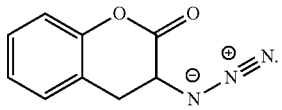 [SMILES: N#[N+][N-]C1Cc2ccccc2OC1=O]

Embodiment I-19. The method of any one of embodiments I-1 to I-18, wherein the alkyne compound is a compound of formula (V), (VI), (VII), (VIII), (IX), (X), (XI), or (XII):

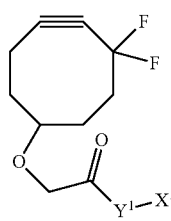
(V)

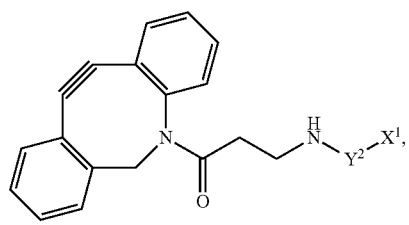
(VI)

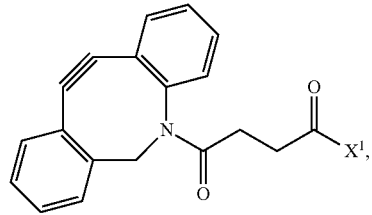
(VII)

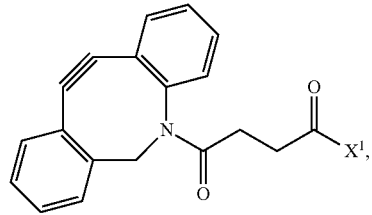
(VIII)

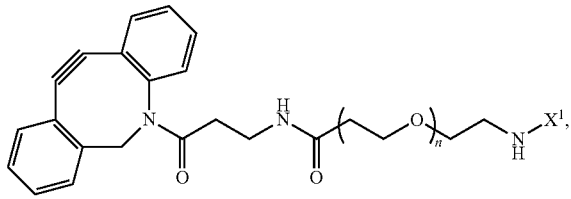
(IX)

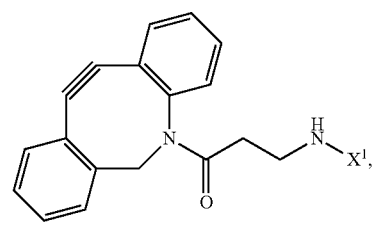

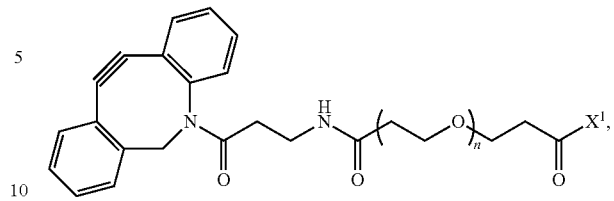
(X)

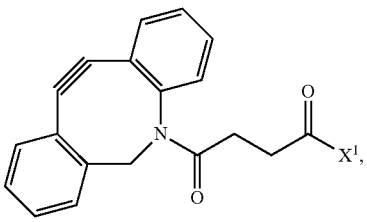
(XI)

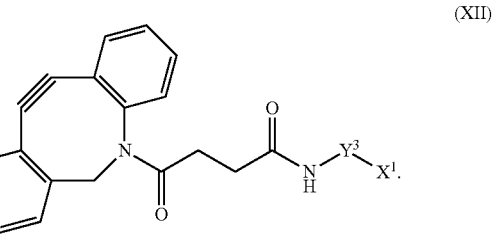
(XII)

Embodiment I-20. The method of any one of embodiments I-1 to I-19, wherein $X^1$ is a polypeptide or polysaccharide.

Embodiment I-21. The method of any one of embodiments I-1 to I-20, wherein $X^1$ is a capsular polysaccharide from a bacterium selected from the group consisting of *Streptococcus pneumoniae, Neisseria meningitidis, Haemophilus influenzae, Streptococcus pyogenes, Streptococcus agalactiae*, and *Porphyromonas gingivalis*.

Embodiment I-22. The method of any one of embodiments I-1 to I-21, wherein $X^1$ is a capsular polysaccharide of a *S. pneumoniae* serotype selected from the group consisting of 1, 3, 4, 5, 6A, 6B, 7F, 9V, 14, 18C, 19A, 19F, 23F, 2, 6C, 8, 9N, 10A, 12F, 15A, 15B, 15C, 16F, 17F, 20, 20A, 20B, 22F, 23A, 23B, 24F, 24B, 31, 33F, 34, 35B, 35F and 38.

Embodiment I-23. The method of embodiment I-1, wherein the alkyne compound is a compound of formula (II):

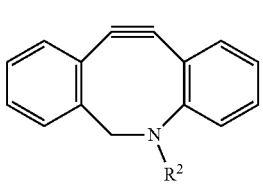
(II)

wherein $R^2$ is selected from the group consisting of substituted or unsubstituted alkyl, substituted or unsubstituted alkenyl, substituted or unsubstituted alkynyl, substituted or unsubstituted alkoxy, substituted or unsubstituted cycloalkyl, substituted or unsubstituted aryl, substituted or unsubstituted heteroaryl, substituted or unsubstituted heterocyclyl, —$(CH_2)_a$—$C(O)R^{1a}$, —$(CH_2)_a$—$C(O)OR^{1a}$, —$(CH_2)_a$—$C(O)N(R^{1a})_2$, —$(CH_2)_a$—$C(O)NHCH(R^{1a})_2$, —$(CH_2)_a$—$N(R^{1a})_2$;

wherein a is integer from zero to 10; wherein each $R^{1a}$ is independently hydrogen, substituted or unsubstituted alkyl, substituted or unsubstituted alkenyl, substituted or unsubstituted alkoxy, substituted or unsubstituted cycloalkyl, substituted or unsubstituted aryl, substituted or unsubstituted heteroaryl, and substituted or unsubstituted heterocyclyl.

Embodiment I-24. The method of embodiment I-1, wherein the alkyne compound is a compound of formula (III)

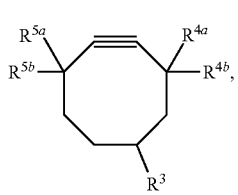

wherein $R^3$ is selected from the group consisting of substituted or unsubstituted alkyl, substituted or unsubstituted alkenyl, substituted or unsubstituted alkynyl, substituted or unsubstituted alkoxy, substituted or unsubstituted cycloalkyl, substituted or unsubstituted aryl, substituted or unsubstituted heteroaryl, substituted or unsubstituted heterocyclyl, —(CH$_2$)$_a$—C(O)R$^{1a}$, —(CH$_2$)$_a$—C(O)OR$^{1a}$, —(CH$_2$)$_a$—C(O)N(R$^{1a}$)$_2$, —(CH$_2$)$_a$—C(O)NHCH(R$^{1a}$)$_2$, —(CH$_2$)$_a$—N(R$^{1a}$)$_2$; wherein a is integer from zero to 10; wherein each $R^{1a}$ is independently hydrogen, substituted or unsubstituted alkyl, substituted or unsubstituted alkenyl, substituted or unsubstituted alkoxy, substituted or unsubstituted cycloalkyl, substituted or unsubstituted aryl, substituted or unsubstituted heteroaryl, and substituted or unsubstituted heterocyclyl.

Embodiment I-25. The method of any one of embodiments I-1 to I-24, wherein the LDAO is at a concentration of 0.05% v/v to 2% v/v.

Embodiment I-26. The method of any one of embodiments I-1 to I-25, wherein method is performed in 10 to 20% v/v DMSO.

Embodiment I-27. The method of any one of embodiments I-1 to I-26, wherein the alkyne compound is at a concentration of 0.5 mg/ml to 2 mg/ml.

Embodiment I-28. The method of any one of embodiments I-1 to I-16 and 1-19 to I-27, wherein the first polypeptide comprising at least one non-natural amino acid is at a concentration of 0.5 mg/ml to 2 mg/ml.

Embodiment I-29. The method of any one of embodiments I-1 to I-28, wherein the method is performed at room temperature.

Embodiment I-30. The method of any one of embodiments I-1 to I-29, wherein the method is performed for about 2 to 8 hours.

Embodiment I-31. A heteroaryl-containing compound prepared by the method of any one of embodiments I-1 to I-16 and 1-19 to I-28, wherein $R^1$ is a first polypeptide comprising at least one non-natural amino acid residue of formula IV.

Embodiment I-32. A heteroaryl-containing bioconjugate comprising a polypeptide and antigen of any one of Formulae XIII, XIV, XV, or XVI:

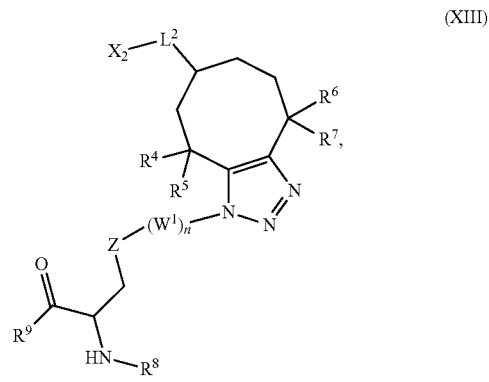

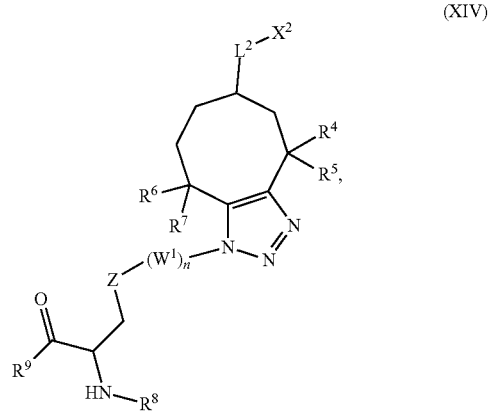

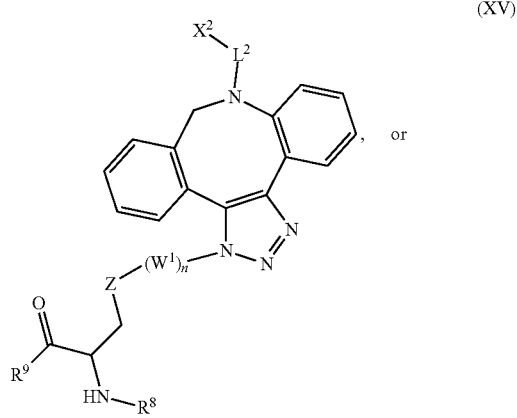

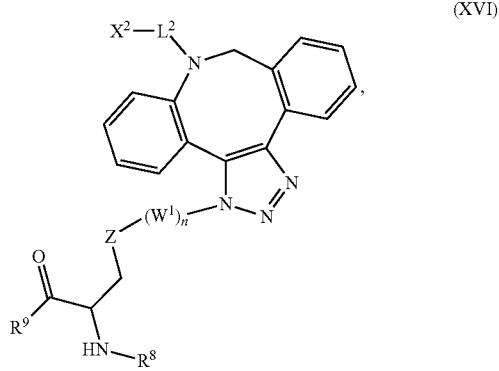

wherein the first polypeptide comprises at least one nnAAr comprising an azido moiety, of Formula (I'):

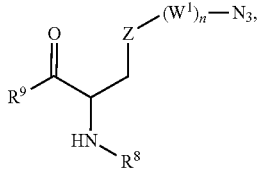

(I')

wherein Z is absent or a 5-membered or 6-membered aryl or heteroaryl ring; $W^1$ is selected from the group consisting of $C_1$-$C_{10}$ alkylene, —NH—, —O— and —S—; n is zero or 1; $R^8$ is H or an amino acid residue of the first polypeptide, and $R^9$ is OH or an amino acid residue of the first polypeptide, wherein at least one of $R^8$ and $R^9$ is an amino acid residue of the first polypeptide;

wherein the azido moiety of the nnAAr is conjugated to an alkyne by contacting the nnAAr and the alkyne in the presence of LDAO, the alkyne is formula II'-A, III'-A, or III'-B:

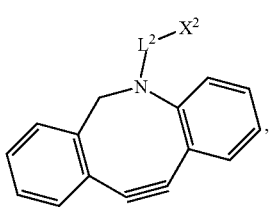

(II'-A)

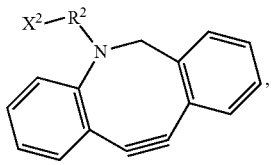

(II'-B)

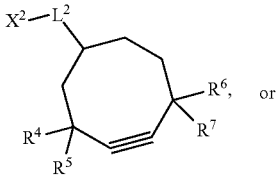

(III'-A)

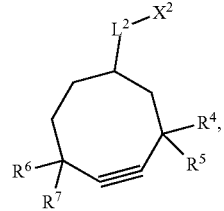

(III'-B)

wherein $X^2$ is an antigen comprising a polysaccharide or second polypeptide, $L^2$ is optional, and when present is a linker selected from the group consisting of substituted or unsubstituted alkylene, substituted or unsubstituted alkenylene, —O—, —O-(substituted or unsubstituted alkylene)-, -(substituted or unsubstituted alkylene)-O—, —O-(substituted or unsubstituted alkylene)-C(O)—$Y^1$—, —C(O)-(substituted or unsubstituted alkylene)-NH—$Y^2$—, —C(O)-(substituted or unsubstituted alkylene)-C(O)—, —C(O)-(substituted or unsubstituted alkylene)-NH—C(O)—(CH$_2$—CH$_2$—O)$_n$-(substituted or unsubstituted alkylene)-NH—, —C(O)-(substituted or unsubstituted alkylene)-NH—, —C(O)-(substituted or unsubstituted alkylene)-NH—C(O)—(CH$_2$—CH$_2$-0)$_n$-(substituted or unsubstituted alkylene)-C(O)—, —C(O)-(substituted or unsubstituted alkylene)-C(O)—NH-(substituted or unsubstituted alkylene)-, —C(O)—, —C(O)-(substituted or unsubstituted alkylene)-, -(substituted or unsubstituted alkylene)-C(O)—, —C(O)N($R^{L1}$)—, —C(O)N($R^{L1}$)-(substituted or unsubstituted alkylene)-, -(substituted or unsubstituted alkylene)-C(O)N($R^{L1}$), -(substituted or unsubstituted alkylene)-C(O)N$R^{L1}$-(substituted or unsubstituted alkylene)-, —OC(O)N($R^{L1}$)—, —OC(O)N($R^{L1}$)-(substituted or unsubstituted alkylene)-, -(substituted or unsubstituted alkylene)-OC(O)N($R^{L1}$)—, —N($R^{L1}$)C(O)—, —N$R^{L1}$C(O)-(substituted or unsubstituted alkylene)-, -(substituted or unsubstituted alkylene)-N$R^{L1}$C(O)—, —S—, —S-(substituted or unsubstituted alkylene)-, —S(O)$_k$—, —S(O)$_k$(alkylene or substituted alkylene)-, —C(S)—, —C(S)-(substituted or unsubstituted alkylene)-, —CSN($R^{L1}$)—, —CSN($R^{L1}$)-(substituted or unsubstituted alkylene)-, —N($R^{L1}$)C(O)O—, -(substituted or unsubstituted alkylene)-O—N=C$R^{L1}$—, -(substituted or unsubstituted alkylene)-S(O)$_k$-(substituted or unsubstituted alkylene)-S—, -(substituted or unsubstituted alkylene)-S—S—, —S(O)$_k$N($R^{L1}$)—, —N($R^{L1}$)C(O)N($R^{L1}$)—, —N($R^{L1}$)C(S)N($R^{L1}$)—, —N($R^{L1}$)S(O)$_k$N($R^{L1}$)—, C($R^{L1}$)=N—, —C($R^{L1}$)=N—N($R^{L1}$)—, —C($R^{L1}$)=N—N=, —C($R^{L1}$)$_2$—N=N—, and —C($R^{L1}$)$_2$—N($R^1$)—N($R^1$)—; wherein the bond on the left side of $L^1$, as drawn, is bound to the 8-membered ring of the compound of formula (II) or the compound of formula (III) and the bond on the right side of the $L^1$, as drawn, is bound to $X^1$;

$Y^1$ is a bond, —NH—, —O—, —S—, —NH($Y^{1a}$)—, —O($Y^{1a}$)—, or —S($Y^{1a}$)—;

$Y^2$ is a bond, —C(=O)—, —S(=O)$_2$—, —C(=O)$Y^{2a}$—, —S(=O)$_2Y^{2a}$;

$Y^{1a}$ and $Y^{2a}$ are each independently $Y^3$ or $Y^3$NH—

$Y^3$ is substituted or unsubstituted $C_{1-10}$alkyl or —(CH$_2$CH$_2$O)$_{1-10}$—; and n is an integer from 1 to 30;

k is 1, 2, or 3;

each $R^{L1}$ is independently hydrogen or substituted or unsubstituted alkyl; and $R^4$, $R^5$, $R^6$, and $R^7$ are each independently hydrogen, halo, or substituted or unsubstituted alkyl; wherein the conjugate has a molecular weight of at least 1.3 times greater than the conjugate molecular weight when LDAO is not used.

Embodiment I-33. The heteroaryl-containing bioconjugate of embodiment I-32, wherein the conjugate has a molecular weight of at least 1.4 times greater than the conjugate molecular weight when LDA is not used.

Embodiment I-34. The heteroaryl-containing bioconjugate of embodiment I-32 or 1-33, wherein the conjugate has a molecular weight of at least 1.5 times greater than the conjugate molecular weight when LDA is not used.

Embodiment I-35. The heteroaryl-containing bioconjugate of any one of embodiments I-32 to I-34, wherein the conjugate has a molecular weight of at least 1.6 times greater than the conjugate molecular weight when LDA is not used.

Embodiment I-36. The heteroaryl-containing bioconjugate of any one of embodiments I-32 to I-35, wherein the conjugate has a molecular weight of at least 1.7 times greater than the conjugate molecular weight when LDA is not used.

Embodiment I-37. A heteroaryl-containing bioconjugate comprising a first polypeptide and antigen of any one of Formulae XIII, XIV, XV, or XVI:

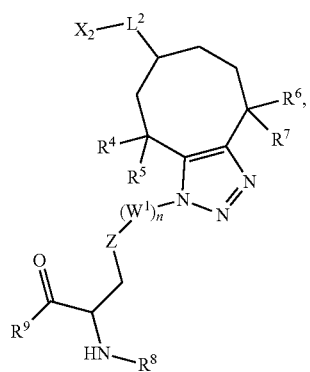

(XIII)

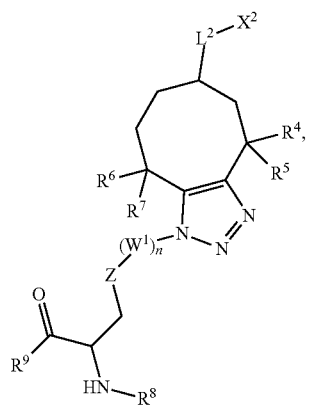

(XIV)

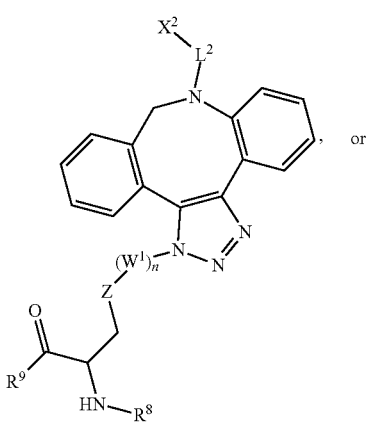

(XV)

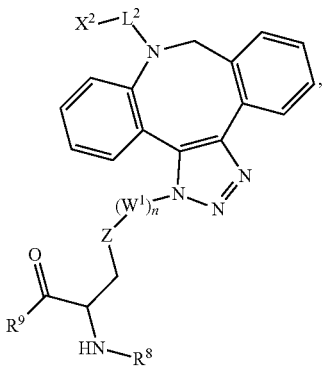

(XVI)

wherein
the first polypeptide comprises at least one nnAAr comprising an azido moiety, of Formula (I'):

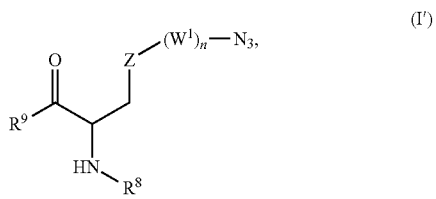

(I')

wherein Z is absent or a 5-membered or 6-membered aryl or heteroaryl ring; $W^1$ is selected from the group consisting of $C_1$-$C_{10}$ alkylene, —NH—, —O— and —S—; n is zero or 1; $R^8$ is H or an amino acid residue of the first polypeptide, and $R^9$ is OH or an amino acid residue of the first polypeptide;

wherein the azido moiety of the nnAAr is conjugated to an alkyne by contacting the nnAAr and the alkyne in the presence of LDAO, wherein the alkyne is of formula II'-A, III'-A, or III'-B:

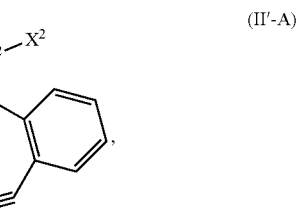

(II'-A)

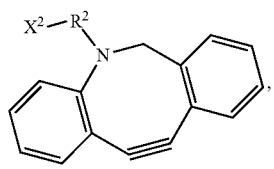

(II'-B)

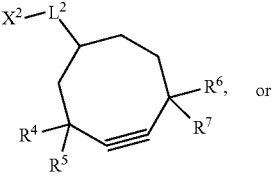

(III'-A)

(III'-B)

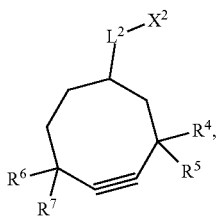

wherein

X² is an antigen comprising a polysaccharide or second polypeptide, L² is optional, and when present is a linker selected from the group consisting of substituted or unsubstituted alkylene, substituted or unsubstituted alkenylene, —O—, —O-(substituted or unsubstituted alkylene)-, -(substituted or unsubstituted alkylene)-O—, —O-(substituted or unsubstituted alkylene)-C(O)—Y¹—, —C(O)-(substituted or unsubstituted alkylene)-NH—Y²—, —C(O)-(substituted or unsubstituted alkylene)-C(O)—, —C(O)-(substituted or unsubstituted alkylene)-NH—C(O)—(CH$_2$—CH$_2$—O)$_n$-(substituted or unsubstituted alkylene)-NH—, —C(O)-(substituted or unsubstituted alkylene)-NH—, —C(O)-(substituted or unsubstituted alkylene)-NH—C(O)—(CH$_2$—CH$_2$—O)$_n$-(substituted or unsubstituted alkylene)-C(O)—, —C(O)-(substituted or unsubstituted alkylene)-C(O)—NH-(substituted or unsubstituted alkylene)-, —C(O)—, —C(O)-(substituted or unsubstituted alkylene)-, -(substituted or unsubstituted alkylene)-C(O)—, —C(O)N(R$^{L1}$)—, —C(O)N(R$^{L1}$)-(substituted or unsubstituted alkylene)-, -(substituted or unsubstituted alkylene)-C(O)N(R$^{L1}$), -(substituted or unsubstituted alkylene)-C(O)NR$^{L1}$-(substituted or unsubstituted alkylene)-, —OC(O)N(R$^{L1}$)—, —OC(O)N(R$^{L1}$)-(substituted or unsubstituted alkylene)-, -(substituted or unsubstituted alkylene)-OC(O)N(R$^{L1}$)—, —N(R$^{L1}$)C(O)—, —NR$^{L1}$C(O)-(substituted or unsubstituted alkylene)-, -(substituted or unsubstituted alkylene)-NR$^{L1}$C(O)—, —S—, —S-(substituted or unsubstituted alkylene)-, —S(O)$_k$—, —S(O)$_k$(alkylene or substituted alkylene)-, —C(S)—, —C(S)-(substituted or unsubstituted alkylene)-, —CSN(R$^{L1}$)-(substituted or unsubstituted alkylene)-, —N(R$^{L1}$)C(O)O—, -(substituted or unsubstituted alkylene)-O—N=CR$^{L1}$—, -(substituted or unsubstituted alkylene)-S(O)$_k$-(substituted or unsubstituted alkylene)-S—, -(substituted or unsubstituted alkylene)-S—S—, —S(O)$_k$N(R$^{L1}$)—, —N(R$^{L1}$)C(O)N(R$^{L1}$)—, —N(R$^{L1}$)C(S)N(R$^{L1}$)—, —S(O)$_k$N(R$^{L1}$)—, —C(R$^{L1}$)=N—N(R$^{L1}$)—, —C(R$^{L1}$)=N—N=, —C(R$^{L1}$)$_2$—N=N—, and —C(R$^{L1}$)$_2$—N(R$^{L1}$)—N(R$^{L1}$)—; wherein the bond on the left side of L¹, as drawn, is bound to the 8-membered ring of the compound of formula (II) or the compound of formula (III) and the bond on the right side of the L¹, as drawn, is bound to X¹;

Y¹ is a bond, —NH—, —O—, —S—, —NH(Y$^{1a}$)—, —O(Y$^{1a}$)—, or —S(Y$^{1a}$)—;

Y² is a bond, —C(=O)—, —S(=O)$_2$—, —C(=O)Y$^{2a}$—, —S(=O)$_2$Y$^{2a}$;

Y$^{1a}$ and Y$^{2a}$ are each independently Y³ or Y³NH—

Y³ is substituted or unsubstituted C$_{1-10}$alkyl or —(CH$_2$CH$_2$O)$_{1-10}$—; and n is an integer from 1 to 30;

k is 1, 2, or 3;

each R$^{L1}$ is independently hydrogen or substituted or unsubstituted alkyl; and R⁴, R⁵, R⁶, and R⁷ are each independently hydrogen, halo, or substituted or unsubstituted alkyl; and wherein wherein the antibody titer upon challenge is greater for the conjugate compared to antibody titer upon challenge of a conjugate of the same formula where conjugation of the first polypeptide and the antigen is performed in the absence of LDAO, when tested under equivalent challenge conditions.

Embodiment II-16. The method of any one of embodiments I-1 to I-3, wherein the nnAAr of formula (IV) is:

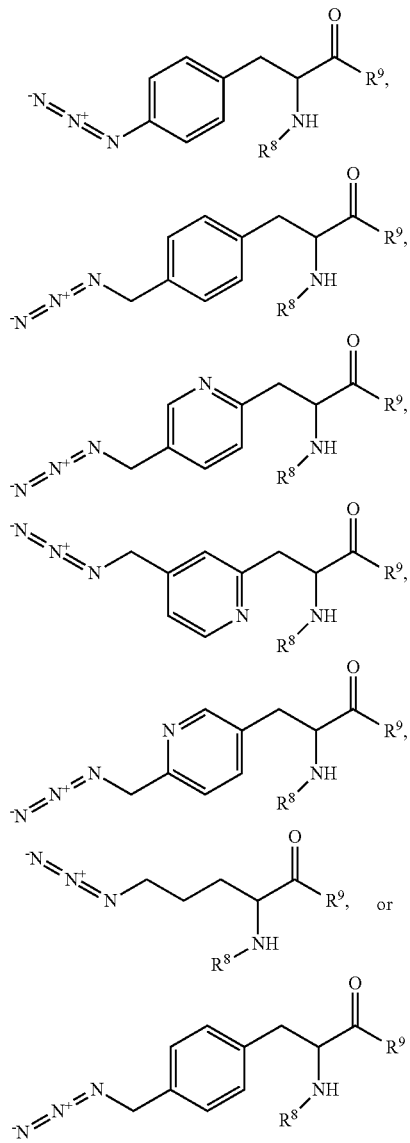

EXAMPLES

The disclosure is further illustrated by the following examples, which are not to be construed as limiting this disclosure in scope or spirit to the specific procedures herein described. It is to be understood that the examples are provided to illustrate certain embodiments and that no limitation to the scope of the disclosure is intended thereby. It is to be further understood that resort may be had to various other embodiments, modifications, and equivalents thereof which may suggest themselves to those skilled in the art without departing from the spirit of the present disclosure and/or scope of the appended claims.

Example 1: Azide-Alkyne Cycloaddition Accelerated in the Presence of Different Detergents In order to probe the kinetics of the azide-alkyne cycloaddition upon treatment with LDAO, 3-azido-7-hydroxycoumarin (azidocoumarin) was reacted with a dibenzylcyclooctyne (DBCO) derivative. Specifically, DBCO-PEG4-NH$_2$ was reacted overnight with 100 µM azidocoumarin in the presence of 0.1% LDAO and other solvents and detergents, and the fluorescent intensity was measured to determine the rate of reaction. Fluorescent intensity was measured with 404 nm excitation and 464 nm emission with 435 nm cutoff.

FIG. 1A shows a readout of reaction kinetics as a function of time. The reaction containing 0.1% LDAO proceeded to completion at approximately 1 hour, whereas the reactions containing 10% DMSO, 0.1% PS80, and 0.1% SDOC proceed much more slowly, or did not reach completion at 16 hours.

A conjugation reaction between CRM-pAMF6-mutant (SEQ ID NO:2) with *Streptococcus pneumoniae* serotype 9N was performed in buffer, 0.01% LDAO, 0.01% LDAO+0.4M NaCl, and 0.1% LDAO. Specifically 1 mg/mL eCRM was reacted with serotype 9N activated polysaccharide at a starting level of 75 µM DBCO in a Spectramax Gemini plate reader, reading absorbance at 309 nm. FIG. 1B shows the kinetics for each conjugation reaction (all pseudo-first-order), with the conjugation run in 0.1% LDAO proceeding most rapidly.

Figure 1B:
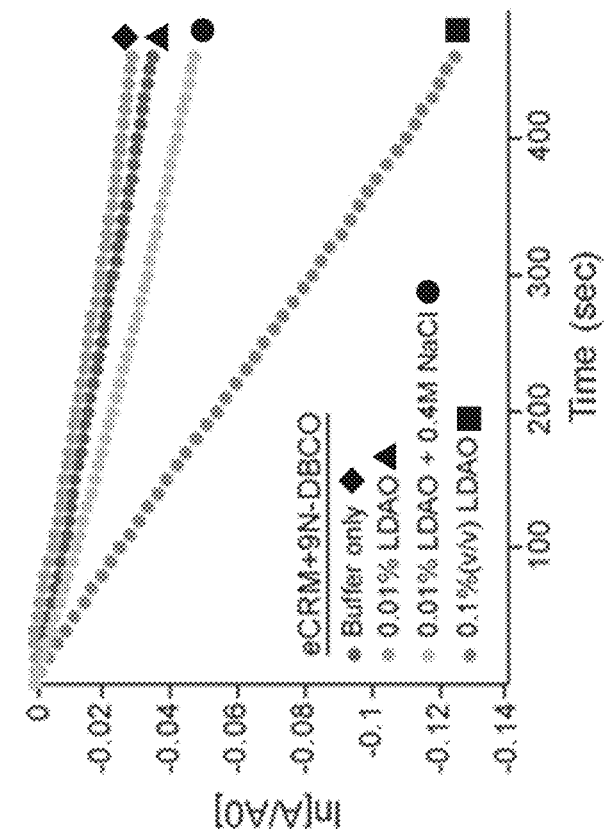
FIG. 1B shows reaction kinetics for a series of conjugation reactions between CRM-pAMF6-mutant and polysaccharide serotype 9N in various solutions.
Figure 1D:
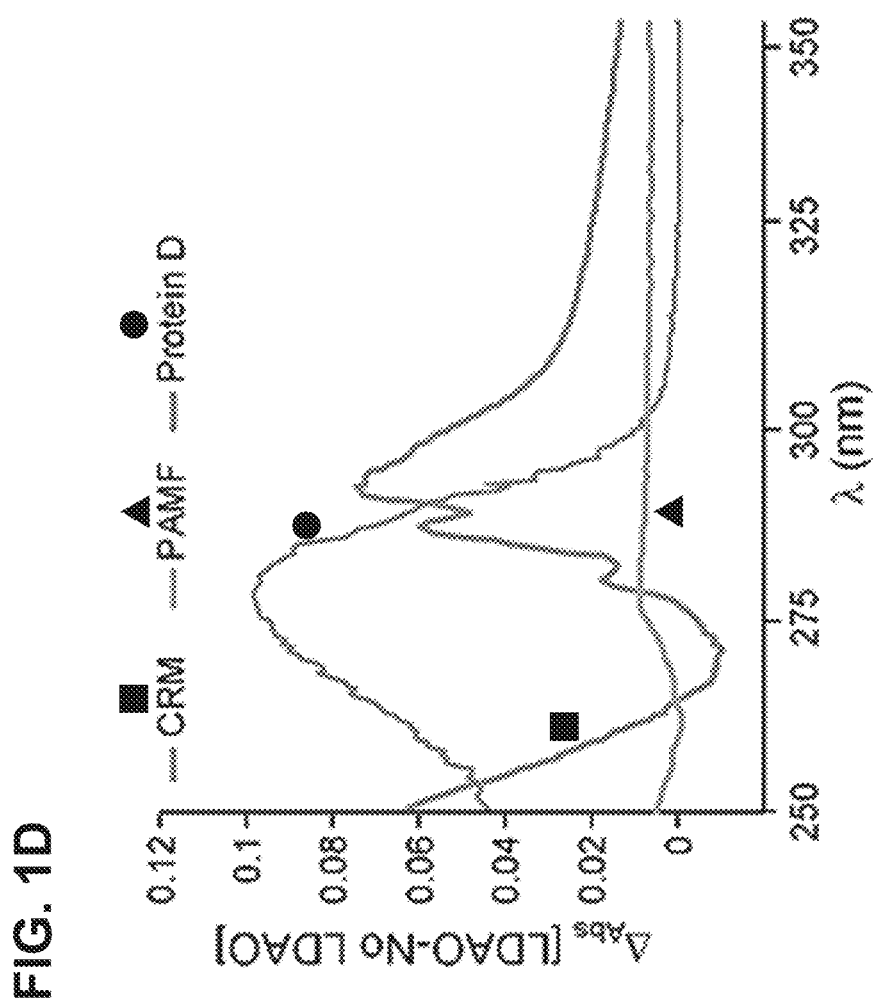
FIG. 1D shows the change in absorbance of reaction components when LDAO is used versus when it is not.

FIG. 1C shows the absorbance of azidocoumarin in both 20% DMSO and 0.1% LDAO. FIG. 1D shows the change in absorbance of reaction components when LDAO is used versus when it is not. The observed redshift correlates with the ability of LDAO to catalyze the cycloaddition reaction. Unlike Protein D, CRM-pAMF6 showed a significant redshift of the spectrum with LDAO present.

Example 2: Generation of Conjugates Using LDAO

Conjugates of CRM-pAMF6 mutant (SEQ ID NO:2) with *Streptococcus pneumoniae* serotypes 3, 5, 18C, and 19A were made using methods of this disclosure.

Linkage of DBCO-PEG4-NH$_2$ to sized polysaccharides using CDAP: Serotypes 3, 18C, and 19A were activated using CDAP (1-cyano-4-dimethylaminopyridinium tetrafluoroborate). Frozen sized-polysaccharide (SPS) (final concentration: 2 mM for serotypes 18C and 19A; 4 mM for serotype 3) was thawed, homogenized, and diluted with water for injection (WFI). To the diluted SPS was then added an appropriate amount of 1M borate buffer, pH 8.5, such that the final reaction concentration of borate is 100 mM. The temperature was adjusted to 21° C. and kept at this temperature for the remainder of the process. The buffered solution of SPS was then stirred at a high rate to ensure that the CDAP is distributed throughout the solution rapidly upon addition The CDAP solution (25-100 mg/mL in acetonitrile) was then added via PressurePlus bottle over a short period of time (e.g., 1 min). Five minutes after complete addition of the CDAP solution, the DBCO-PEG4-amine solution was added via PressurePlus bottle over a short period of time (e.g., 2 min). Once the solution was homogenous, the rate of stirring was reduced. The reaction was allowed to proceed for 60 min, and 2M glycine (pH 8.4) was then added to a final concentration of 200 mM and was allowed to react for 2 h to quench the reaction. Following the completion of the glycine quench, the APS (activated polysaccharide) was purified via tangential flow filtration (TFF). The basic TFF parameters are as follows:
 a. Membrane: Sartorius HydroSart, E-screen, 30 kDa MWCO
 b. Membrane loading: Approximately 6-12 g APS per m$^2$ of membrane
 c. TMP: 1.1 bar
 d. Feedflow: 240 LMH
 e. APS diafiltration concentration: same as reaction
 f. Diafiltration strategy: 12 diavolumes of 150 mM NaCl, followed by 8 diavolumes of WFI.
 g. Ultrafiltration strategy: Following diafiltration, the activated polysaccharide was concentration to 7.0 or 3.5 mg/mL.
 h. Collection/flush: Following the completion of the UF, the APS was collected from the reactor. Approximately 100 mL of WFI was then added to the reactor and passed through the system (including through membranes) a single time and collected separately from the bulk solution. The rinse solution is not recirculated.

The purified APS was then filtered through a 0.2 micron-rated filter into a polycarbonate bottle. The filter was rinsed with the TFF rinse solution and combined with the rest of the APS. A sample is taken and the concentration of the APS is determined with an Anthrone assay. The APS was diluted to a target concentration of 2.0 or 4.0 mg/mL with WFI. After addition of WFI, the solution was homogenized by stirring with a magnetic stir bar. The material was stored at <-65° C.

Linkage of DBCO-PEG4-NH$_2$ to sized polysaccharides using sodium periodate and reductive amination: Serotype 5 was activated using sodium periodate. Frozen SPS (reaction concentration: 2 mg/mL) was thawed, homogenized, and diluted with WFI. To the diluted SPS was then added an appropriate amount of 1M acetate buffer, pH 5.5, such that the final reaction concentration of acetate is 50 mM. The temperature was adjusted to 21° C. and kept at this temperature for the remainder of the process. To the stirred buffered SPS solution was added sodium periodate solution (5 mg/mL in WFI) over a defined addition time (e.g., 5 min). The oxidation was allowed to proceed for 180 min, and the oxidized polysaccharide (OPS) was purified via TFF. The basic TFF parameters are as follows:
 a. Membrane: Sartorius HydroSart, E-screen, 30 kDa MWCO
 b. Membrane loading: 10-16 g OPS per m$^2$ of membrane
 c. TMP: 1.1 bar
 d. Feedflow: 300 LMH
 e. OPS diafiltration concentration: same as reaction concentration (2 mg/mL)
 f. Diafiltration strategy: 10 diavolumes of WFI
 g. Ultrafiltration strategy: Following diafiltration, the OPS is concentrated to a target concentration of 6.0 mg/mL.
 h. Collection/flush: Following the completion of the UF, the OPS was collected from the reactor. Approximately 100 mL of WFI was then added to the reactor and passed through the system (including through membranes) a single time and collected separately from the bulk solution. The rinse solution was not recirculated.

The purified OPS was then filtered through a 0.2 micron-rated filter into a glass bottle. The filter was rinsed with the TFF rinse solution and combined with the rest of the OPS. A sample was taken and the concentration of the OPS was determined with the Anthrone assay. The OPS was diluted to a target concentration of 4.0 mg/mL with WFI. The solution was then homogenized by stirring with a magnetic stir bar.

To the active polysaccharide was added an appropriate amount of 1M sodium phosphate, pH 5.3 such that the final concentration of phosphate is 100 mM. DBCO-PEG4-amine in DMSO (100 mg/mL, for a final concentration of 10% DMSO in reaction) was added via PressurePlus bottle. Due to the exothermic nature of DMSO/water mixing, the temperature of the solution may briefly increase before returning to the setpoint. Sodium cyanoborohydride (approximately 22-44 mg/mL in WFI) was then added. The reaction was stirred and allowed to proceed for 18-24 hours before being purified by TFF. Sample TFF parameters are as follows:
   a. Membrane: Sartorius HydroSart, E-screen, 30 kDa MWCO
   b. Membrane loading: Approximately 6-12 g APS per $m^2$ of membrane
   c. TMP: 1.1 bar
   d. Feedflow: 240 LMH
   e. APS diafiltration concentration: same as reaction concentration (3 mg/mL)
   f. Diafiltration strategy: 12 diavolumes of 150 mM NaCl, followed by 8 diavolumes of WFI.
   g. Ultrafiltration strategy: Following diafiltration, concentrate the APS to a target concentration (based on batch scale) of 7.0 or 3.5 mg/mL.
   h. Collection/flush: Following the completion of the UF, the APS is collected from the reactor. Approximately 100 mL of WFI is then added to the reactor and passed through the system (including through membranes) a single time and collected separately from the bulk solution. The rinse solution is not recirculated.

The purified APS was then filtered through a 0.2 micron-rated filter into a polycarbonate bottle. The filter was rinsed with the TFF rinse solution and combined with the rest of the APS. A sample is taken and the concentration of the APS is determined with an Anthrone assay. The APS was diluted to a target concentration of 2.0 or 4.0 mg/mL with WFI. After addition of WFI, the solution was homogenized by stirring with a magnetic stir bar. The material was stored at <−65° C.

Conjugation of activated polysaccharide to polypeptides: CRM-pAMF6 mutant-polysaccharide conjugates were prepared using the conditions in Table 2.

In a glass vial, was added in order (with stirring) water, potassium phosphate (500 mM) for a final concentration of 10 mM, sodium chloride (5000 mM) for a final concentration of 150 mM for serotype 3 and 300 mM for the other serotypes, DMSO for a final concentration of 15%, LDAO (30%) for a final concentration of 1.0%, the thawed activated polysaccharide, and thawed CRM-pAMF6 mutant. The reaction mixture was stirred for 4 hours at room temperature. The mixture was then quenched for two hours with 4 eq. of sodium azide. After quenching, the reaction mixture was transferred to 100 kDa dialysis tube and dialyzed against 5 mM sodium succinate pH 5.8, 150 mM NaCl buffer with at least two changes. After dialysis, the mixture was filtered through a 0.6/0.2 um dual-layer filter from Pall. Samples were collected and run in an anthrone assay to determine the concentration of the conjugate. 10 µL of each sample was collected and run an SDS-PAGE of all conjugates.

Example 3: Difference in Conjugate Molecular Weight Observed Under LDAO Treatment Molecular weight of each conjugate was determined using SEC-Multi-Angle Light Scattering (MALS) Analysis. The SEC MALS-UV-RI setup consists of an Agilent HPLC 1100 degasser, temperature-controlled auto-sampler (4° C.), column compartment (25° C.) and UV-VIS diode array detector (Agilent, Santa Clara, CA) in line with a DAWN-HELEOS multi-angle laser light scattering detector and Optilab T-rEX differential refractive interferometer (Wyatt Technology, Santa Barbara, CA) coupled to three TOSOH columns in series: TSKgel Guard PWXL 6.0 mm ID×4.0 cm long, 12 µm particle; TOSOH TSKgel 6000 PWXL 7.8 mm ID×30 cm long, 13 µm particle; and a TSKgel 3000 PWXL 7.8 mm ID×30 cm long, 7 µm particle. A mobile phase consisting of 0.2 µm filtered 1×PBS+5% acetonitrile was used at a 0.5 mL/min flow rate and 30-40 µg sample was injected for analysis. Agilent Open Lab software was used to control the HPLC, and Wyatt Astra 7 software was used for data collection and molecular weight analysis.

100 µL of each conjugate was collected to run in the SEC-MALS. The amount of PS in 100 µL of conjugate was determined, and the same amount was injected in the SEC-MALS. This is to compare the elusion profile of the free PS to that of the conjugate. The amount of CRM-pAMF6 mutant in 100 µL of conjugate was determined and the same amount of CRM-pAMF6 mutant was injected in the SEC-MALS. Finally, the SEC-MALS data was analyzed and the MW of samples was determined. Table 3 shows a comparison of conjugate molecular weights when LDAO is used versus when it is not, and the SEC-MALS plots and accompanying gels are shown in FIGS. 3A-3D.

TABLE 2

Conditions for Conjugation of Activated Polysaccharide to Polypeptides

| PS Reagent as prepared above | PS Conc in Final Rxn (mg/mL) | CRM-pAMF6 mutant Conc in Final Rxn (mg/mL) | Input Ratio (PS:CRM) | Potasium Phosp. Conc. (mM) | NaCl Conc. (mM) | DMSO Conc. (V/V %) | LDAO Conc. (V/V %) | Quench NaN3 (eq) | Quench Time (h) |
|---|---|---|---|---|---|---|---|---|---|
| PS3-DB | 0.5 | 0.825 | 0.63 | 10 | 150 | 15 | 0.1 | 4 | 2 |
| PS5-DB | 0.5 | 0.278 | 1.8 | 10 | 300 | 15 | 0.1 | 4 | 2 |
| PS18C-DB | 1.5 | 1.5 | 1 | 10 | 300 | 15 | 0.1 | 4 | 2 |
| PS19A-DB | 0.6 | 0.5 | 1.2 | 10 | 300 | 15 | 0.1 | 4 | 2 |

FIGS. 4A-4D show the saccharide monomer and molecular weight of the conjugate over the course of the conjugation reaction for PS 3, 5, 18C, and 19A, respectively.

In all cases, for conjugates of polysaccharide serotypes 3, 5, 18C, and 19A, the use of LDAO results in conjugates of higher molecular weight.

TABLE 3

Comparison of conjugate molecular weights - LDAO vs no LDAO

| Sample ID | Mw (kDa) | |
|---|---|---|
| | no LDAO | LDAO |
| PS3-CRM-pAMF6 mutant | 3375.5 | 5785.0 |
| PS5-CRM-pAMF6 mutant | 1268.4 | 2846.2 |
| PS18C-CRM-pAMF6 mutant | 2547.6 | 5830.9 |
| PS19A-CRM-pAMF6 mutant | 1030.2 | 1556.8 |

Figure 5:
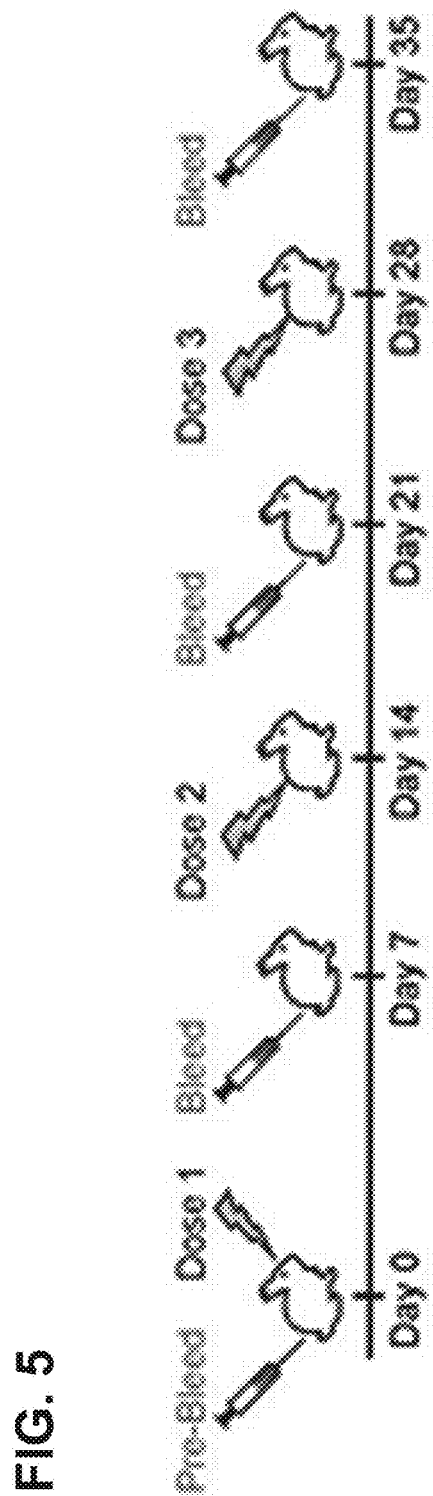
FIG. 5 shows a graphical representation of an immunization and bleeding regimen for conjugates produced using LDAO.

Example 4: Synthesis Using LDAO Results in Conjugates that Promote Higher Antibody Titer Immunization of rabbits with PS3-CRM-pAMF6 mutant, PS5-CRM-pAMF6 mutant, PS18C-CRM-pAMF6 mutant, and PS19A-CRM-pAMF6 mutant. Experiments were performed to assess the antibody responses produced by purified conjugates. Briefly, rabbits were immunized intramuscularly with 50 μg of each indicated conjugate or vehicle control on days 0, 14, and 28. Animals were bled prior to immunization (pre-bleed), and on Days 7, 21, and 35 (terminal bleed) after immunizations. This is represented graphically in FIG. 5. Serum was harvested from each blood sample and antibody titers against the immunizing antigens were assessed by ELISA.

ELISA assays were run to measure antibody titer post-treatment. ELISA assays were conducted on NUNC ELISA plates. Screening antigen solutions were prepared as follows: Serotype 3 conjugates, diluted to 1 μg/mL in PBS; Serotype 5 conjugates, diluted to 2.5 μg/mL in PBS; Serotype 18C conjugates, diluted to 2.5 μg/mL in PBS; Serotype 19A conjugates, diluted to 1 μg/mL in PBS. Assay diluent was 1×PBS+3% BSA and sample diluent was 1×PBS+3% BA. The positive control was 24V rabbit antisera diluted 1:10, then serially diluted by 5 in sample diluent. All pre-immune samples were diluted in assay diluent starting at 1:10, then serially diluted by 5. All post-immune samples were diluted 1:10 in sample diluent, then serially diluted by 5. Control serum was produced by pooling pre-immune serum from all groups, diluting 1:10, and serially diluting by 5 in assay diluent. The secondary antibody was donkey anti-Rabbit IgG (H+L) peroxidase conjugated (Jackson ImmunoResearch cat #711-035-152) diluted 1:5,000 in assay diluent.

The ELISAs were performed as follows: Plates were coated using sterile filtered PBS pH 7.4+0.2 as the plate coating buffer. Test articles were diluted to optimized coating concentrations in coating buffer (optimum coating concentration for PS3 and 19A is 1 ug/mL, and PS5 and 18C is 2.5 ug/mL). 100 uL of diluted test article and positive control were added to their respective wells and the plate was held at 2-8° C. for 16-24 hours. The plate was then washed 3 times with plate washing buffer (350 uL/well). The plate was blocked by adding 200 uL of PBS+3% BSA to all wells. The plate was covered with a plate cover and incubated for at least 60+/−5 minutes at RT or overnight at 2-8° C. The plate was then washed 3 times with plate washing buffer (350 uL/well).

5-fold serial dilutions of the samples and negative control in 1×PBS+3% BSA were prepared, and 50 ul of each dilution was then transferred to the designated wells. Samples were loaded in duplicate and controls were loaded in singles, on one plate. The sample diluent, 1×PBS+3% BSA, was used as an additional control for background against the specific antigen. Negative control of a pool of the individual pre-immune serum was used with a starting dilution of 1:10 and serially diluted by 5. The positive control was diluted 1:750,000 and placed in at least 4 wells in a single column on the plate. The plate was placed in a sealed bag and incubated for 60-65 minutes at 35-39° C. The plate was washed 6 times with plate washing buffer (350 uL/well), and the second-antibody-enzyme-conjugate was diluted as needed in PBS+3% BSA before adding 100 uL to each well. Jackson ImmunoResearch reagents are diluted at 1:5,000 in PBS+3% BSA. The plate was covered with a plate cover, and incubate it for 60-65 minutes at RT. The plate was then washed 6 times with plate washing buffer (350 uL/well), and 100 uL per well of ABTS substrate solution was added to the plate. The plate was incubated for 30+/−1 minute at RT. The wells were read after the substrate incubation period at $A_{415nm}$ and $A_{570nm}$. Absorbance readings and curves were analyzed in the plate reader software.

Figure 2C:
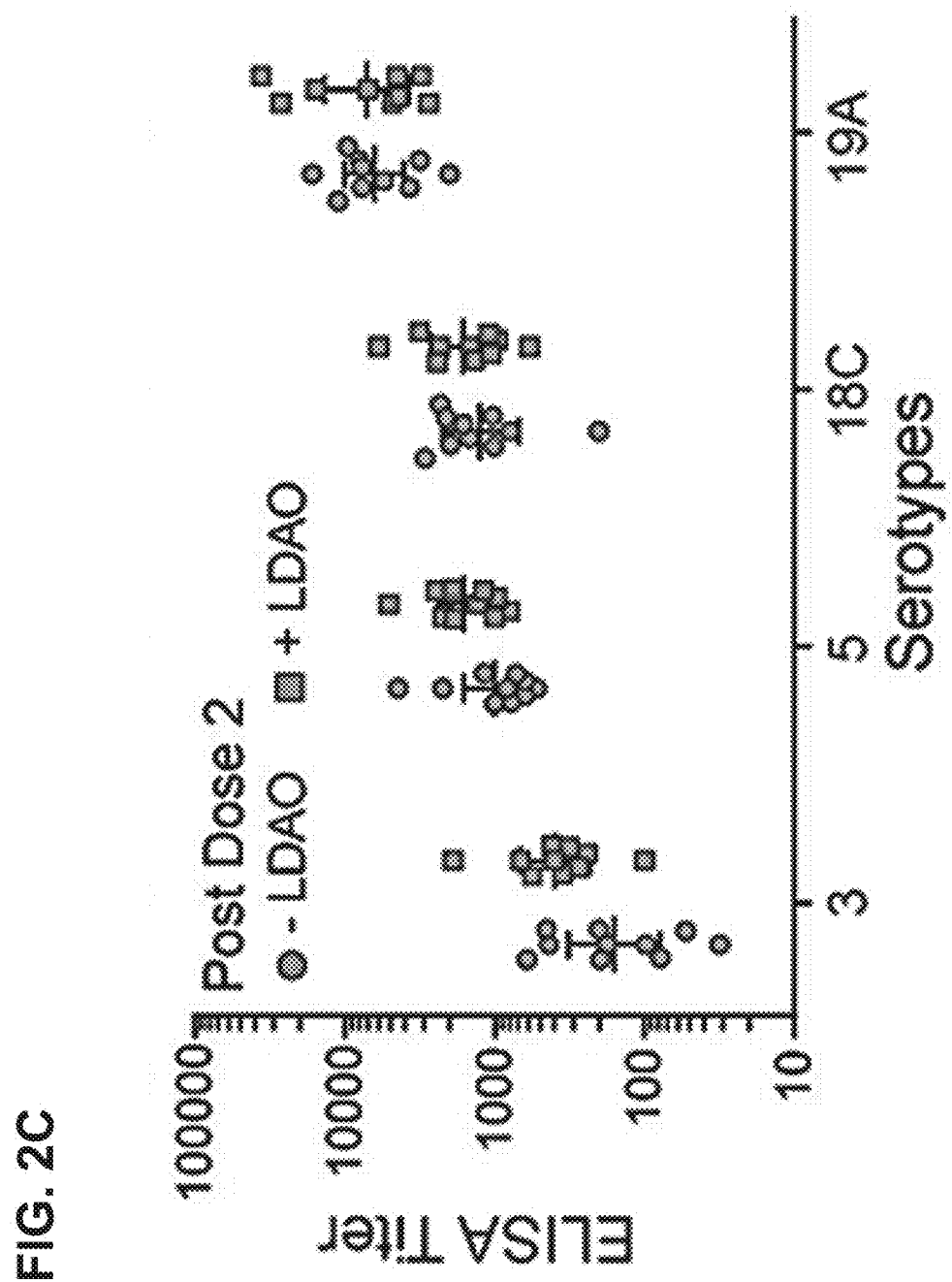
Figure 2D:
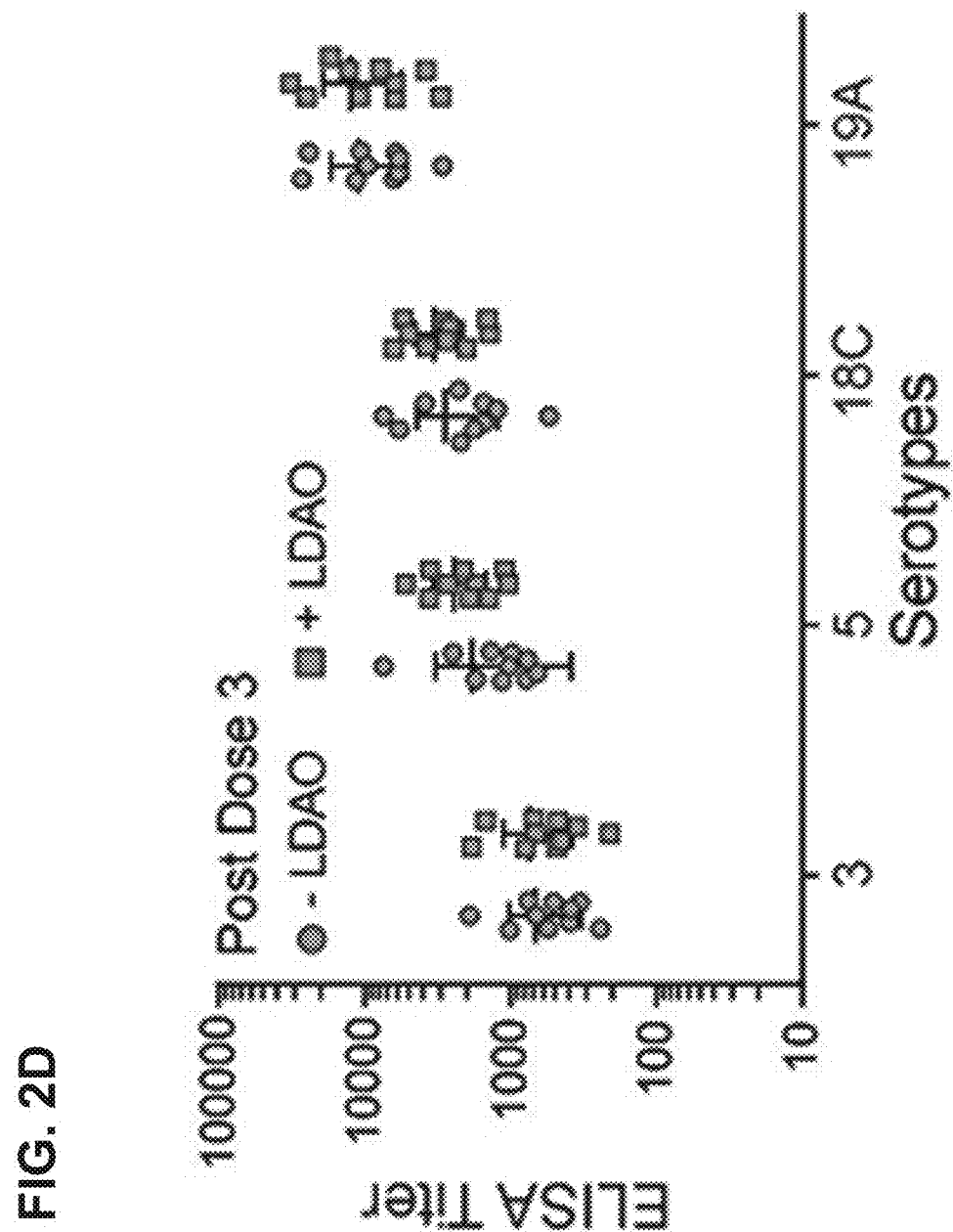
Figure 3B:
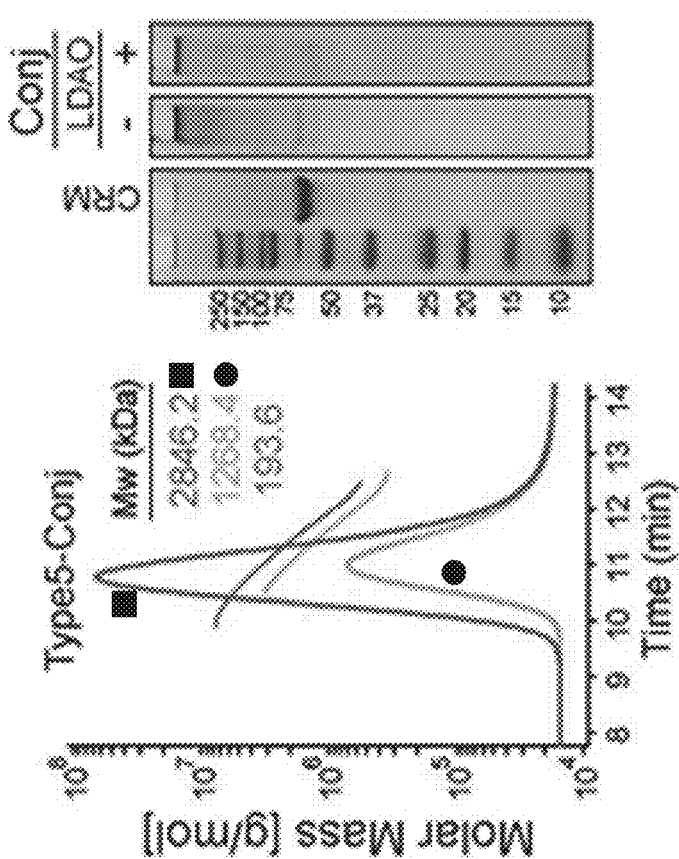
FIGS. 3A-3D show SEC-MALS plots and accompanying gels for conjugates of CRM-pAMF6 mutant and polysaccharide serotypes 3, 5, 18C, and 19A.
Figure 3A:
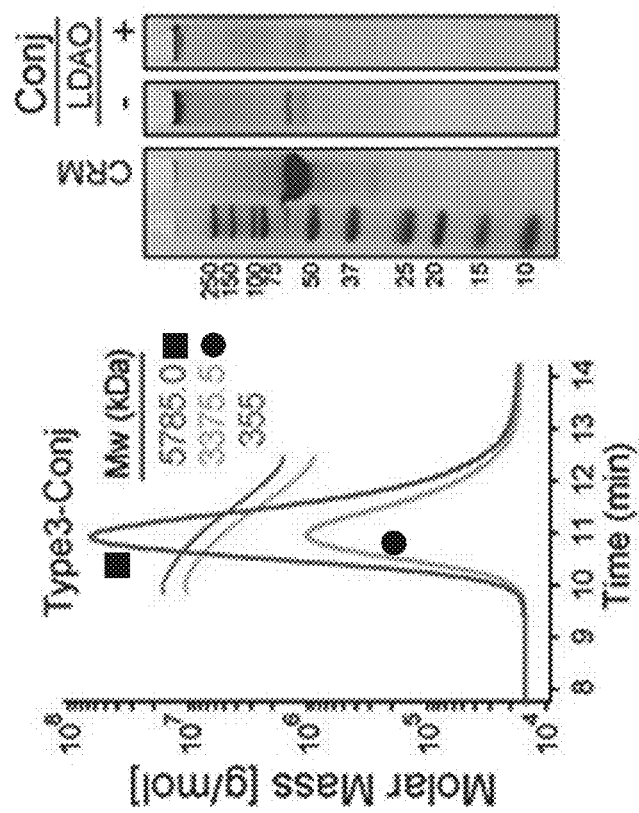
Figure 3D:
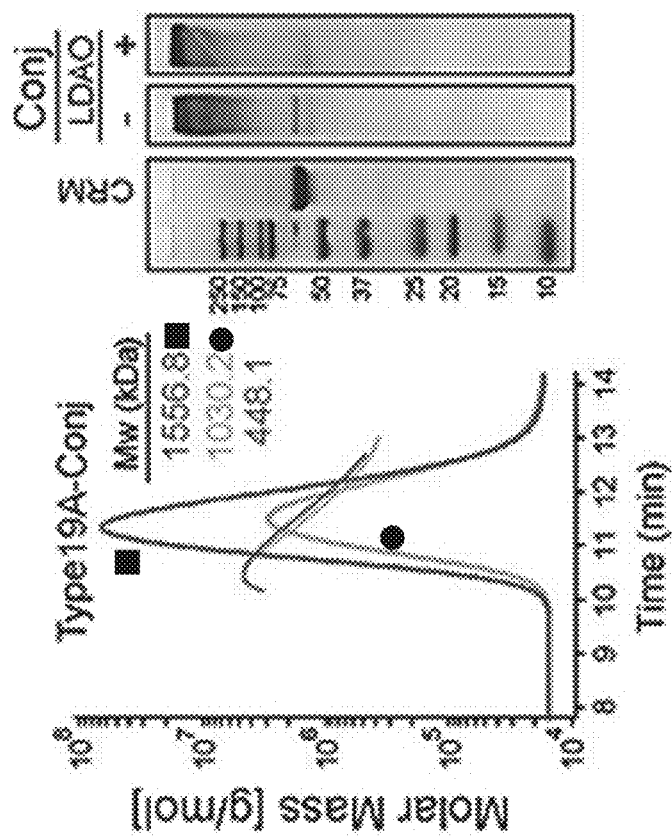
Figure 3C:
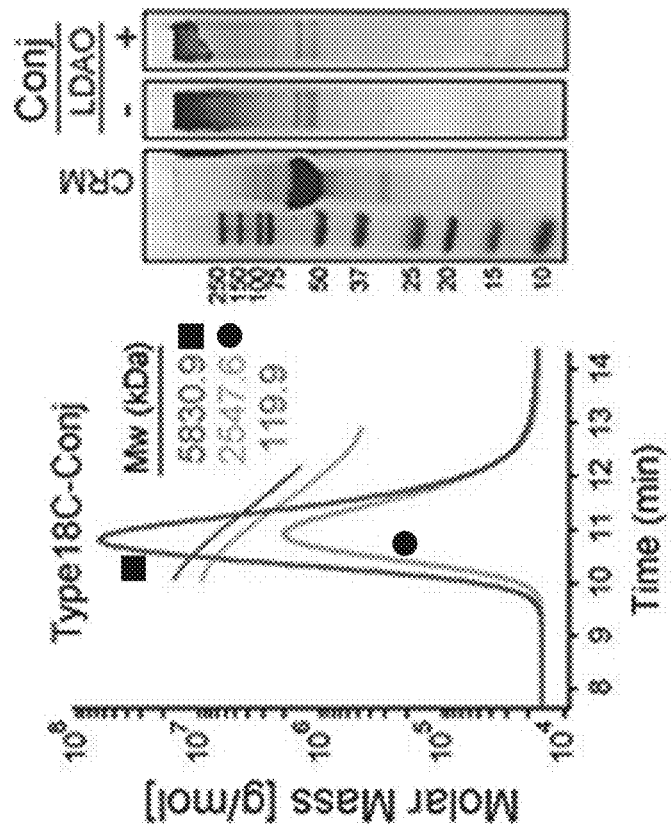

FIG. 2A shows the results of antibody titers after inoculation with PS conjugates (after administration of all doses). In all cases, conjugates of serotypes 3, 5, 18C, and 19A produced more robust antibody responses when they were produced using LDAO. FIG. 2B, FIG. 2C, and FIG. 2D show the antibody titer post-dose 1, post-dose 2, and post-dose 3, respectively.

Example 5: Deoxycholate Precipitation of Polypeptide-Polysaccharide Conjugates to Measure Free Polysaccharide Content Samples of conjugated polysaccharides were analyzed to determine their free (unconjugated) polysaccharide content. 1% (w/v) of sodium deoxycholate (DOC) solution at pH 6.8±0.03 was prepared by weighing out 500±0.1 mg of DOC and transferred to a 50 mL falcon tube. 50 mL of Milli-Q Water was added to the tube and mixed until all of the sodium deoxycholate was dissolved. The DOC was left at room temperature overnight to ensure it had completely dissolved after which the pH of the working solution was adjusted to pH 6.8. Once the DOC was made, we proceeded with the DOC precipitation. All conjugate samples, negative control (water), and reagents (1% DOC, pH 6.80±0.03 and 1M HCl) were brought to room temperature. To a 500 μL reaction containing a polysaccharide concentration of 0.250 mg/mL of each conjugate, 50 μL of 1% DOC, pH 6.80±0.03 was added. After the addition of DOC the reaction was mixed by pipetting for 10 cycles, and the samples were incubated on ice for 30 minutes, vortexed briefly after 15 minutes. After 30 minutes, 25 μL of 1M HCl was added to all the samples making sure to mix very well and waited for 5 minutes for precipitate to form. Then samples were centrifuged at 10,000 RPM at 4° C. for 20 minutes. The supernatant was collected and the pellet was discarded. Supernatant was centrifuged once more at 10,000 RPM at 4° C. for 10 minutes to ensure all pellet is separated. Supernatant was collected into a new tube again, and the pellet was discarded. The samples were then analyzed for their "% Free polysaccharide" (% FPS) content using an Anthrone assay.

Figures 6A, 6B:
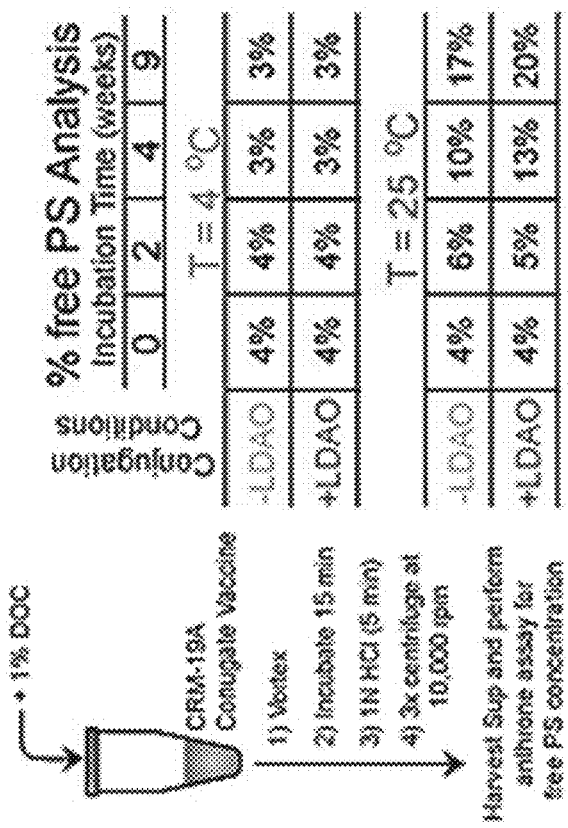
FIG. 6A shows a graphical workflow of the free PS analysis, as well as a comparison of the free polysaccharide content of a CRM-pAMF6-19A conjugate with and without LDAO as a function of both temperature and incubation duration.
FIG. 6B shows the percent conjugation for each of the polysaccharide 3, 5, 18C, and 19A conjugates with and without the use of LDAO.

FIG. 6A shows a graphical workflow of the free PS analysis, as well as a comparison of the free polysaccharide content of the CRM-pAMF6-19A conjugate with and without LDAO as a function of both temperature and incubation duration. FIG. 6B shows the percent conjugation for each of the PS3, PS5, PS18C, and PS19A conjugates with and without the use of LDAO.

While embodiments of the present invention have been shown and described herein, those skilled in the art will understand that such embodiments are provided by way of example only. Numerous variations, changes, and substitutions will now occur to those skilled in the art without departing from the invention. It should be understood that various alternatives to the embodiments of the invention described herein may be employed in practicing the invention. It is intended that the following claims define the scope of the invention and that methods and structures within the scope of these claims and their equivalents be covered thereby.

What is claimed herein is:

1. A method of preparing a heteroaryl-containing compound, the method comprising contacting an azide compound with an alkyne compound in the presence of lauryldimethylamine oxide (LDAO), water, and DMSO to form the heteroaryl-containing compound, wherein the LDAO is at a concentration of up to 2% v/v;

wherein the azide compound is a compound of formula (I)

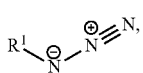
(I)

wherein the alkyne compound is a compound of formula (II) or (III)

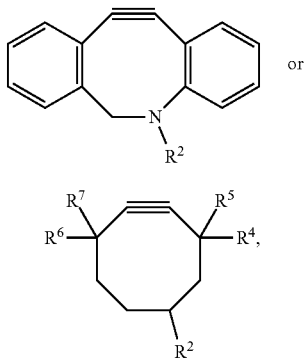

wherein $R^1$, $R^2$, and $R^3$ are independently selected from the group consisting of substituted or unsubstituted alkyl, substituted or unsubstituted alkenyl, substituted or unsubstituted alkynyl, substituted or unsubstituted alkoxy, substituted or unsubstituted cycloalkyl, substituted or unsubstituted aryl, substituted or unsubstituted heteroaryl, substituted or unsubstituted heterocyclyl, —$(CH_2)_a$—C(O)$R^{1a}$, —$(CH_2)_a$—C(O)OR$^{1a}$, —$(CH_2)_a$—C(O)N(R$^{1a}$)$_2$, —$(CH_2)_a$—C(O)NHCH(R$^{1a}$)$_2$, —$(CH_2)_a$—N(R$^{1a}$)$_2$; wherein a is integer from zero to 10; wherein each $R^{1a}$ is independently hydrogen, substituted or unsubstituted alkyl, substituted or unsubstituted alkenyl, substituted or unsubstituted alkoxy, substituted or unsubstituted cycloalkyl, substituted or unsubstituted aryl, substituted or unsubstituted heteroaryl, and substituted or unsubstituted heterocyclyl; or $R^1$ is a first polypeptide comprising at least one nonnatural amino acid residue (nnAAr) of formula (IV)

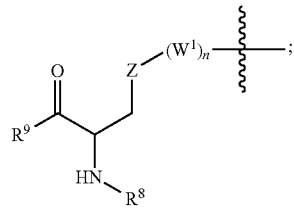
(IV)

wherein Z is absent or a 5-membered or 6-membered aryl or heteroaryl ring; $W^1$ is selected from the group consisting of $C_1$-$C_{10}$ alkylene, —NH—, —O— and —S—; n is zero or 1; $R^8$ is H or an amino acid residue of the first polypeptide, and $R^9$ is OH or an amino acid residue of the first polypeptide; and $R^2$ and $R^3$ are independently -$L^1$-$X^1$;

wherein $X^1$ is a polysaccharide or a second polypeptide;

$L^1$ is optional, and when present is a linker selected from the group consisting of substituted or unsubstituted alkylene, substituted or unsubstituted alkenylene, —O—, —O-(substituted or unsubstituted alkylene)-, -(substituted or unsubstituted alkylene)-O—, —O-(substituted or unsubstituted alkylene)-C(O)—$Y^1$—, —C(O)-(substituted or unsubstituted alkylene)-NH—$Y^2$—, —C(O)-(substituted or unsubstituted alkylene)-C(O)—, —C(O)-(substituted or unsubstituted alkylene)-NH—C(O)—$(CH_2$—$CH_2$—O$)_n$-(substituted or unsubstituted alkylene)-NH—, —C(O)-(substituted or unsubstituted alkylene)-NH—, —C(O)-(substituted or unsubstituted alkylene)-NH—C(O)—$(CH_2$—$CH_2$—O$)_n$-(substituted or unsubstituted alkylene)-C(O)—, —C(O)-(substituted or unsubstituted alkylene)-C(O)—NH-(substituted or unsubstituted alkylene)-, —C(O)—, —C(O)-(substituted or unsubstituted alkylene)-, -(substituted or unsubstituted alkylene)-C(O)—, —C(O)N($R^{L1}$)—, —C(O)N($R^{L1}$)-(substituted or unsubstituted alkylene)-, -(substituted or unsubstituted alkylene)-C(O)N($R^{L1}$), -(substituted or unsubstituted alkylene)-C(O)NR$^{L1}$-(substituted or unsubstituted alkylene)-, —OC(O)N($R^{L1}$)—, —OC(O)N($R^{L1}$)-(substituted or unsubstituted alkylene)-, -(substituted or unsubstituted alkylene)-OC(O)N($R^{L1}$)—, —N($R^{L1}$)C(O)—, —NR$^{L1}$C(O)-(substituted or unsubstituted alkylene)-, -(substituted or unsubstituted alkylene)-NR$^{L1}$C(O)—, —S—, —S-(substituted or unsubstituted alkylene)-, —S(O)$_k$—, —S(O)$_k$(alkylene or substituted alkylene)-, —C(S)—, —C(S)-(substituted or unsubstituted alkylene)-, —CSN($R^{L1}$)—, —CSN($R^{L1}$)-(substituted or unsubstituted alkylene)-, —N($R^{L1}$)C(O)O—, -(substituted or unsubstituted alkylene)-O—N=CR$^{L1}$—, -(substituted or unsubstituted alkylene)-S(O)$_k$-(substituted or unsubstituted alkylene)-S—, -(substituted or unsubstituted alkylene)-S—S—, —S(O)$_k$N ($R^{L1}$)—, —N($R^{L1}$)C(O)N($R^{L1}$)—, —N($R^{L1}$)C(S)N($R^{L1}$)—, —N($R^{L1}$)S(O)$_k$N($R^{L1}$)—, —N($R^{L1}$)—N=, —C($R^{L1}$)=N—, —C($R^{L1}$)=N—N($R^{L1}$)—, —C($R^{L1}$)=N—N=, —C($R^{L1}$)$_2$—N=N—, and —C($R^{L1}$)$_2$—N($R^{L1}$)—N($R^{L1}$)—; wherein the bond on the left side of $L^1$, as drawn, is bound to the 8-membered ring of the compound of formula (II) or the compound of formula (III) and the bond on the right side of the $L^1$, as drawn, is bound to $X^1$, $Y^1$ is a bond, —NH—, —O—, —S—, —NH($Y^{1a}$)—, —O($Y^{1a}$)—, or —S($Y^{1a}$)—;

$Y^2$ is a bond, —C(=O)—, —S(=O)$_2$—, —C(=O)Y$^{2a}$—, —S(=O)$_2$Y$^{2a}$, $Y^{1a}$ and $Y^{2a}$ are each independently $Y^3$ or $Y^3$NH—

$Y^3$ is substituted or unsubstituted $C_{1-10}$alkyl or —(CH$_2$CH$_2$O)$_{1-10}$—; and n is an integer from 1 to 30;

k is 1, 2, or 3;

each $R^{L1}$ is independently hydrogen or substituted or unsubstituted alkyl; and $R^4$, $R^5$, $R^6$, and $R^7$ are each independently hydrogen, halo, or substituted or unsubstituted alkyl.

2. The method of claim 1, wherein $R^1$ is a polypeptide comprising at least one non-natural amino acid residue (nnAAr).

3. The method of claim 1, wherein $R^1$ is a polypeptide comprising at least one non-natural amino acid residue (nnAAr) having a molecular weight of at least 15 kDa.

4. The method of claim 1, wherein the polypeptide comprising at least one non-natural amino acid residue (nnAAr) comprises 4-6 non-natural amino acids of formula (IV).

5. The method of any one of claims 1-4, wherein the non-natural amino acid residue of formula (IV), replaces a lysine residue in the polypeptide comprising at least one non-natural amino acid.

6. The method of any one of claims 1-4, wherein the polypeptide has at least 80% sequence identity, at least 85% sequence identity, at least 90% sequence identity, or at least 95% sequence identity to SEQ ID NO:1 or SEQ ID NO:2.

7. The method of claim 6, wherein the polypeptide comprises at least one residue sequence selected from the group consisting of residue sequences 271-290, 321-340, 331-350, 351-370, 411-430, and 431-450 of SEQ ID NO:1 that does not contain the at least 2 nnAArs.

8. The method of claim 6, wherein at least one nnAAr replaces an amino acid residue in SEQ ID NO: 1 selected from the group consisting of K11, K25, K34, K38, K40, K83, K104, K105, K126, K158, K173, K213, K215, K217, K222, K228, K230, K237, K243, K245, K265, K300, K386, K457, K475, K499, K517, K523, K527, K535, F13, F54, F124, F128, F141, F168, F251, F390, F531, F532, D212, D296, D353, D392, D466, D468, D508, D520, N297, N360, N400, N482, N487, N503, N525, E241, E249, E250, E257, E260, E293, E363, Q253, Q288, R378, R408, R456, R461, R463, R473, R494, S199, S201, S232, S234, S240, S262, S375, S382, S398, S452, S476, S495, S496, S497, S502, S506, T254, T266, T268, T270, T294, T387, T401, T409, T470, and T518.

9. The method of claim 6, wherein at least one nnAAr replaces an amino acid residue in SEQ ID NO: 1 selected from:
a) a first group consisting of K25, K34, K38, K40, K213, K215, K228, K245, K265, K386, K523, and K527;
b) a second group consisting of K25, K34, K38 and K40;
c) a third group consisting of K213 and K215;
d) a fourth group consisting of K11, K25, K34, K38, K40, K83, K104, K105, K126, K158, K173, K213, K215, K222, K228, K237, K243, K245, K265, K386, K475, K499, K523, K527, F13, F54, F124, F128, F141, F168, F251, F390, F531, and F532; and
e) a fifth group consisting of K25, K215, K228, K265, K386, and K523.

10. The method of claim 6, wherein 2-4 nnAArs replace amino acid residues in SEQ ID NO: 1 selected from the group consisting of K228, K245, K265, K386, K523, and K527.

11. The method of claim 1, wherein R1 is SEQ ID NO:2.

12. The method of claim 1, wherein Z is aryl.

13. The method of claim 1, wherein $W^1$ is —CH$_2$—.

14. The method of claim 1, wherein n is zero.

15. The method of claim 1, wherein the nnAAr of formula (IV) is

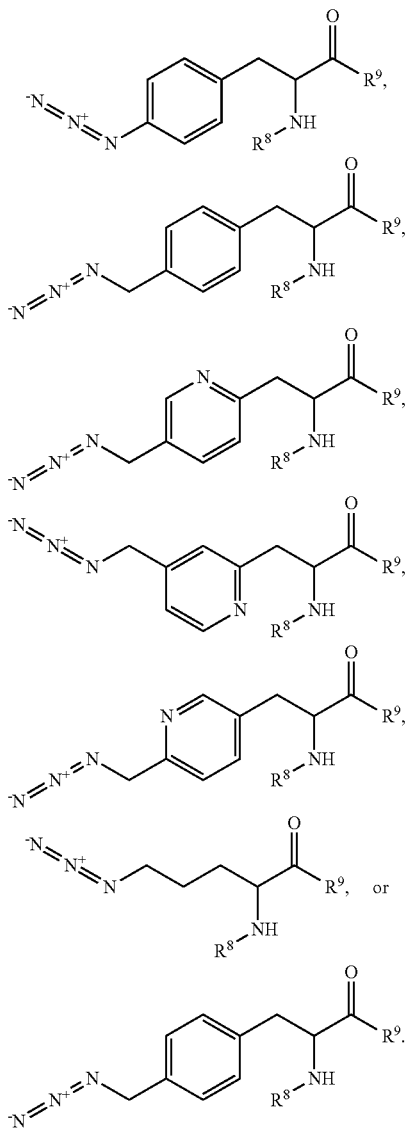

16. The method of claim 1, wherein $R^1$ is selected from the group consisting of substituted or unsubstituted alkyl, substituted or unsubstituted alkenyl, substituted or unsubstituted alkynyl, substituted or unsubstituted alkoxy, substituted or unsubstituted cycloalkyl, substituted or unsubstituted aryl, substituted or unsubstituted heteroaryl, substituted or unsubstituted heterocyclyl, —(CH$_2$)$_a$—C(O)R$^{1a}$, —(CH$_2$)$_a$—C(O)OR$^{1a}$, —(CH$_2$)$_a$—C(O)N(R$^{1a}$)$_2$, —(CH$_2$)$_a$—C(O)NHCH(R$^{1a}$)$_2$, —(CH$_2$)$_a$—N(R$^{1a}$)$_2$, wherein a is integer from zero to 10; wherein each R$^{1a}$ is independently hydrogen, substituted or unsubstituted alkyl, substituted or unsubstituted alkenyl, substituted or unsubstituted alkoxy, substituted or unsubstituted cycloalkyl, substituted or unsubstituted aryl, substituted or unsubstituted heteroaryl, and substituted or unsubstituted heterocyclyl.

17. The method of claim 1, wherein the azide compound is

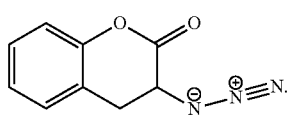 [SMILES: N#[N+][N-]C1Cc2ccccc2OC1=O]

18. The method of claim 1, wherein the alkyne compound is a compound of formula (V), (VI), (VII), (VIII), (IX), (X), (XI), or (XII):

(V)
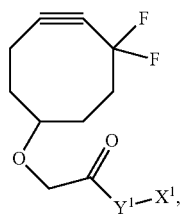

(VI)
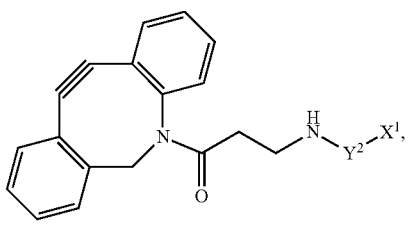

(VII)
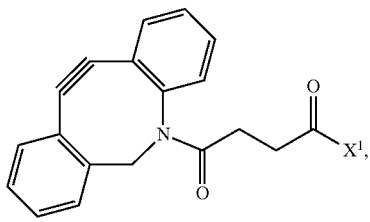

(VIII)
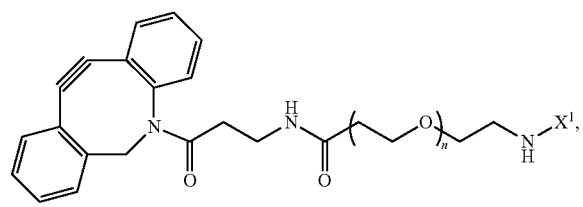

(IX)
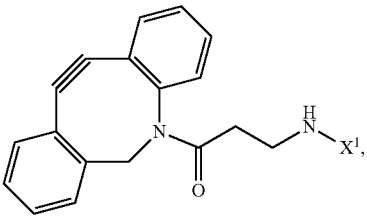

(X)
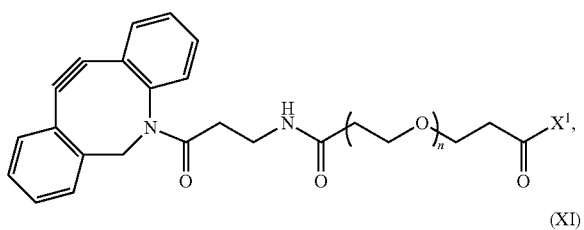

(XI)
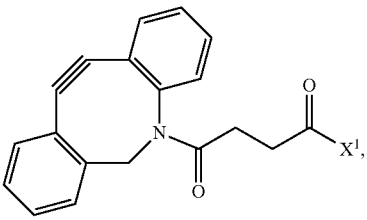

(XII)
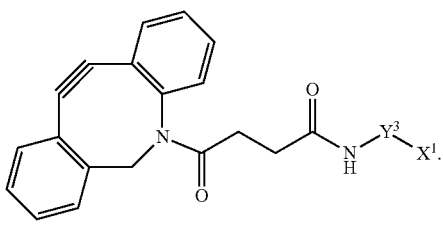

19. The method of claim 1, wherein X$^1$ is a polypeptide or polysaccharide.

20. The method of claim 1, wherein X$^1$ is a capsular polysaccharide from a bacterium selected from the group consisting of Streptococcus pneumoniae, Neisseria meningitidis, Haemophilus influenzae, Streptococcus pyogenes, Streptococcus agalactiae, and Porphyromonas gingivalis.

21. The method of claim 1, wherein X$^1$ is a capsular polysaccharide of a S. pneumoniae serotype selected from the group consisting of 1, 3, 4, 5, 6A, 6B, 7F, 9V, 14, 18C, 19A, 19F, 23F, 2, 6C, 8, 9N, 10A, 12F, 15A, 15B, 15C, 16F, 17F, 20, 20A, 20B, 22F, 23A, 23B, 24F, 24B, 31, 33F, 34, 35B, 35F and 38.

22. The method of claim 1, wherein the alkyne compound is a compound of formula (II):

(II)
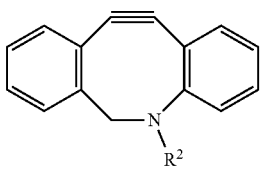

wherein R$^2$ is selected from the group consisting of substituted or unsubstituted alkyl, substituted or unsubstituted alkenyl, substituted or unsubstituted alkynyl, substituted or unsubstituted alkoxy, substituted or unsubstituted cycloalkyl, substituted or unsubstituted aryl, substituted or unsubstituted heteroaryl, substituted or unsubstituted heterocyclyl, —$(CH_2)_a$—$C(O)R^{1a}$, —$(CH_2)_a$—$C(O)OR^{1a}$, —$(CH_2)_a$—$C(O)N(R^{1a})_2$, —$(CH_2)_a$—$C(O)NHCH(R^{1a})_2$, —$(CH_2)_a$—$N(R^{1a})_2$; wherein a is integer from zero to 10; wherein each $R^{1a}$ is independently hydrogen, substituted or unsubstituted alkyl, substituted or unsubstituted alkenyl, substituted or unsubstituted alkoxy, substituted or unsubstituted cycloalkyl, substituted or unsubstituted aryl, substituted or unsubstituted heteroaryl, and substituted or unsubstituted heterocyclyl.

23. The method of claim 1, wherein the alkyne compound is a compound of formula (III)

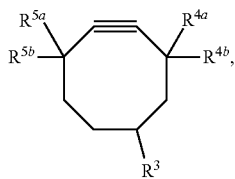

wherein $R^3$ is selected from the group consisting of substituted or unsubstituted alkyl, substituted or unsubstituted alkenyl, substituted or unsubstituted alkynyl, substituted or unsubstituted alkoxy, substituted or unsubstituted cycloalkyl, substituted or unsubstituted aryl, substituted or unsubstituted heteroaryl, substituted or unsubstituted heterocyclyl, —$(CH_2)_a$—$C(O)R^{1a}$, —$(CH_2)_a$—$C(O)OR^{1a}$, —$(CH_2)_a$—$C(O)N(R^{1a})_2$, —$(CH_2)_a$—$C(O)NHCH(R^{1a})_2$, —$(CH_2)_a$—$N(R^{1a})_2$; wherein a is integer from zero to 10; wherein each $R^{1a}$ is independently hydrogen, substituted or unsubstituted alkyl, substituted or unsubstituted alkenyl, substituted or unsubstituted alkoxy, substituted or unsubstituted cycloalkyl, substituted or unsubstituted aryl, substituted or unsubstituted heteroaryl, and substituted or unsubstituted heterocyclyl.

24. The method of claim 1, wherein the LDAO is at a concentration of 0.05% v/v to 2% v/v.

25. The method of claim 1, wherein method is performed in 10 to 20% v/v DMSO.

26. The method of claim 1, wherein the alkyne compound is at a concentration of 0.5 mg/ml to 2 mg/ml.

27. The method of claim 1, wherein the first polypeptide comprising at least one non-natural amino acid is at a concentration of 0.5 mg/ml to 2 mg/ml.

28. The method of claim 1, wherein the method is performed at room temperature.

29. The method of claim 1, wherein the method is performed for about 2 to 8 hours.

* * * * *